US008394590B2

(12) United States Patent
Kwong et al.

(10) Patent No.: US 8,394,590 B2
(45) Date of Patent: Mar. 12, 2013

(54) CAPTURE AGENTS AND RELATED METHODS AND SYSTEMS FOR DETECTING AND/OR SORTING TARGETS

(75) Inventors: Gabriel A. Kwong, Alhambra, CA (US); Caius G. Radu, Los Angeles, CA (US); Owen Witte, Sherman Oaks, CA (US); James R. Heath, South Pasadena, CA (US); Antoni Ribas, Los Angeles, CA (US)

(73) Assignees: California Institute of Technology, Pasadena, CA (US); University of California, Oakland, CA (US)

( * ) Notice: Subject to any disclaimer, the term of this patent is extended or adjusted under 35 U.S.C. 154(b) by 0 days.

(21) Appl. No.: 12/901,151

(22) Filed: Oct. 8, 2010

(65) Prior Publication Data

US 2011/0166034 A1 Jul. 7, 2011

Related U.S. Application Data

(63) Continuation of application No. PCT/US2009/040106, filed on Apr. 9, 2009, which is a continuation-in-part of application No. 11/888,502, filed on Aug. 1, 2007, now abandoned.

(60) Provisional application No. 61/123,478, filed on Apr. 9, 2008, provisional application No. 60/834,823, filed on Aug. 2, 2006, provisional application No. 60/959,665, filed on Jul. 16, 2007.

(51) Int. Cl.
*C12Q 1/68* (2006.01)
(52) U.S. Cl. ............... 435/6.12; 435/7.1; 435/287.2
(58) Field of Classification Search .......... 435/6.12, 435/7.1, 287.2
See application file for complete search history.

(56) References Cited

U.S. PATENT DOCUMENTS

| 6,391,590 | B1* | 5/2002 | Sano et al. ............ 435/69.7 |
| 2002/0168640 | A1* | 11/2002 | Li et al. ............... 435/6 |
| 2003/0082601 | A1 | 5/2003 | Dill |
| 2004/0086960 | A1* | 5/2004 | Reiter ................. 435/69.1 |
| 2009/0036324 | A1 | 2/2009 | Fan et al. |

FOREIGN PATENT DOCUMENTS

| EP | 1816476 A1 | 8/2007 |
| WO | WO 2007/014267 A2 | 2/2007 |
| WO | WO 2008/016680 A1 | 2/2008 |

OTHER PUBLICATIONS attached amino acid sequence search report.*
Altman, J. D., et al., "Phenotypic Analysis of Antigen-Specific T Lymphocytes," Science 274:94-96 (1996).
Arenkov, P., et al., "Protein Microchips: Use for Immunoassay and Enzymatic Reactions," Anal. Biochem. 278:123-131 (2000).
Bailey, R. C., et al., "DNA-Encoded Antibody Libraries: A Unified Platform for Multiplexed Cell Sorting and Detection of Genes and Proteins," J. Am. Chem. Soc. 129:1959-1967 (2007).
Bakker, A. H., et al., "Conditional MHC Class I Ligands and Peptide Exchange Technology for the Human MHC Gene Products HLA-A1, -A3, -All, and -B7," Proc. Natl. Acad. Sci. 105(10):3825-3830 (2008).
Baugh, C., et al., "2.8 A Crystal Structure of the Malachite Green Aptamer," J. Mol. Biol. 301:117-128 (2000).
Boozer, C., et al., "DNA-Directed Protein Immobilization for Simultaneous Detection of Multiple Analytes by Surface Plasmon Resonance Biosensor," Anal. Chem. 78:1515-1519 (2006).
Breslauer, D. N., et al., "Microfluidics-Based Systems Biology," Mol. BioSyst. 2:97-112 (2006).
Bustamante, C., "Entropic Elasticity of λ-Phage DNA," Science 265:1599-1600 (1994).
Butler, J.E., et al., "The Physical and Functional Behavior of Capture Antibodies Adsorbed on Polystyrene," J. Immunol. Methods 150:77-90 (1992).
Butler, J. E., et al., "The Immunochemistry of Sandwich ELISAs—VI. Greater Than 90% of Monoclonal and 75% of Polyclonal Anti-Fluorescyl Capture Antibodies (CAbs) are Denatured by Passive Adsorption," Mol. Immunol. 30(13):1165-1175 (1993).
Cameron, T. O., et al., "Cutting Edge: Detection of Antigen-Specific CD4+ T Cells by HLA-DR1 Oligomers Is Dependent on the T Cell Activation State," J. Immunol. 166:741-745 (2001).
Cardoso, A. A., et al., "An Improved Panning Technique for the Selection of CD34+ Human Bone Marrow Hematopoietic Cells with High Recovery of Early Progenitors," Exp. Hematol. 23:407-412 (1995).
Carrico, I. S., et al., "Introducing Genetically Encoded Aldehydes Into Proteins," Nat. Chem. Biol. 3(6):321-322 (2007).
Chandra, R. A., et al., "Programmable Cell Adhesion Encoded by DNA Hybridization," Angew. Chem. Int. Ed. 45:896-901 (2006).
Chattopadhyay, P. K., et al., "Quantum Dot Semiconductor Nanocrystals for Immunophenotyping by Polychromatic Flow Cytometry," Nat. Med. 12(8):972-977 (2006).
Chen, D. S., et al., "Marked Differences in Human Melanoma Antigen-Specific T Cell Responsiveness After Vaccination Using a Functional Microarray," PLoS Med. 2:1018-1030 (2005).
Deviren, G., et al., "Detection of Antigen-Specific T Cells on p/MHC Microarrays," J. Mol. Recognit. 20:32-38 (2007).
Dirks, R. M., et al., "Paradigms for Computational Nucleic Acid Design," Nucl. Acids Res. 32(4):1392-1403 (2004).
Fan, R., et al., "Integrated Blood Barcode Chips," Nat. Biotechnol. 26(12):1373-1378 (2008). Garboczi, D. N., et al., "HLA-A2-Peptide Complexes: Refolding and Crystallization of Molecules Expressed in *Escherichia coli* and Complexed with Single Antigenic Peptides," Proc. Natl. Acad. Sci. 89:3429-3433 (1992).
Green, N. M., "Spectrophotometric Determination of Avidin and Biotin," Methods Enzymol. 18:418-424 (1970).
Grotenbreg, G. M., et al., "Discovery of CD8+ T Cell Epitopes in Chlamydia Trachomatis Infection Through Use of Caged Class I MHC Tetramers," Proc. Natl. Acad. Sci. 105(10):3831-3836 (2008).
Haab, B. B., et al., "Protein Microarrays for Highly Parallel Detection and Quantitation of Specific Proteins and Antibodies in Complex Solutions," Genome Biol. 2(2):1-13 (2001).

(Continued)

*Primary Examiner* — Christopher M. Babic
*Assistant Examiner* — Joyce Tung
(74) *Attorney, Agent, or Firm* — Lathrop & Gage LLP; Sean M. Coughlin, Esq.

(57) ABSTRACT

Polynucleotide-encoded capture agents for target detection and in particular modular polynucleotide-capture agents comprising a target binding component, a scaffold component and an encoding component formed by standardized molecular units that can be coupled and decoupled in a controlled fashion, and related compositions methods and systems.

14 Claims, 21 Drawing Sheets

OTHER PUBLICATIONS

Hays, J. B., et al., "Persistence Length of DNA," Biopolymers 8:531-536 (1969).

Hendrickson, W. A., et al., "Crystal Structure of Core Streptavidin Determined from Multiwavelength Anomalous Diffraction of Synchrotron Radiation," Proc. Natl. Acad. Sci. 86:2190-2194 (1989).

Hsiao, S. C., et al., "DNA-Coated AFM Cantilevers for the Investigation of Cell Adhesion and the Patterning of Live Cells," Angew. Chem. Int. Ed. Engl. 47(44):8473-8477 (2008).

Johnson, L. A., et al., "Gene Transfer of Tumor-Reactive TCR Confers Both High Avidity and Tumor Reactivity to Nonreactive Peripheral Blood Mononuclear Cells and Tumor-Infiltrating Lymphocytes," J. Immunol. 177(9):6548-6559 (2006).

Kiyonaka, S., et al., "Semi-Wet Peptide/Protein Array Using Supramolecular Hydrogel," Nat. Mater. 3:58-64 (2004).

Korean Intellectual Property Office, International Preliminary Report on Patentability dated Oct. 12, 2010 for PCT/US2009/040106.

Kwon, Y., et al., "Antibody Arrays Prepared by Cutinase-Mediated Immobilization on Self-Assembled Monolayers," Anal. Chem. 76:5713-5720 (2004).

Lesaicherre, M.L., et al., "Intein-Mediated Biotinylation of Proteins and Its Application in a Protein Microarray," J. Am. Chem. Soc. 124:8768-8769 (2002).

Macbeath, G., et al., "Printing Proteins as Microarrays for High-Throughput Function Determination," Science 289:1760-1763 (2000).

Matsui, K., et al., "Kinetics of T-Cell Receptor Binding to Peptide/I-$E^k$ Complexes: Correlation of the Dissociation Rate with T-Cell Responsiveness," Proc. Natl. Acad. Sci. 91:12862-12866 (1994).

McLaughlin, B. E., et al., "Nine-Color Flow Cytometry for Accurate Measurement of T Cell Subsets and Cytokine Responses. Part I: Panel Design by an Empiric Approach," Cytometry Part A 73A:400-410 (2008).

Meagher, J. L., et al., "Crystal Structure of Banana Lectin Reveals a Novel Second Sugar Binding Site," Glycobiology 15(10):1033-1042 (2005).

Morgan, R. A., et al., "Cancer Regression in Patients After Transfer of Genetically Engineered Lymphocytes," Science 314(5796):126-129 (2006).

Niemeyer, C. M., "Functional Devices from DNA and Proteins," Nano Today 2(2):42-52 (2007).

Nishimura, M. I., et al., "MHC Class I-Restricted Recognition of a Melanoma Antigen by a Human $CD4^+$ Tumor Infiltrating Lymphocyte," Cancer Res. 59:6230-6238 (1999).

Peluso, P., et al., "Optimizing Antibody Immobilization Strategies for the Construction of Protein Microarrays," Anal. Biochem. 312:113-124 (2003).

Ramachandiran, V., et al., "A Robust Method for Production of MHC Tetramers with Small Molecule Fluorophores," J. Immunol. Methods 319(1-2):13-20 (2007).

Reznik, G. O., et al., "A Streptavidin Mutant Useful for Directed Immobilization on Solid Surfaces," Bioconjugate Chem. 12:1000-1004 (2001).

Sano, T., et al., "Expression of a Cloned Streptavidin Gene in *Escherichia coli*," Proc. Natl. Acad. Sci. 87:142-146 (1990).

Sano, T., et al., "Immuno-PCR: Very Sensitive Antigen Detection by Means of Specific Antibody-DNA Conjugates," Science 258:120-122 (1992).

Schena, M., et al., "Quantitative Monitoring of Gene Expression Patterns with a Complementary DNA Microarray," Science 270:467-470 (1995).

Schumacher, T. N. M., "T-Cell-Receptor Gene Therapy," Nat. Rev. Immunol. 2:512-519 (2002).

Soen, Y., et al., "Detection and Characterization of Cellular Immune Responses Using Peptide-MHC Microarrays," PLoS Biol. 1(3):429-438 (2003).

Stone, J. D., et al., "HLA-Restricted Epitope Identification and Detection of Functional T Cell Responses by Using MHC-Peptide and Costimulatory Microarrays," Proc. Natl. Acad. Sci. 102(10):3744-3749 (2005).

Szymczak, A. L., et al., "Correction of Multi-Gene Deficiency in Vivo Using a Single 'Self-Cleaving' 2A Peptide-Based Retroviral Vector," Nat. Biotech. 22(5):589-594 (2004).

Toebes, M., et al., "Design and Use of Conditional MHC Class I Ligands," Nat. Med. 12(2):246-251 (2006).

Zimmermann, M., et al., "Modeling and Optimization of High-Sensitivity, Low-Volume Microfluidic-Based Surface Immunoassays," Biomed. Microdevices 7(2):99-110 (2005).

Kwong, G. A., et al., "Modular Nucleic Acid Assembled p/MHC Microarrays for Multiplexed Sorting of Antigen-Specific T Cells," J. Am. Chem. Soc. 131:9695-9703 (2009).

Norimine, J., et al., "Quantitation of Anaplasma Marginale Major Surface Protein (MSP)1a and MSP2 Epitope-Specific $CD4^+$ T Lymphocytes Using Bovine DRB3*1101 and DRB3*1201 Tetramers," Immunogenetics 58:726-739 (2006).

Sano, T., et al., "A Streptavidin Mutant Containing a Cysteine Stretch That Facilitates Production of a Variety of Specific Streptavidin Conjugates," Biotechnol. 11:201-206 (1993).

Yang, J., et al., "In Vivo Biotinylation of the Major Histocompatibility Complex (MHC) Class II/Peptide Complex by Coexpression of BirA Enzyme for the Generation of MHC Class II/Tetramers," Human Immunol. 65:692-699 (2004).

Yokouchi, H., et al., "Tetramer-Blocking Assay for Defining Antigen-Specific Cytotoxic T Lymphocytes Using Peptide-MHC Tetramer," Cancer Sci. 97:148-154 (2006).

* cited by examiner

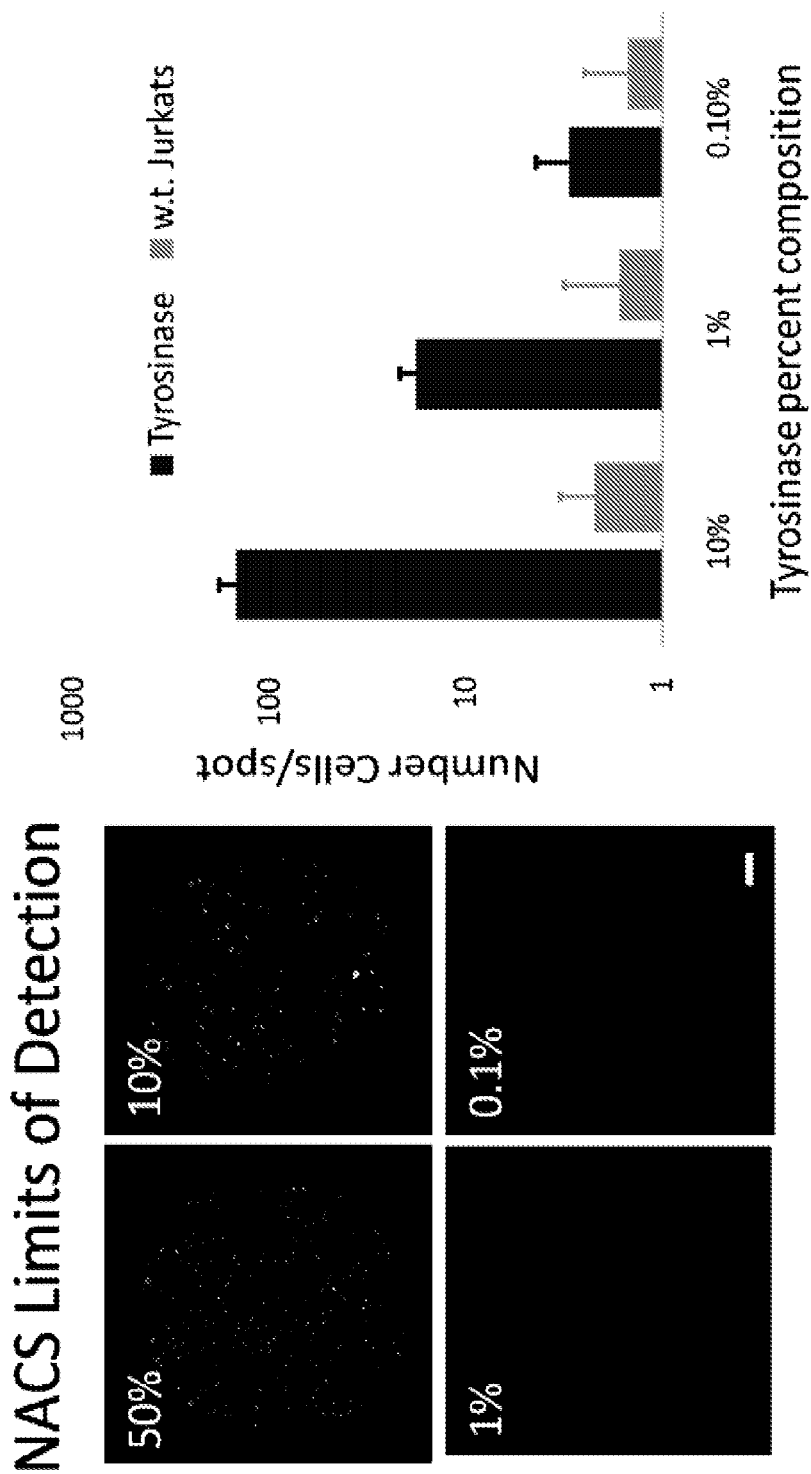

A
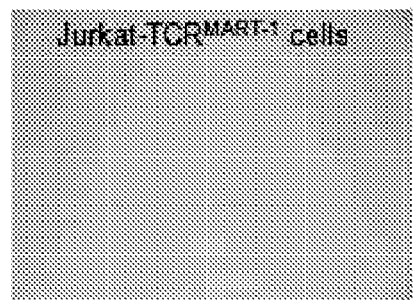
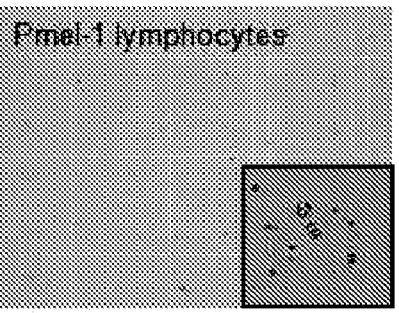
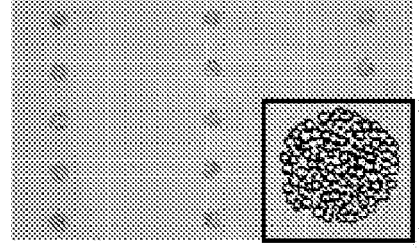
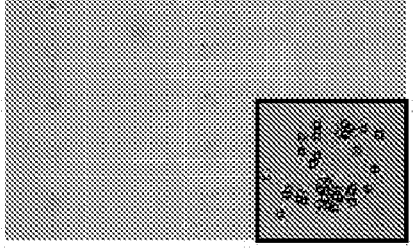
B
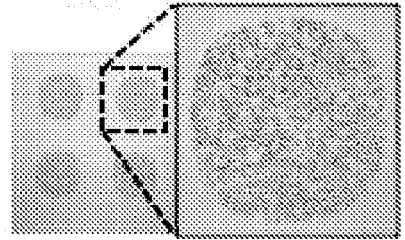
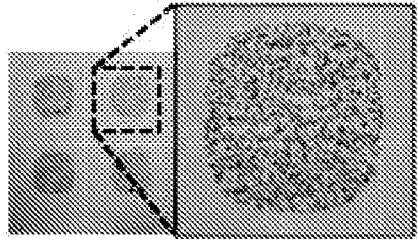
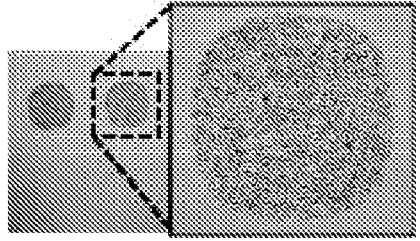
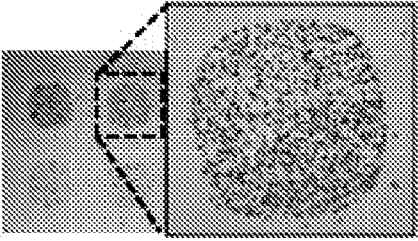
FIG. 9

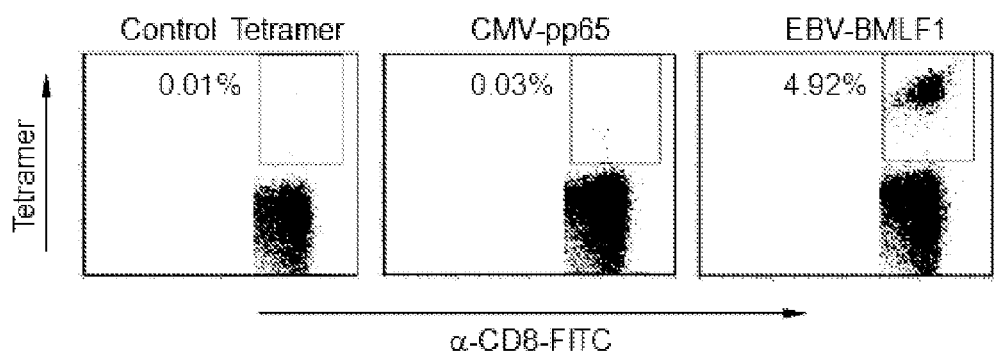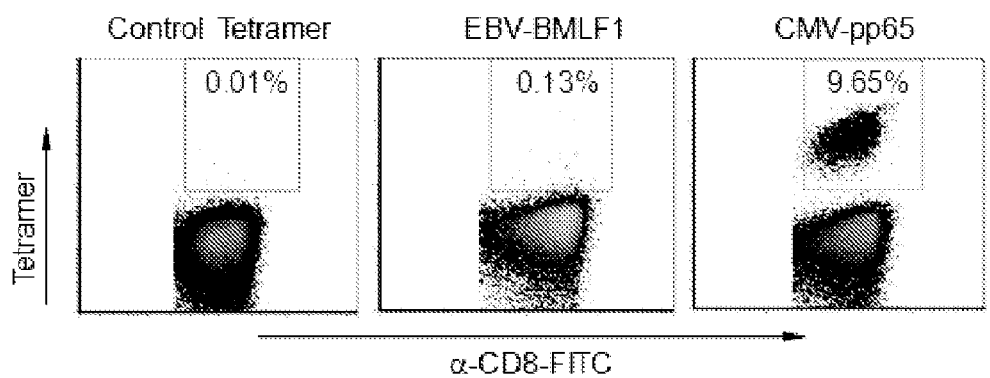
FIG. 14

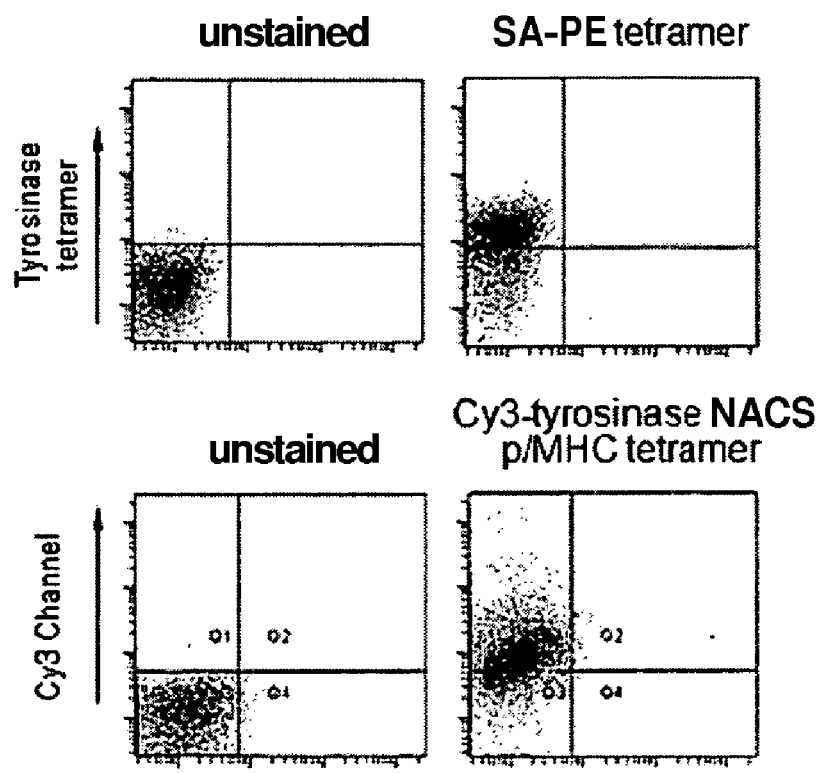
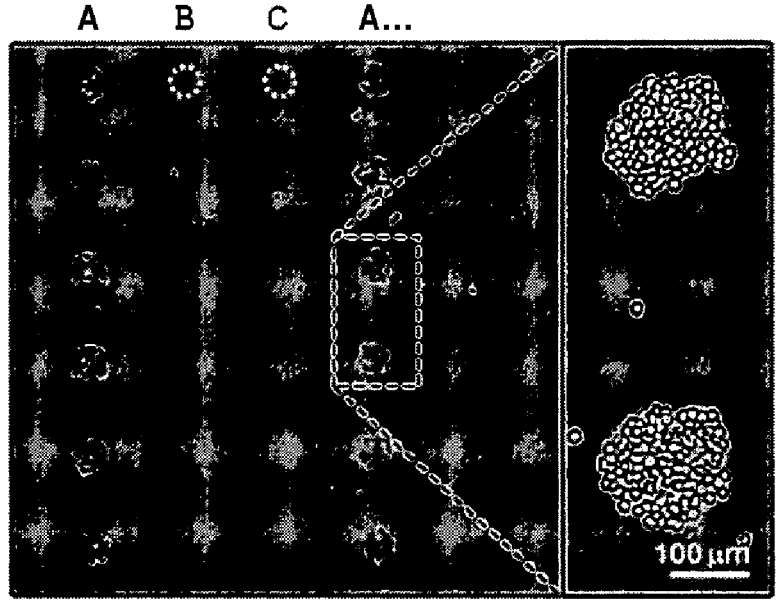
FIG. 17

US 8,394,590 B2

CAPTURE AGENTS AND RELATED METHODS AND SYSTEMS FOR DETECTING AND/OR SORTING TARGETS

CROSS REFERENCE TO RELATED APPLICATIONS

This application is a continuation of PCT International Application No. PCT/US2009/040106, filed with the U.S. Receiving Office on Apr. 9, 2009 and designating the U.S., which claims priority to U.S. Provisional Application Ser. No. 61/123,478, filed on Apr. 9, 2008, both of which are incorporated herein by reference in their entirety. PCT International Application No. PCT/US2009/040106 is also a continuation-in-part of U.S. application Ser. No. 11/888,502, filed on Aug. 1, 2007 now abandoned, which claims priority to U.S. Provisional Application Ser. No. 60/834,823, filed on Aug. 2, 2006, and to U.S. Provisional Application Ser. No. 60/959,665, filed on Jul. 16, 2007. These five applications are incorporated herein by reference in their entirety. This application might also be related to U.S. application Ser. No. 12/174,598, filed on Jul. 16, 2008, and to U.S. application Ser. No. 12/174,601, filed on Jul. 16, 2008, the disclosures of both of which are also incorporated herein by reference in their entirety.

STATEMENT OF GOVERNMENT GRANT

This invention was made with Government support under Grant No. CA119347 awarded by the National Cancer Institute at Frederick and pursuant to Grant No. DAAD19-03-D-0004/0008 and Grant No. 5U54CA119347 awarded by ARO-US Army Robert Morris Acquisition Center. The Government has certain rights in this invention.

TECHNICAL FIELD

The present disclosure relates to detection and/or sorting of one or more targets, in particular biomarkers, in a sample, such as a biological sample. More specifically, it relates to capture agents and related methods and systems for detecting and/or sorting targets.

BACKGROUND

High sensitivity detection of targets and in particular of biomarkers has been a challenge in the field of biological molecule analysis, in particular when aimed at detection of a plurality of targets and/or at detection of target of a certain dimension or present in the sample at a low concentration. Whether for pathological examination or for fundamental biology studies, several methods are commonly used for the detection of various classes of biomaterials and biomolecules.

Some of the techniques most commonly used in the laboratory for detection of single biological targets include gel electrophoresis, polyacrylamide gel electrophoresis (PAGE), western blots, fluorescent in situ hybridization (FISH), Florescent activated cell sorting (FACS), Polymerase chain reaction (PCR), and enzyme linked immunosorbent assay (ELISA). These methods have provided the ability to detect one or more biomarkers in biological samples such as tissues and are also suitable for diagnostic purposes.

Subsequent polynucleotide encoding approaches, developed by Applicants, provided improvements over previous techniques, and in particular, allowed performance of a highly sensitive and selective multiplex detection of targets.

SUMMARY

Provided herein are polynucleotide encoded capture agents and in particular modular capture agents and related arrays methods and systems that allow, in several embodiments, selective and sensitive detection of a vast series of targets, through a flexible and versatile modular molecular tool.

In particular, a modular polynucleotide-encoded capture agent herein described comprises a target binding component, a scaffold component and an encoding component formed by standardized molecular units that can be coupled and decoupled in a controlled fashion. Accordingly, in the modular capture agent here described, not only a same scaffold can be combined with different target binding structures, but also a same scaffold can be combined with a plurality of target binding structures, thus significantly improving detection, sensitivity and selectivity achievable by the capture agents.

According to a first aspect, a modular polynucleotide-encoded capture agent configured for specific binding to a target is described. The modular polynucleotide-encoded capture agent comprises at least one binding molecule configured to specifically bind to the target, an encoding polynucleotide configured to specifically bind to a substrate polynucleotide attached to a substrate, and a scaffold molecule configured to attach the at least one binding molecule and the encoding polynucleotide with positionally distinguishable scaffold binding domains. In the scaffold molecule, the positionally distinguishable scaffold binding domains are arranged to allow, upon binding with the at least one binding molecule and with the encoding polynucleotide, presentation of the at least one binding molecule for specific binding to the target and of the encoding polynucleotide for specific binding to the substrate polynucleotide.

According to a second aspect, a method and a system to detect a target in a sample are disclosed, the method and system based on the combined use of a substrate polynucleotide attached to a substrate, and a modular polynucleotide-encoded capture agent, comprising a scaffold molecule attaching at least one binding molecule and an encoding polynucleotide. In the modular polynucleotide-encoded capture agent the at least one binding molecule is configured to specifically bind to the target and the encoding polynucleotide is configured to specifically bind to the substrate polynucleotide attached to the substrate.

In the method, the modular polynucleotide-encoded capture agent and/or the units composing said modular polynucleotide-encoded capture agent, the sample and the substrate polynucleotide are contacted for a time and under conditions to allow binding of the at least one binding molecule with the target in a modular polynucleotide-encoded capture agent-target complex, and binding of the encoding polynucleotide with the substrate polynucleotide, thus providing a modular polynucleotide-encoded capture agent-target complex bound to the substrate polynucleotide. In the method, the modular polynucleotide-encoded capture agent-target complex bound to the substrate polynucleotide is then detected by way of detecting techniques which will be identifiable by a skilled person upon reading of the present disclosure.

In the system, a substrate with a substrate polynucleotide attached to the substrate is provided, together with at least one binding molecule that is configured to specifically bind to the target, an encoding polynucleotide specifically binding to the substrate polynucleotide attached to the substrate, and a scaffold molecule configured to attach the at least one binding molecule and the encoding polynucleotide with positionally distinguishable scaffold binding domains. In the scaffold molecule, the positionally distinguishable scaffold binding domains are arranged to allow, upon binding with the at least one binding molecule and with the encoding polynucleotide, presentation of the at least one binding molecule for specific binding to the target and of the encoding polynucleotide for specific binding to the substrate polynucleotide.

According to a third aspect, a method and system for sorting targets of a plurality of targets are disclosed, the method and system based on the combined use of a plurality of substrate polynucleotides attached to a substrate and a plurality of modular polynucleotide-encoded capture agents. In some embodiments, the targets are cells and the method and systems are for sorting a plurality of cells.

In the method and system, each substrate polynucleotide is sequence-specific and positionally distinguishable from another. In the method and system, each modular polynucleotide-encoded capture agent is comprised of at least one binding molecule configured to specifically bind to a complementary target of the plurality of targets, an encoding polynucleotide configured to specifically bind to a substrate polynucleotide of the plurality of substrate polynucleotides, and a scaffold molecule configured to bind to the at least one binding molecule and the encoding polynucleotide with positionally distinguishable scaffold binding domains, the positionally distinguishable scaffold binding domains being arranged on the scaffold molecule to allow, upon binding with the at least one binding molecule and with the encoding polynucleotide, presentation of the at least one binding molecule for specific binding to the target and of the encoding polynucleotide for specific binding to the substrate polynucleotide.

In the method, the plurality of modular polynucleotide-encoded capture agents and/or the units forming said plurality of modular polynucleotide-encoded capture agents, are contacted with the sample for a time and under conditions to allow binding of the at least one binding molecule with the targets, thus providing a plurality of modular polynucleotide-encoded capture agent-target complexes. In the method, the plurality of polynucleotide-encoded capture agent-target complexes is then contacted with the plurality of substrate polynucleotides for a time and under conditions to allow binding of the encoding polynucleotides to the substrate polynucleotides attached to the substrate, thus sorting the plurality of targets in a plurality of polynucleotide-encoded capture agent-target complexes bound to the substrate.

In the system, a substrate with the plurality of substrate polynucleotides attached to the substrate is comprised, together with a plurality of binding molecules, each binding molecule specifically binding to a complementary target of the plurality of targets, a plurality of encoding polynucleotides, each encoding polynucleotide specifically binding to each polynucleotide of the plurality of substrate polynucleotides attached to the substrate, at least one a scaffold molecule configured to bind to the each binding molecule of the plurality of binding molecules and each encoding polynucleotide of the plurality of the encoding polynucleotides with positionally distinguishable scaffold binding domains, the positionally distinguishable scaffold binding domains being arranged on the scaffold molecule to allow, upon binding with the at least one binding molecule and with the encoding polynucleotide, presentation of the at least one binding molecule for specific binding to the target and of the encoding polynucleotide for specific binding to the substrate polynucleotide.

According to a fourth aspect, a scaffold molecule is described, the scaffold molecule comprising a first scaffold binding domain configured to attach at least one binding molecule and a second scaffold binding domain configured to attach an encoding polynucleotide, wherein the at least one binding molecule is configured to specifically bind to a target and the encoding polynucleotide is configured to specifically bind to a substrate polynucleotide attached to a substrate. In the scaffold molecule, the first scaffold binding domain and the second scaffold binding domain are positionally distinguishable and arranged in the scaffold molecule to minimize interaction of the at least one binding molecule and the encoding polynucleotide, upon binding of the at least one binding molecule with the first binding domain and of the encoding polynucleotide with the second binding domain.

According to a fifth aspect, a polynucleotide encoded capture agent is described. The polynucleotide encoded capture agent is comprised of a binding molecule that specifically binds to a target and of an encoding-polynucleotide attached to the binding molecule. The encoding polynucleotide is comprised of a sequence that specifically binds to a substrate polynucleotide. The substrate polynucleotide is attached to a substrate and is comprised of a sequence that specifically binds to the encoding polynucleotide. In the polynucleotide encoded capture agent, the encoding polynucleotide comprises at least one restriction enzyme site arranged in the encoding polynucleotide to be presented for cleavage by a corresponding restriction enzyme. In several embodiments, the polynucleotide encoded capture agent can be a modular polynucleotide encoded capture agent herein described.

According to a sixth aspect, the substrate of each of the methods, systems and arrays disclosed herein is in operable association with a microfluidic component comprising a microfluidic feature for carrying a fluid. Accordingly, in the methods herein described, at least contacting the encoding-polynucleotide with the substrate polynucleotide can be performed in the fluid carried by the microfluidic feature. Additionally, each of the systems herein disclosed can further include the microfluidic component comprising the microfluidic feature.

In modular polynucleotide-encoded capture agents, and related arrays methods and systems, herein described, the target binding structure is decoupled from a scaffold structure, thus allowing an improved flexibility and versatility of use if compared with corresponding instruments of the art.

Additionally, modular polynucleotide-encoded capture agents, and related arrays methods and systems herein described allow, in several embodiments, to attach to a single polynucleotide-encoded capture agent a plurality of binding molecules, in particular proteins, each binding a same target. Accordingly, the sensitivity and/or selectivity of the resulting modular polynucleotide encoded capture agent can be controlled and, in particular, improved.

In particular, modular polynucleotide-encoded capture agents, and related arrays, methods and systems herein described allow, in several embodiments, an improved selectivity and sensitivity of target detection when compared to certain methods and systems of the art.

More particularly, modular polynucleotide-encoded capture agents, and related arrays, methods and systems herein described allow, in several embodiments, to detect and/or sort of targets such as cells for which only low-affinity ligands exist, and targets such as cells for which ligands are present in very low abundance <<0.1% even from a complex mixture.

Modular polynucleotide-encoded capture agents, and related arrays, methods and systems herein described also allow, in several embodiments, to perform target detection using a robust platform which does not necessarily include antibodies.

In particular, modular polynucleotide-encoded capture agents, and related arrays, methods and systems herein described allow, in several embodiments, to generate robust and modular arrays for high efficiency target detection and/or sorting, which, in view of their stability are capable to significantly outperform literature approaches that utilize surface-bound proteins for target capture and detection.

Furthermore, modular polynucleotide-encoded capture agents, and related arrays methods and systems, in several embodiments allow selective release of the polynucleotide encoded capture agent-target complex, and therefore allow for the deployment of a host of bioanalytical methods on detected and/or sorted targets, with particular reference to target cells.

The modular polynucleotide-encoded capture agents, and related arrays methods and systems herein described can be used in connection with performance of several assays designed to detect and/or sort targets, which include, but are not limited to, monoparameter and multiparameter assays such as genomic and proteomic assays, and other assays identifiable by a skilled person. In particular, the modularity of the platform herein described allows performance on captured target (and in particular of captured cell) of standardized assays traditionally performed on glass substrates, such as immunohistochemistry, FISH, and additional assays identifiable by a skilled person upon reading of the present disclosure.

The modular polynucleotide-encoded capture agents, and related arrays methods and systems herein described can be used in various fields including but not limited to molecular diagnostics, molecular therapeutics, fundamental biological studies, tissue engineering, and biomaterials, The details of one or more embodiments of the disclosure are set forth in the accompanying drawings and the description and examples below. Other features, objects, and advantages will be apparent from the description, examples and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 6 shows results of cell sorting experiments performed using modular polynucleotide-encoded capture agents according to an embodiment herein described. Panel A shows a grayscale version of a fluorescence image of ssDNA-SA-p/MHC tetramer arrays specific for Tyrosinase TRC contacted with a complementary substrate polynucleotide and T cells at different frequencies as indicated. Panel B shows a diagram illustrating a quantification of the data shown in Panel A.

FIG. 9 shows results of experiments exemplifying the capture efficiency of modular polynucleotide encoded capture agent according to an embodiment herein described. Panel A shows grayscale brightfield images of arrays of ssDNA encoded proteins including a streptavidin scaffold and p/MHC binder proteins specific for Human TCR transduced T cells (left) and Murine TCR transgenic T cells (right). Each sub-panel of Panel A, shows the brightfield image of an array after contact of the ssDNA-encoded protein with a complementary substrate DNA and with a specific cell as indicated. Panel B shows grayscale brightfield images of arrays of ssDNA-encoded proteins including an optimized streptavidin scaffold and p/MHC binder proteins specific for Human TCR transduced T cells (left) and Murine TCR transgenic T cells (right) (cells identical to top panel). Each sub-panel of Panel B shows the brightfield image of an array after contact of the SAC-ssDNA p/MHC with a complementary substrate DNA and with the specific cells as indicated.

FIG. 14 shows diagrams illustrating detection specificity and sensitivity of modular polynucleotide-encoded capture agents according to an embodiment herein described. Panel A shows diagrams illustrating quantity and specificity of human CD8+ T cell that are specific for EBV BMLF1$_{259\text{-}267}$, as determined by flow cytometry. Panel B shows diagrams illustrating quantity and specificity of human CD8+ T cell that are specific for CMV pp65$_{495\text{-}503}$, as determined by flow cytometry.

FIG. 17 shows fluorescently labeled ssDNA-p/MHC tetramers can be utilized as staining reagents for flow cytometry and can localize antigen-specific T cells from suspension by DNA hybridization. In panel a, Cy3-labeled A'-SAC conjugates were used to generate fluorescent tyrosinase368-376 ssDNA-p/MHC tetramers and used to detect Jurkat$^{\alpha\text{-}Tyr}$ cells by flow cytometry. Similar staining profiles were observed between Cy3 NACS p/MHC tetramer (lower panels) and conventional tyrosinase368-376(PE) p/MHC tetramers (upper panels). In panel b, Jurkat$^{\alpha\text{-}Tyr}$ cells were stained with tyrosinase368-376-A' p/MHC tetramers prior to exposure to a DNA array. The Jurkat$^{\alpha\text{-}Tyr}$ cells were localized to spot A by DNA hybridization.

DETAILED DESCRIPTION

Figure 1:
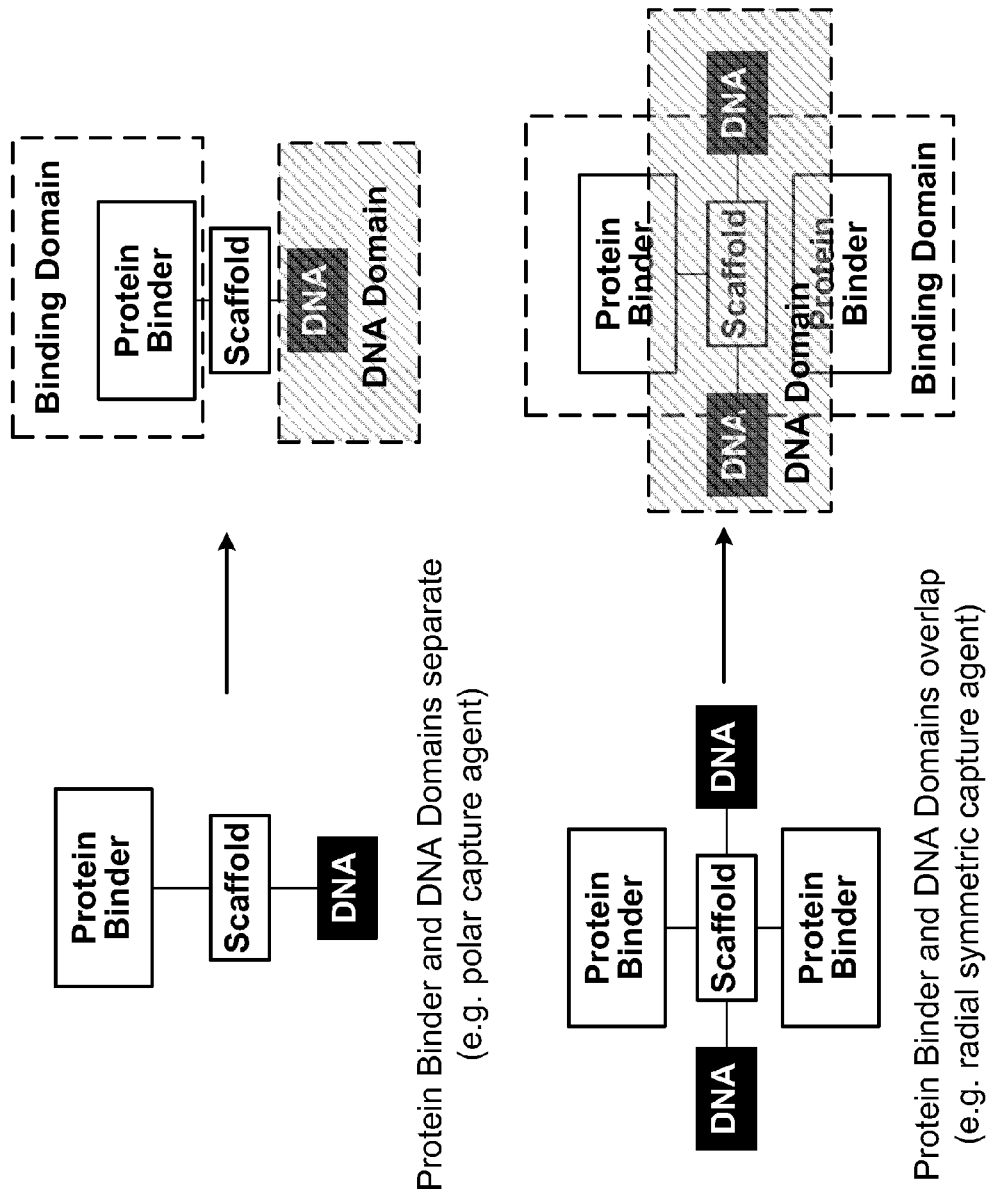
FIG. 1 shows a schematic illustration of a modular polynucleotide encoded capture agent, according to embodiments herein disclosed.

Polynucleotide encoded capture agents and in particular modular polynucleotide encoded capture agents and related arrays methods and systems are herein described, which can be used in combination with substrate polynucleotides to detect one or more targets in a sample, according to an approach herein also identified as NACS approach or technology.

The wording "polynucleotide-encoded capture agent" refers to a polynucleotide encoded molecular construct that specifically binds to a target. In particular, a polynucleotide-encoded capture agent typically comprises a binding component that specifically binds to, and is thereby defined as complementary to, the target, a structural component that supports the binding component and an encoding polynucleotide attached to the structural component that encodes the molecular structure.

In a "modular polynucleotide-encoded capture agent" the binding component, the structural component and the encoding component of the polynucleotide encoded capture agent are formed by standardized molecular units that can be coupled or decoupled to each other in a controlled fashion. In particular, in the modular polynucleotide-encoded capture agents herein described, the binding component is formed by at least one binding molecule, that is configured to specifically bind to, and be thereby defined as complementary to, a target; the encoding component is formed by an encoding polynucleotide configured to specifically bind, and be thereby defined as complementary to, a substrate polynucleotide attached to a substrate; and the structural component is formed by a scaffold molecule attaching the at least one binding molecule and the encoding polynucleotide. In particular, in the modular polynucleotide-encoded capture agents, the at least one binding molecule specifically binding to a target, the scaffold molecule and an encoding polynucleotide, are attached or to be attached one to the other according to the schematic illustration of FIG. 1 or FIG. 2 as will also be further described herein below.

The term "attach" or "attached" as used herein, refers to connecting or uniting by a bond, link, force or tie in order to keep two or more components together, which encompasses either direct or indirect attachment such as, embodiments where a first molecule is directly bound to a second molecule or material, and embodiments wherein one or more intermediate molecules are disposed between the first molecule and the second molecule or material. Molecules include but are not limited to polynucleotides, polypeptides, and in particular proteins and antibodies, polysaccharides, aptamers and small molecules.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base, and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length DNA RNA analogs and fragments thereof. A polynucleotide of three or more nucleotides is also called nucleotidic oligomers or oligonucleotide.

The term "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer or oligopeptide. As used herein the term "amino acid", "amino acidic monomer", or "amino acid residue" refers to any of the twenty naturally occurring amino acids including synthetic amino acids with unnatural side chains and including both D an L optical isomers. The term "amino acid analog" refers to an amino acid in which one or more individual atoms have been replaced, either with a different atom, isotope, or with a different functional group but is otherwise identical to its natural amino acid analog.

The term "protein" as used herein indicates a polypeptide with a particular secondary and tertiary structure that can participate in, but not limited to, interactions with other biomolecules including other proteins, such as antibodies, DNA, RNA, lipids, metabolites, hormones, chemokines, and small molecules.

The term "antibody" as used herein refers to a protein that is produced by activated B cells after stimulation by an antigen and binds specifically to the antigen promoting an immune response in biological systems and that typically consists of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". A polyclonal antibody refers to a mixture of monoclonal antibodies with each monoclonal antibody binding to a different antigenic epitope. Antibodies can be prepared by techniques that are well known in the art, such as immunization of a host and collection of sera (polyclonal) or by preparing continuous hybridoma cell lines and collecting the secreted protein (monoclonal).

The term "polysaccharide" as used here indicates polymers formed by monosaccharides units joined together by glycosidic bonds. Polysaccharides include very large, often branched, macromolecules, including polymers of any length, from a mono- or di-saccharide polymer to polymers including hundreds or thousands of monosaccharides and that can have a molecular weight from about 1000 Da to about 20 KDa. Exemplary polysaccharides comprise glycogen, cellulose, starch, and chitin.

The term "aptamers" as used here indicates oligonucleic acid or peptide molecules that bind a specific target. In particular, nucleic acid aptamers comprise nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range).

The term "small molecule" as used herein indicates an organic compound that is not a polymer and has a dimension from about 10 Da to 2000-3000 Da. Small molecules comprise molecule that are biologically active and molecules that do not have a biological activity. Exemplary small molecules comprise 4-[(4-methylpiperazin-1-yl)methyl]-N-[4-methyl-3-[(4-pyridin-3-ylpyrimidin-2-yl)amino]-phenyl]-benzamide (Gleevec®), Sulfosuccinimidyl-6-(biotinamido)hexanoate, and Succinimidyl 6-hydrazinonicotinate acetone hydrazone.

In the modular polynucleotide capture agents herein described, the at least one binding molecule specifically binds to a target, and the encoding polynucleotide specifically binds to a substrate polynucleotide attached to a substrate.

The wording "specific", "specifically", or specificity" as used herein with reference to the binding or attachment of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence.

The wording "substrate polynucleotide" as used herein refers to a polynucleotide that is attached to a substrate so to maintain the ability to bind to its complementary polynucleotide. A substrate polynucleotide can be, in particular, comprised of a sequence that specifically binds and is thereby defined as complementary with an encoding-polynucleotide of a polynucleotide encoded protein.

The term "substrate" as used herein indicates an underlying support or substratum. Exemplary substrates include solid substrates, such as glass plates, microtiter well plates, magnetic beads, silicon wafers and additional substrates identifiable by a skilled person upon reading of the present disclosure.

In some embodiments, the encoding polynucleotide attached to the scaffold component is specific for the binding component. Those embodiments can be used to perform assays that exploit the binding component-target specific interaction to detect proteins, cytokines, chemokines, small molecules, DNA, RNA, lipids, etc., whenever a target is known, and sensitive detection of that target is required. In several embodiments, the binding component and the structural component are formed by a protein.

The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, aminoacids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

In several embodiments, the modular polynucleotide-encoded molecule comprises at least one binding molecule, a scaffold molecule and an encoding polynucleotide.

The term "binding molecule" or "affinity agent" as used herein indicates a molecule that is able to specifically bind to a target under appropriate conditions. The binding molecule or affinity agent is, in particular, able to specifically bind to at least one target under appropriate conditions, which includes for example binding to the target in a solution (e.g. biologically derived, or synthetic), on a cell surface, on artificial surfaces (e.g. derivatized beads, nanoparticles) or in other mixtures or surfaces identifiable by a skilled person. Examples of binding molecules include any molecule that exhibits a binding affinity for a predetermined target, including but not limited to protein binders such as antibodies, lectins, Fc receptors, MHC protein A/G, peptide aptamers etc, non-protein binders such as polynucleotides (e.g. RNA e/o DNA) nucleic acid aptamers, peptides, small molecules, and drugs such as imatinib mesylate (Gleevac®), bungarotoxins, inhibitor for nicotinic acetylcholine receptors etc,. In the modular polynucleotide encoded capture agent, the affinity agent is attached to the scaffold where the binding can be performed directly or indirectly, e.g. through an intermediate molecule (e.g. a biotin molecule), through any covalent attachment scheme (readily identified by a person in the field) or through non-covalent schemes such as electrostatic, Fc-protein A/G interaction, biotin etc.

Typically, a binding molecule used in the modular polynucleotide-encoded protein herein described, exhibits a binding affinity and binding selectivity to a target to be detected that can be measured with technologies known in the art, such as surface Plasmon resonance (SPR), enzyme linked immunosorbant assays (ELISAs), and additional techniques identifiable by a skilled person. The choice of a binding molecule for a modular polynucleotide capture agent is made by a skilled person in view of the target to be detected and the experimental design. For example, when the target is a cell, the binding molecule exhibits a binding affinity and selectivity to biomolecules, and in particular biomarkers, that are presented at the surface of specific cell types. Exemplary surface molecules include but are not limited to membrane proteins, receptors, glycoproteins, ion channels or major histocompatibility complexes and other molecules identifiable by a skilled person upon reading of the present disclosure.

A skilled person would also be able to identify an appropriate binding molecule for a certain target based on determination of the binding affinity and selectivity exhibited by candidate binding molecules towards the target and in view of the number of binding molecules that are attachable to the scaffold (see below).

In several embodiments, upon selection of the appropriate scaffold, it is possible to modulate the number of binding molecules to be attached to the scaffold to achieve a desired binding affinity and/or selectivity by controlling the valency of the capture agent for the target (i.e. the number of chemical bonds formed by a capture agent with the target).

For example, a binding molecule with low affinity (e.g., $Kd>10^{-6}$) for a certain target (e.g., a cell) will most likely require an increased number of molecules attached to the scaffold to ensure specific binding of the modular polynucleotide-encoded capture agent that comprises such a binding molecule.

Accordingly, in several embodiments, the binding affinity of the capture agents for a certain target can be controlled and, in particular, increased by providing multiple copies of a same or different binding molecule. In particular, multiple copies of a same or different binding molecule, if located appropriately on the scaffold, can lend the binding molecule/ scaffold construct a significantly higher binding affinity to the cell type of interest, than can the affinity agents by themselves.

In particular, multiple ligand capture agents can be assembled by combining various binding molecules (such as the ones listed above) to the same scaffold. This may be advantageous in certain situations when it is desirable to probe multiple elements that are present within a target sample (for example, multiple cell surface markers, endogenous and exogenous peptide/MHC from the same antigen presenting cell, etc).

In several embodiments, the binding molecule is a protein, such as antibodies, lectins, Fc receptors, MHC, protein A/G, and additional proteins identifiable by a skilled person.

In particular, in some embodiments, the binding molecule is an antibody. In particular, in those embodiments, the antibody can be produced that specifically bind to a desired target. The target can be a biomarker to be detected in a mixture or on a cell surface (see e.g. CD4, CD8, and CD3). In the latter cases, the antibodies can also be used as binding molecules of modular polynucleotide encoded capture agent used to detect and/or sort cell targets (see Example 13).

In some embodiments, the protein can be an MHC complex. The term "MHC" or "p/MHC" as used herein indicates peptide major histocompatibility complex molecules (p/MHC), and, more particularly, heterotrimer protein binders that are the cognate binders to T cell receptors found on T cells. In particular, p/MHC complexes are hetero-trimeric proteins found on the cell surface of antigen presenting cells and comprise MHC class I, MHC class II and MHC class III proteins. MHC class I proteins contain a peptide, an a chain and β2-micro-globulin. APCs expressing MHC class I proteins present antigen fragments to cytotoxic T-cells, stabilized by the surface molecule CD8. MHC class II including heterodimeric peptide-binding proteins and proteins that modulate antigen loading onto MHC class II proteins in the lysosomal compartment such as MHC II DM, MHC II DQ, MHC II DR, and MHC II DP. On antigen-presenting cells, MHC class II proteins contain a & β chains and they present antigen fragments to T-helper cells by binding to the TCR and the CD4 receptor on the T-helper cells. MHC class III comprise other immune components, such as complement components (e.g., C2, C4, factor B) and some that encode cytokines (e.g., TNF-a) and also hsp.

A typical receptor/target for MHC is the T cell receptor found on T cells that can be specific for various antigens (e.g. MART-1, Cytomegalo virus, Tyrosinase etc) as presented in the MHC complexes. The appropriate MHC for a specific target can be identified by a skilled person based on the target of interest in view of the binding specificity MHC candidate molecules.

In some embodiments, MHC monomers provide the binding molecule of the modular polynucleotide-encoded capture agent herein described. In those embodiments, the targets are preferably provided by molecular biomarker or other molecules in a state or form when they are not comprised within a cell to be detected. In some embodiments, MHC dimers and trimers can be utilized to detect antigen-specific T cells in solution via flow cytometry. In some embodiments, MHC dimers and trimers with higher affinity interactions (e.g. TCR-p/MHC), are expected to detect antigen specific T cells also in a complex environment, as exemplified in Example 5 and FIG. 9a (lower left panel) where the Jurkat cells expressing a TCR against tyrosinase antigen were sorted with a suboptimal capture agent (see also the mix of dimers and trimers, of FIG. 8) In some embodiments, MHC tetramers are used in connection with a polynucleotide encoded scaffold and can be advantageously used in applications directed to cell detection and/or sorting. (e.g. see Examples 9 and 10 and FIGS. 5, 6, 9, 10, 11, 12, and 13-14, 15, 16, 19, 22.)

In particular, in some embodiments, a tetramer of an antigen-presenting MHC provides the binding molecule of a modular polynucleotide encoded capture agent herein described. MHC tetramers exhibit a substantially higher affinity for a T-cell of interest than MHC monomers or dimers do, and are now well-established reagents for the detection of antigen-specific T cells by flow cytometry. When coupled with a scaffold in the modular capture agents herein disclosed an MHC tetramer allows detection and/or sorting of target with an increased sensitivity and specificity when compared with some methods known in the art.

In the following disclosure, including figures and examples, reference will often be made to MHC whenever discussing properties and use of a binding molecule in connection with the modular polynucleotide-encoded molecules herein disclosed. A skilled person would be able to adapt the description to making and using of proteins and other molecules other than MHC. In particular, the skilled person will appreciate that, when using binding proteins other than p/MHC molecules, the main determinant of the choice is the target to be detected. For example, if it is desirable to detect a small molecule (e.g. caffeine), and an aptamer exists that is specific for caffeine, then the skilled person will choose the aptamer as the binding portion and adapt it to the scaffold construct. (see Example 13)

The term "scaffold" or "scaffold molecule" as used herein indicates a molecular structure of a capture agent that serves to assemble an affinity agent (e.g., MHC) to an encoding polynucleotide (e.g., ssDNA tags). This structure can be derived from proteins (such as Streptavidin or SA), other biopolymers (such as polynucleotides, like RNA and DNA, peptide nucleic acid, etc.), or other polymers which can bind to the affinity agent and the encoding polynucleotide in distinct and separate portions of the polymer.

In modular polynucleotide encoded capture agents here described, the scaffold molecule is configured to bind the at least one binding molecule and an encoding polynucleotide, with scaffold binding domains.

The term "domain" as used herein with indicates a region that is marked by a distinctive structural and functional feature. In particular, a scaffold binding domain is a region of the scaffold that is configured for binding with another molecule. Accordingly, a scaffold binding domain in the sense of the present disclosure includes a functional group for binding the another molecule and a scaffold binding region on the scaffold that is occupied by the another molecule bound to the scaffold. Once the functional group has been identified, the relevant scaffold binding region can be determined with techniques suitable to identify the size and in particular the largest diameter of the another molecule of choice to be attached. The average largest diameter for a protein according to the present disclosure in several embodiments is between about 10 Å and about 50 Å depending on the protein of choice, between about 3 Å and about 10 Å for a small molecule, and is between about 10 Å and about 20 Å for a polynucleotide. Techniques suitable to identify dimensions of a molecule include but are not limited to X-ray crystallography for molecules that can be crystallized (see e.g., Refs. 39-41) and techniques to determine persistence length for molecules such as polymers that cannot be crystallized (see e.g., Refs. 42-43). Those techniques for detecting a molecule dimensions are identifiable by a skilled person upon reading of the present disclosure.

In the modular polynucleotide encoded capture agent herein described, the scaffold binding domains are positionally distinguishable among each other, and therefore, do not overlap.

The wording "positionally distinguishable" as used herein refers to molecules or domains thereof, indicates molecules or domains thereof that are distinguishable based on the point or area occupied by the molecules or domains. Accordingly, positionally distinguishable scaffold binding domains are binding domains that occupy different points or areas on scaffold and are thereby positionally distinguishable.

In particular, in modular polynucleotide encoded capture agents here described, the scaffold molecule comprises a first scaffold binding domain that is configured to attach at least one binding molecule and a second scaffold binding domain that is configured to attach the encoding polynucleotide.

In the modular polynucleotide encoded capture agents, the first scaffold binding domains and the second scaffold binding domains can be selected by identifying positionally distinguishable functional groups and related scaffold binding regions that are configured, to allow, upon attachment, that the attached molecule is presented on the scaffold.

The term "present" as used herein with reference a molecule or portion thereof, (e.g., a functional group or a restriction site) that has a chemical reactivity and is comprised in a structure, indicates a configuration of the molecule or functional group in the structure wherein the molecule or portion thereof maintains a detectable level of such chemical reactivity. Accordingly, a molecule or a functional group presented on a scaffold is a molecule or portion thereof comprised in that scaffold in a configuration that allows performing, and detecting, under the appropriate conditions, the one or more chemical reactions that chemically and/or biologically characterize the molecule or portion thereof at issue.

Therefore in modular polynucleotide encoded capture agents of the present disclosure, upon attachment of the binding molecule and the encoding polynucleotide with the scaffold, the binding molecule is presented for binding to the target and the encoding polynucleotide is presented for binding to a substrate polynucleotide.

In modular polynucleotide encoded capture agents here described, presentation of the binding molecule and encoding polynucleotide on the scaffold is achieved by selecting a scaffold with appropriate first and second scaffold binding domains.

Functional groups for binding a binding molecule, that can be included in a first scaffold binding domain, depend on the chemical nature of the binding molecule and are identifiable by the skilled person upon reading of the present disclosure. For example, functional groups for binding a binding molecule include but are not limited to BirA Ligase (enzyme that attaches biotin group to predefined peptide sequences), other enzymes such as formylglycine-generating enzyme (site-specific introduction of aldehyde groups into recombinant proteins described for example in Ref. 44).

Functional groups for binding a polynucleotide, that can be included in a second scaffold binding domain, are also identifiable by the skilled person upon reading of the present disclosure. Exemplary functional groups presented on the scaffold for binding a polynucleotide include functional groups such as sulfulhydryl (e.g. in a cysteine residue), primary amines and other functional groups that attach derivatized DNA via conventional conjugation strategies, that would be identifiable by the skilled reader.

Those functional groups can either be endogenous groups on the scaffold (e.g. native lysine residues on a scaffold protein), or introduced by methods such as gene cloning (e.g. proteins), synthetic techniques (polymers, small molecules), and other methods. The number of copies of polynucleotides or binding molecules that can attach to the scaffold will be directly proportional to the number of functional groups available on the scaffold.

The specific first and second functional groups and related scaffold binding domain are selected in view of the experimental design. Usually, the scaffold is selected so that the functional groups of the first and second scaffold binding regions allow attachment of the binding molecule and the encoding polynucleotide using orthogonal chemistries. A set of attachment chemistries is orthogonal if, when performing any particular chemistry, the functional groups that participate and/or undergo a chemical reaction in that particular chemistry do not react with any other chemistry within the orthogonal set. Exemplary orthogonal chemistries include cysteine-maleimide coupling, amine-NHS coupling, and streptavidin-biotin binding, when a scaffold is a protein, and controlled oxidization of OH functional groups in different scaffold binding regions with $NaIO_4$ when the scaffold is a polysaccharide.

In some embodiments, in addition to containing distinct scaffold binding domains to accommodate the affinity agent and encoding DNA, the scaffold is also selected to be compatible with the environment of the target of interest (e.g. it should be soluble in aqueous solutions if the target is cell surface markers).

In several embodiments, the scaffold consists of a macromolecular scaffold that is customized, via multi-ligand interactions, for the high affinity binding to specific cell types, and then for the spatially directed, multiplexed sorting of those different cell types.

In particular, in some embodiments, the scaffold is provided by a non-naturally occurring molecule that is expressed with modular design characteristics. In those embodiments, the protein scaffold is designed so that multiple and controlled numbers of copies of specific binding molecules and encoding polynucleotides may be attached to the scaffold at specific scaffold polynucleotide binding domains.

In some embodiments, the scaffold can be configured to enable or ease attachment of multiple copies of single-stranded encoding polynucleotide (e.g. DNA oligomers) in multiple second scaffold binding domains. In those embodiments, the second scaffold binding domain can be selected to allow hybridization with an encoding polynucleotide to be used to spatially direct the scaffold to particular spots on a surface that are coated with the substrate polynucleotides.

A scaffold, thus configured, can be useful, in embodiments where the modular polynucleotide-encoded capture agents is used for the spatially selective sorting of specific cell types. For example, multiple scaffolds, each containing a different set of affinity agents, and uniquely labeled with bindingly distinguishable ssDNA oligomers, can be harnessed in parallel to spatially separate a mixture of many cell types into its individual components as it will be apparent to a skilled person in view of the present disclosure. For example, in some embodiments, it is feasible to use modular capture agents with biotinylated-antibodies along with p/MHC proteins as the affinity reagents, where each is encoded to bindingly distinguishable ssDNA oligomers. The antibodies can be used to sort cells according to cell surface markers like CD4, CD8, CD3, etc., while the p/MHC proteins will sort cells according to antigen-specificity as determined by the TCRs.

In some embodiments, a desired configuration of a scaffold and, in particular, a scaffold protein, can be achieved through modification of candidate scaffolds that are modified with techniques known to the skilled person such as traditional cloning techniques or other techniques identifiable by a skilled person.

In some embodiments, the scaffold can be optimized for a specific capture agent. In particular, in a specific capture agent an optimized scaffold has well defined scaffold binding regions for independently coupling a binding molecule and an encoding-polynucleotide, so that upon binding the binding molecule and the encoding polynucleotide, possible interferences between the polynucleotide and the assembly of the binding molecule are minimized This is usually achieved for a capture agent having a desired binding affinity for the target and the substrate polynucleotide, by minimizing structural overlapping between the binding molecule(s) and the encoding polynucleotide attached to the scaffold while maintaining a desired binding affinity of the capture agent for the target and the substrate polynucleotide.

Figure 2:
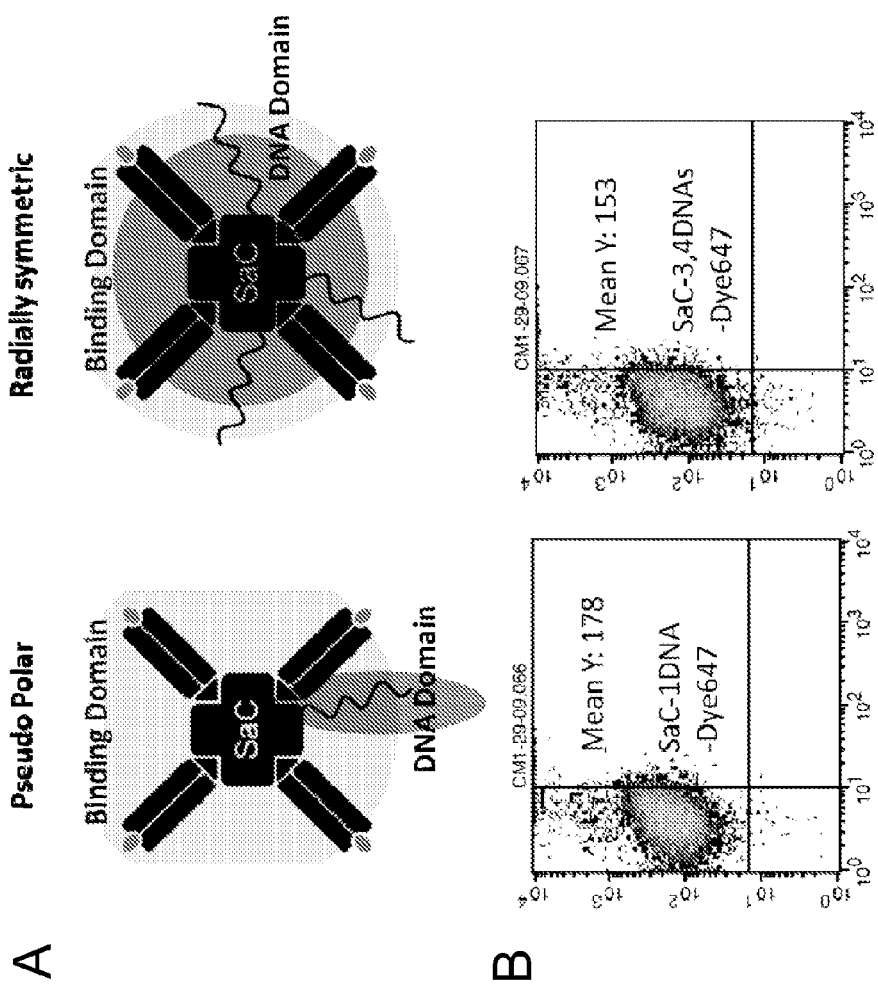
FIG. 2 shows a schematic illustration of a modular polynucleotide encoded capture agent, according to embodiments herein disclosed.

Reference is made to FIGS. 1 and 2 showing different configurations of the modular capture agents according to the present disclosure. In particular, in the illustration of FIGS. 1 and 2 a scaffold domain, a binding molecule domain (protein binder domain) and a polynucleotide domain (DNA domain) are schematically illustrated. As already mentioned, the term "domain" as used herein with indicates a region that is marked by a distinctive structural and functional feature. Accordingly, the term "domain" as referred to the scaffold molecule, the binding molecule and the encoding polynucleotide, indicates a special region defined by conformational changes of the molecule (scaffold molecule, binding molecule, polynucleotide) bound in a capture agent at a certain temperature. The domain of a certain molecule can be determined with any techniques suitable to identify the dimension and in particular the tri-dimensional structure a molecule, and include X-ray crystallography, size exclusion chromatography, mass spectrometry, gel electrophoresis and other techniques identifiable by a skilled person.

In an optimized scaffold for a certain capture agent, the scaffold binding domains are selected to minimize the overlapping between the binding molecule domains and the polynucleotide domains on the scaffold, that provide the desired binding affinity to the capture agent.

In several embodiments, an optimized scaffold presents the binding molecules and encoding polynucleotides associated to a desired binding affinity of the resulting capture agent on all the available positionally distinguishable scaffold binding domains on the scaffold. On the other hand, in several embodiments, a non-optimized scaffold the number of attached binding molecule and encoding-polynucleotides does not match the total number of sites available on the scaffold. For example, if the scaffold has 4 sites to attach binder proteins and 3 sites to attach DNA, most likely the non-optimized scaffold will be able to contain <4 binder protein and <3 DNA per scaffold, regardless of how large the molar excess is. This presence (or absence) of the binding molecule and/or polynucleotide per scaffold can be measured (see for example FIG. 8). The capture agent can also be tested with traditional assays like ELISA, flow cytometry, SPR, etc. to measure the efficacy of the capture agent.

In a specific capture agent, the scaffold can also be modified to optimize the scaffold function as an integration point for two moieties (i.e. the binding molecule, and the encoding-polynucleotide), while minimizing any possible interactions between the scaffold domains that bind those moieties which would result in a reduced functional efficacy of the attached moiety. The reduced functional efficacy can be due to steric hindrance (between overlapping regions of the binding molecule and encoding-polynucleotide), irreversible modification of the attachment regions on the scaffold due to the nature of the coupling chemistry employed, etc. A comparison between T cell capture efficiency with an unoptimized scaffold (native SA) and an optimized scaffold (cysteine-SA) is illustrated in Examples 4-6 and FIGS. 7-9).

Accordingly a certain scaffold molecule binding a certain binding molecule and encoding polynucleotide can be optimized for those binding molecule and encoding polynucleotide by identifying the scaffold binding regions binding the binding molecule and encoding polynucleotide and modify the remaining portion of the scaffold molecule to arrange the scaffold binding domains on the scaffold to minimize interactions between the binding molecule and the encoding polynucleotide. In this way, it is possible to derive optimized variants of a certain scaffold molecule.

In some embodiments the scaffold is a protein. In particular in some embodiments, protein scaffolds are provided which already contain functional groups that allow specific binding for the binding molecule. For example, streptavidin is a good scaffold protein because of its natural affinity for biotin, giving it specificity for biotinylated p/MHC molecules. Another example would be protein A/G. These proteins have a natural affinity for the Fc region of antibodies, in which the latter would be employed as the binding protein. This is advantageous over protein scaffolds in which no inherent specificity exists, in which case it is necessary to introduce two chemically orthogonal handles for coupling the binding protein and the encoding-polynucleotide. Since most proteins lie within a narrow range of size and sequence length (i.e. properties such as solubility, number of available sites for modification), it is expected that any protein can be used as a scaffold molecule. In particular, proteins which are stable in the conditions used for bioconjugation are in particularly expected to be suitable as scaffolds.

In several embodiments, the scaffold protein is formed by a streptavidin (SA or Sa). Streptavidin is a tetrameric protein from the bacterium Streptomyces avidinii having sequence HMGITGTWYNQLGSTFIVTAGADGALTG-TYESAVGNAESRYVLT GRYDSAPATDGSGT ALG-WTVAWKNNYRNAHSATTWSGQYVGGAE-AMNTQWLLT SGTTEANAWKSTLVGH DTFTKVKPSAAS (SEQ ID NO: 1). SA has extraordinary affinity and four unique binding sites, arranged tetrahedrally for its natural ligand biotin (Kd$^{-10-15}$ mol/L). The molar binding capacity of Streptavidin for biotin is 4:1 biotin:SA. While SA does not have to specifically bind to the binding molecule (e.g. via biotin interaction), embodiments where alternative coupling methods are used to bind the binding unit to SA do not take advantage of the 4 fold valency and strong interaction of SA for biotin. Specifically in several embodiments where SA is the scaffold, the C terminus portion is chosen as the site for attachment of the encoding polynucleotide in view of the location of the binding pocket for biotin on the N-terminus portion of the protein.

Accordingly, in several embodiments where the scaffold protein is streptavidin, binding molecules (e.g. MHC molecules) can be biotinylated, to enable the tetrameric assembly with the protein-ligand pair SA. In some embodiments, binding molecules can also be coupled to SA via covalent linkages (such as amide coupling), and therefore not necessarily through the biotin-SA interaction. The skilled person will be able to identify the most appropriate binding based on the experimental design of choice. In several embodiments of the present disclosure, SA is used as standard scaffold used to assemble p/MHC monomers into tetramers.

In embodiments where the scaffold is SA, a modified SA can be used as well as molecules derived therefrom (see in particular SA-phycobiliprotein (PE or APC) conjugates). In some embodiments, a scaffold can be used that is a recombinant mutant of SA for fluorescent p/MHC tetramer preparations. In some of those embodiments, SA variants can be used, such as for example a variant that incorporates a cysteine residue at the carboxy-terminus [Ref 25, 26, 27], in a site removed from the biotin binding pocket. In those embodiments, the conjugation of cysteine-reactive maleimide derivatives can be restricted to the C-terminus because cysteine residues are absent in native SA.

More particularly, in some embodiments, an optimized Streptavidin, named streptavidin-cysteine (SAC), can be used that contains several exogenous amino acids at the c-terminus. These residues contain a cysteine amino acid, from which derivatized DNA (or any other maleimide-derivatized molecule) can be coupled to. The SAC scaffold has the sequence HMGITGTWYNQLGSTFIVTAGADGALTG-TYESAVGNAESRYVLTGRYDSAPATDGSGT ALG-WTVAWKNNYRNA HSATTWSGQYVGGAE-AMNTQWLLTSGT TEANAWKSTLVGH DTFTKVGGSGCP (SEQ ID NO: 2)

In the present disclosure, reference is often made to SA and SAC scaffold. A skilled person will be able to adapt the description to scaffolds and optimized scaffold other than SA and SAC, making also reference to the guidance provided by the examples section. In particular additional scaffold proteins include but are not limited to Protein A/G, branched peptides, small molecules such as NHSester PEG-malemide and optimized variants thereof.

Additional scaffolds and optimized scaffolds, given a predetermined target and pre-selected binding molecule can be derived using the following approach. (a) selecting a first coupling chemistry to attach the preselected binding molecule to the scaffold, and a second coupling chemistry to attach the polynucleotide to the scaffold (e.g. NHS-amine and thiol-maleimide chemistry). (b) selecting a candidate scaffold structure, considering the valency and polarity of the resulting capture agent (e.g. the use of branched peptides for increasing valency, the use of glycine-serine-glycine-serine extensions for creating space between the binder proteins). (c) performing coupling of the polynucleotide and of the binding molecule with candidate scaffold structure thus providing a candidate capture agent. (d) testing the candidate capture agent for specific binding with the predetermined target empirically and optionally (e) iterate some or all the steps if necessary or desired to increase binding affinity and/or specificity of the capture agent to the predetermined target. If optimization is desired the step of selecting a candidate scaffold can be performed or comprise a step of modifying the scaffold to reduce, and in particular, minimize overlapping between the preselected binding molecule and the polynucleotide.

The term "encoding polynucleotide" as used herein indicates a polynucleotide that is attached to the scaffold of a modular capture agent herein described and is complementary to a substrate polynucleotide attached to a substrate. In several embodiments, an encoding polynucleotide encoding a modular capture agent specific for a first target is bindingly distinguishable from an encoding polynucleotide encoding a capture agent specific for a second target, in particular when the first target is different from the second target.

The wording "bindingly distinguishable" as used herein with reference to molecules, indicates molecules that are distinguishable based on their ability to specifically bind to, and are thereby defined as complementary to, a specific molecule. Accordingly, a first molecule is bindingly distinguishable from a second molecule if the first molecule specifically binds and is thereby defined as complementary to a third molecule and the second molecule specifically binds and is thereby defined as complementary to a fourth molecule, with the fourth molecule distinct from the third molecule. Accordingly, a first and second encoding polynucleotides are bindingly distinguishable, if the first encoding polynucleotide specifically binds (and is thereby defined as complementary) to a first substrate polynucleotide and the second encoding polynucleotide specifically binds (and is thereby defined as complementary to) a second substrate polynucleotide, with the first substrate polynucleotide distinct from the second substrate polynucleotide.

In several embodiments of the arrays substrates, methods and systems herein described, each substrate polynucleotide and encoding polynucleotide is bindingly distinguishable from another. In some embodiments of the methods and systems herein disclosed, each substrate polynucleotide of a substrate is sequence specific and positionally distinguishable from another.

As already mentioned, the wording "positionally distinguishable" as used herein refers to with reference to molecules, indicates molecules that are distinguishable based on the point or area occupied by the molecules. Accordingly, positionally distinguishable substrate polynucleotides are substrate polynucleotide that occupy different points or areas on the substrate and are thereby positionally distinguishable.

In several embodiments, the encoding polynucleotide can include one ore more restriction sites for one or more restriction enzymes. The wording "restriction site" indicates specific sequences of nucleotides that are recognized by restriction enzymes. The wording "restriction enzyme" indicates any enzyme that cuts double-stranded or single stranded DNA at specific recognition nucleotide sequences known as restriction sites. Exemplary restriction sites that can be comprised in an encoding polynucleotide herein described include 6 base restriction sites such as the ones for EcoRI BamHI, NdeI and other enzyme identifiable by a skilled person. Additional exemplary restriction site include but are not limited to AvaI, BglII, DraI, EcoRV and further restriction site published in Ref. 45, herein incorporated by reference in its entirety.

In several embodiments, the scaffold is itself interchangeable between bindingly distinguishable capture agents and a single scaffold can be used in the construction of different modular capture agents. Additionally the scaffold can be subject to rounds of improvement and optimization. In several embodiments, the scaffold and at least one binding molecule are also bindingly distinguishable.

In some embodiments, the scaffold can be configured to provide a polar capture agent, with no radial symmetry as shown in the schematic illustration of FIG. 1 (top panel), a symmetrical capture agent as shown in the schematic illustration of FIG. 1 (bottom panel) and FIG. 2 (top right panel), or pseudo-polar capture agent as shown in the schematic illustration of FIG. 2 (top left panel).

In particular, polar capture agents are capture agents where overlapping of the binding molecule domain, scaffold domain and encoding-polynucleotide is minimized Pseudo polar capture agents are molecules in which a minority of binding molecule domains and encoding-polynucleotide domains overlap between each other and with the scaffold domain. In a symmetric capture agent, all the binding molecules and encoding-polynucleotide domains overlap to a certain extent. In each of the polar capture agent, pseudopolar capture agent and symmetric capture agent, the scaffold can be optimized to minimize overlapping within the specific capture agent between the binding molecules domain(s), scaffold molecule domain and the polynucleotide domain(s). Such minimization is maximized for the polar capture agents.

Accordingly, in several embodiments, a fully-assembled, polar, polynucleotide encoded capture agent is expected to have a higher avidity with respect to a non-polar capture agent, since in a polar capture agent the binding molecule is free to interact with the targets of interest, and the encoding polynucleotide is free to interact with the cDNA printed on the substrate. Applicants have demonstrated that an approximation to this "about-face" construct results in higher cell surface marker staining as accessed by flow cytometry (see FIG. 2, lower panels), In particular, Applicants produced SAC-DNA constructs such that 1 DNA strand (fluorescently labeled) were attached per SAC. This moiety is pseudo-polar because the MHC capture proteins (the binding domain) are radially distributed across the scaffold, while the DNA domain is singular (hence polar, when compared to the rest of the construct) (see below). This construct binds better to cell surface receptors when compared directly with radial symmetric constructs (178 vs. 153 mean intensities) (see FIG. 2 lower panels).

In several embodiments, a single scaffold with its associated encoding polynucleotide can be repeatedly used to generate a library of binding structures, by pairing a library of binding structures with the single scaffold. Those embodiments are exemplified in Examples 5, 8, 9 and 10 and in FIGS. 5.6. 9, 12A,B, 13B, 15AB, 16.19.22 where the same scaffold (SAC-A') was used as NACS capture agents with specificity against MART-1, OVA, Pmel, tyrosinase, and CMV. In those embodiments the modularity and interchange-ability of the system.

In some embodiments, polynucleotide encoded capture agents herein described and in particular, modular polynucleotide encoded capture agents here described comprise a variable length linker to be used to couple the binding molecule to the scaffold. The term "linker" as used herein indicates a molecule comprised in the modular polynucleotide encoded capture agents to couple or connect the scaffold with the binding molecule. The linker can be derived from any chemical molecule which can be reacted with the scaffold and the binding molecule of the capture agent that comprises it. Exemplary linkers include but are not limited to peptides (e.g. a 10mer), nucleic acids, polymers (polyethylene glycol), and carbon chains. The length of the linker can be controlled by conventional chemical methods, which should be apparent from a reader with technical expertise. The linker can be attached with conventional bioconjugation strategies which should also be apparent to the skilled reader.

In those embodiments, the inclusion of a linker is expected to increase the degrees of freedom of the binding protein for proper interaction with a target of interest. This is expected to increase the strength of the interaction when the target is fixed/confined in a particular domain where proper spatial orientation is crucial for high affinity interactions (for example, target cell surface proteins confined to the cell membrane).

In some embodiments, the linker can also function as a spacer between the binding molecule and the encoding polynucleotide that is comprised so that the binding molecule domain and the polynucleotide domain do not interfere with each other. Exemplary linkers include molecules of dimensions between 50 Da and 5000 Da.

In some embodiments, further discussed below a linker can be a conditional linker that changes conformation in view of a controlled stimulus.

In some embodiments, the affinity of capture agent for the target can be increased by coupling multiple binding units to a single scaffold. This increase in valency of the capture agent improves the avidity of the assembled complex because each neighbor participates in a binding event, so the net effect is an increase in the overall association of the target with the polynucleotide encoded capture agent as exemplified in Example 5 and FIGS. 7, 8 and 9. This is particularly relevant for binding molecules such as MHC that are characterized by a poor affinity for target cells as monomers but that increase the affinity when bundled together in multimers.

In embodiments where the binding molecule is formed by a low affinity binding protein, increased valency of the capture agent for the target can be required for effectively binding to targets. Variation in affinity associated with a modification of the molecular conformation can be exploited to temporally control, the interaction of polynucleotide encoded molecule to the respective complementary targets. For example, some cell surface receptors function to control cellular activity upon binding to complementary ligands (molecules to which the receptors are specific for). The activity can be reversed or restored when the ligands are no longer bound to the receptors. Thus, by exploiting the decoupled and multivalent nature of the binding molecules to the scaffold, it is possible to control the binding by using conditional linkers—linkers which undergo some conformational change in response to exogenous external stimuli, resulting in a reduction of the valency—hence of the binding affinity of the capture agent—and subsequent inability of the polynucleotide-encoded capture agent to remain bound to the target. Examples of conditional linkers are peptides or nucleic acids which incorporate W labile bases which break upon exposure to W light. An example of this in practice would be to use p/MHC proteins coupled to SAC-DNA scaffold via a W labile peptide linker. The capture agent upon binding to T cell receptors will activate the target cell. The polynucleotide-encoded p/MHC capture agent can then be removed after a desired amount of time by exposure to W light.

In several embodiments, polynucleotide encoded capture agents herein described include multiple binding molecules bindingly distinguishable between each other. In those embodiments, multi-ligand encoded capture agents can be used to interrogate multiple targets simultaneously. This would be most advantageous when the targets are assembled within a domain, like on the surface of a cell, because the increase in avidity (as indicated above) would equally apply to this system, where the avidity of the complex would be greater than the affinity each individual binder protein. An example of multi-ligand encoded capture agents would include p/MHC complexes where each protein would consist of a distinct peptide sequence. Other combinations are possible like Ab Ab, Ab peptide, Ab aptamer, peptide aptamer, and additional molecules identifiable by a skilled person upon reading of the present disclosure.

The modular polynucleotide encoded capture agent herein described can be manufactured by binding the units in view of the specific capture and the experimental design according to procedures that are identifiable by a skilled person. For example, in embodiments wherein a binding molecule specifically binds the scaffold, the encoding polynucleotide (e.g. DNA) can be first coupled to the scaffold (e.g. SAC) before assembling the binding molecule (e.g. MHC). In other embodiments, where the binding molecule does not bind specifically the scaffold the binding unit needs to be covalently attached. This can either occur before or after attachment of the polynucleotide to the scaffold. Additional procedures to assemble a modular capture agent herein described with other scaffolds and binding molecule will be easily identifiable to a skilled reader. Those procedure would suitable to assemble the capture agents herein disclosed regardless which order the reagent is assembled, as long as that the specificity of the binding protein unit needs to be encoded uniquely by the polynucleotide sequence.

In some embodiments, where the scaffold is streptavidin, a modular polynucleotide-encoded protein can be prepared by enzymatically mixing biotinylated MHC molecules with commercial preparations of streptavidin (SA), usually in a 4:1 proportion, the streptavidin usually conjugated to a fluorescent dye molecule. Variations on this procedure all focused on improving the MHC tetramers for flow-cytometry based cell sorting will be identifiable by a skilled person.

For example, in some embodiments, the binding protein can be attached via protein-ligand interaction (streptavidin biotin), protein-protein interaction (Fc domain and protein A/G), or bioconjugation strategies (amine coupling, sulfhydryl coupling, etc.). In some embodiments where the binding molecule is MHC, MHC can be biotinylated at the C terminus In some embodiments where the scaffold is SAC, SAC is modified with DNA at the C terminus. In some embodiments, the entire unit is assembled by pooling biotin-MHC with SAC-DNA, in which SAC binds specifically to 4 MHC protein molecules via biotin Conjugation of an encoding polynucleotide with the scaffold protein of the modular polynucleotide-encoded capture aget herein disclosed can be produced with common bioconjugation methods, such as chemical cross-linking which include techniques relying on the presence of primary amines in the protein to be bound (usually found on Lysine residues). In particular, polynucleotide-encoded-protein can be produced by the covalent conjugation strategy such as the ones described in PCT application WO2008/016680 incorporated herein by reference in its entirety. In particular, chemical conjugation is used to generate covalent linkages between scaffold protein and polynucleotide, these include NHS-amine coupling, thiol-thiol coupling, thiol-maleimide coupling, hydrazide-aldehyde coupling, etc. These bioconjugation strategies should be evident by any person with technical expertise in the area.

The number of encoding polynucleotides to be conjugated with a particular polynucleotide-encoded capture agent can be varied. In particular, the number of polynucleotides attached to the protein component can be modulated to minimize the size and therefore the steric hindrance of the pending moieties while still maintaining binding specificity. The optimization can be performed by way of procedures exemplified in PCT application WO2008/016680 incorporated herein by reference in its entirety, (see in particular FIG. 3 and Example 3) In those embodiments an optimization of the capture agent can be carried forth chemically (i.e. varying stoichiometric amounts of reactive small molecule with capture agent (e.g. Antibody)).

In some embodiments, the number of encoding polynucleotides to be attached to each protein can be any from 1 to 6 or even more than 6. In some embodiments, such as cell sorting, attaching 1 to 4 encoding polynucleotides per scaffold provides the further advantage of minimizing the steric effects of labeling and therefore allowing a labeling of a polynucleotide-encoded capture agent with a plurality of encoding polynucleotides for high affinity hybridization with the complementary substrate polynucleotide.

The length of the polynucleotide forming the pending moieties can also be controlled to optimize binding of the polynucleotide-encoded capture agent to the substrate. In particular, the length of the encoding polynucleotides can be optimized for orthogonalization purposes. In those embodiments, the encoding region contains a 20mer recognition sequence. These were generated in silico according to procedures exemplified in PCT application WO2008/016680 incorporated herein by reference in its entirety. In particular the sequences containing restriction sites mentioned in the examples were generated by appending the 6 base cutting site to the sequences originally generated according to procedures exemplified in PCT application WO2008/016680 incorporated herein by reference in its entirety.

The substrate polynucleotides can be produced by techniques known in the field. For example, first the polynucleotides can be chemically synthesized. The polynucleotides can then be pin spotted according the paradigm outlined by Pat Brown at Stanford [Ref. 46]. The substrate polynucleotides so produced can be then attached to a substrate according to techniques identifiable by a skilled person upon reading of the present disclosure. Particularly, suitable polynucleotides for the production of substrate polynucleotides include at least 75mers long on polylysine substrates.

In some embodiments, the encoding polynucleotides and/or the substrate polynucleotides are orthogonalized to minimize the non-specific binding between encoding-polynucleotide and substrate polynucleotide. Accordingly, orthogonalized polynucleotides include polynucleotides whose sequence is computationally generated to minimize incomplete base pairing, metastable states and/or other secondary structures to minimize non specific interactions between polynucleotides and non linear secondary interactions in the polynucleotide usually associated with random generation of the relevant sequences.

The term "orthogonalization" as used herein refers to the process by which a set of polynucleotides are generated computationally, in which incomplete base pairing, metastable states and other secondary structures are minimized, such that a polynucleotide only binds to its complementary strand and none other. Exemplary orthogonalization techniques used in this disclosure include orthogonalization performed according to the paradigm outlined by Dirks et al. [Ref. 47] herein incorporated by reference in its entirety.

Figure 15:
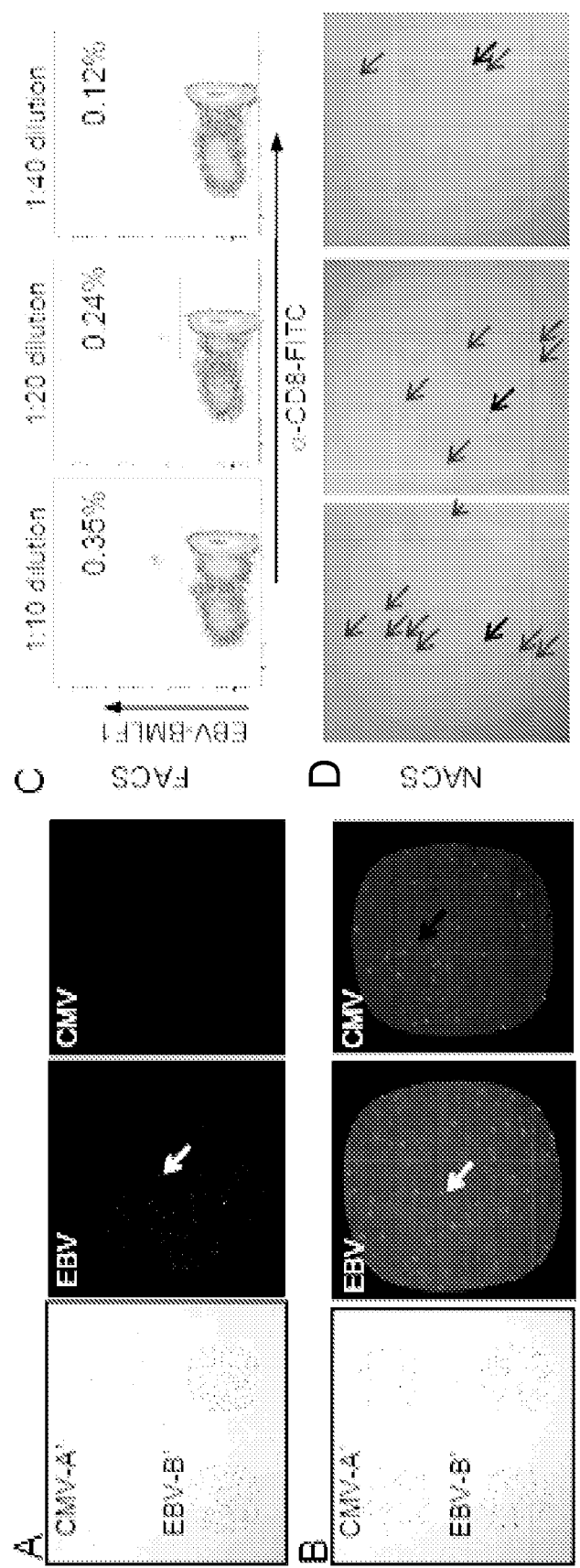
FIG. 15 shows detection of endogenous primary cells performed using modular polynucleotide encoded capture agents according to an embodiment herein described. Panel A shows images of arrays containing polynucleotide encoded p/MHC capture proteins EBV BMLF1$_{259\text{-}267}$/HLA-A2.1 and CMV pp65$_{495\text{-}503}$/HLA-A2.1 as indicated, following contact with the CD8+ T cells specific for EBV-BMLF-1 of FIG. 13 (Patient NRA 13). The left panel shows an array localized with p/MHC capture proteins EBV BMLF1$_{259\text{-}267}$/HLA-A2.1 and CMV pp65$_{495\text{-}503}$/HLA-A2.1 (to A and B cDNA spots respectively) after contact and capture of patient NRA 13 cells containing CD8+ T cells specific for EBV-BMLF-1 but not CMV-pp65 (independently verified by flow cytometry in FIG. 13). The right two panels are representative gray-scaled fluorescence images of the arrays after staining of the cells with fluorescent EBV BMLF1$_{259\text{-}267}$/HLA-A2.1 (blue, shown in the figure as white arrows) and CMV pp65$_{495\text{-}503}$/HLA-A2.1 p/MHC tetramers (red shown in the grayscale version of the figure as black arrows). Panel B shows images of arrays of ss-DNA-SAC-p/MHC specific for EBV or CMV as indicated, following contact with a 1:1 mixture of the CD8+ T cells specific for EBV-BMLF-1 shown in FIG. 13 (Patient NRA 13) and CD8+ T cells specific for CMV-pp65 (Patient NRA11). The left panel shows brightfield image immediately after cell capture, with T cells localizing on spots A and B. The right two panels are representative fluorescence images of the arrays after staining of the cells with fluorescent EBV (blue, shown in the figure as white arrow) and CMV p/MHC tetramers (red shown in the grayscale version of the figure as black arrow). Panel C shows diagrams illustrating quantity and specificity of mixtures of ~0.4%, 0.2% and 0.1% human EBV-specific T cell populations, as determined by flow cytometry. Panel D shows a grayscale version of fluorescence images of arrays of modular polynucleotide-encoded protein specific for EBV following contact with the mixture of Panel C. Populations of EBV-specific T cells are marked with light gray arrows and non-specific cells are marked with black arrows
Figure 16:
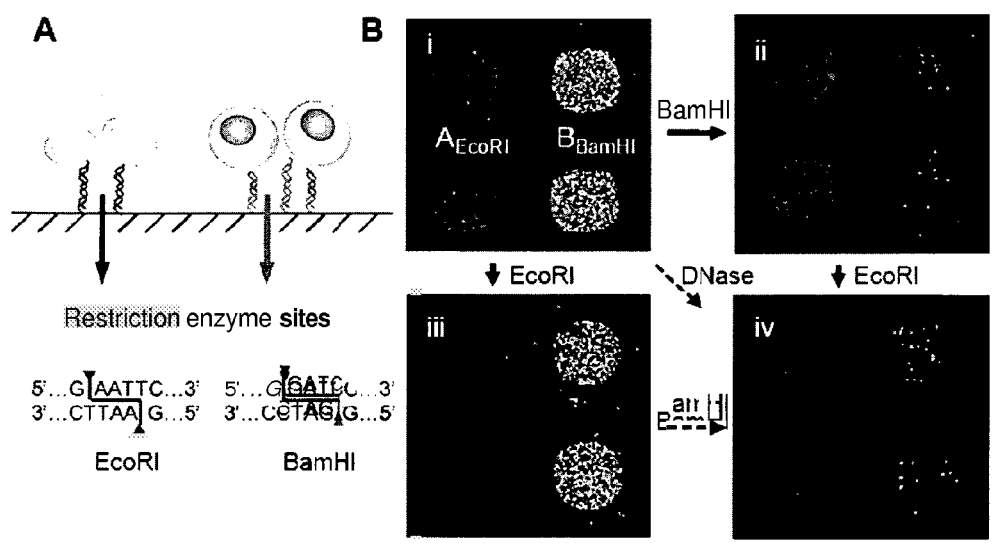
FIG. 16 shows controlled release of targets captured using modular polynucleotide encoded capture agents according to an embodiment herein described. Panel A shows a schematic illustration of the experimental approach. Panel B shows grayscale version of fluorescence images Jurkat$^{\alpha\text{-}MART\text{-}1}$ (red shown in the grayscale version as dark gray) and Jurkat$^{\alpha\text{-}Tyr}$ cells (green shown in the grayscale version as light gray) (i) captured on p/MHC array (ii) after treatment with BamHI (iii) after treatment with EcoRI and (iv) after treatment with BamHI and EcoRI.

In particular, in some embodiments, the encoding-polynucleotides and the corresponding complementary substrate polynucleotides are orthogonalized polynucleotides such as polynucleotides A, B, and C described in detail in Example 6 and in FIGS. 5, 6, 9-13, 15, 17, 19, 22 and polynucleotides AEcoRI, BBamHI described in Example 7 and in FIG. 16.

Additional orthogonalized polynucleotides can be further identified by way of methods and procedures, such as in silico orthogonalization (i.e. computerized orthogonalization) of polynucleotides according to procedures that would be apparent to a skilled person upon reading of the present disclosure.

The modular polynucleotide-encoded capture agents herein described using MHC as a binding molecule can be manufactured using a procedure extensively described in [Ref. 33] herein incorporated by reference in its entirety. According to this procedure a library of p/MHC protein molecules can be generated by first synthesizing a sacrificial peptide that is modifiable through a controlled stimulus. For example, in several embodiments this sacrificial peptide contains a non-natural amino acid containing a nitro-phenyl side chain. This functional group is W labile; hence in the presence of W, the sacrificial peptide is cleaved into two smaller peptides. Thus it is feasible to generate p/MHC complexes presenting the sacrificial peptide, expose the entire complex to W light, but perform the latter in a solution containing molar excess of an exchange peptide. Upon W exposure, the sacrificial peptide will be cleaved in two, and will be displaced for the full length exchange peptide, for which the MHC will have higher affinity. By employing a library of peptides, it will be possible to generate large p/MHC libraries in one UV exchange step.

The methods and systems herein disclosed can be used for performing assays for the detection of targets, including mono-parameter assays, and multiparameter assays, all of which can be performed as multiplex assays.

The term "monoparameter assay" as used herein refers to an analysis performed to determine the presence, absence, or quantity of one target. The term "multiparameter assay" refers to an analysis performed to determine the presence, absence, or quantity of a plurality of targets. The term "multiplex" or "multiplexed" assays refers to an assay in which multiple assays reactions, e.g., simultaneous assays of multiple analytes, are carried out in a single reaction chamber and/or analyzed in a single separation and detection format.

In some embodiments, the methods and systems herein disclosed can advantageously used to perform diagnostic assays, wherein the target(s) to be detected are predetermined biomarkers associated with a predetermined disease. Those embodiments are particularly advantageous in a diagnostic approach where different classes of biomaterials and biomolecules are each measured from a different region of a typically heterogeneous tissue sample, thus introducing unavoidable sources of noise that are hard to quantitate.

Figure 3:
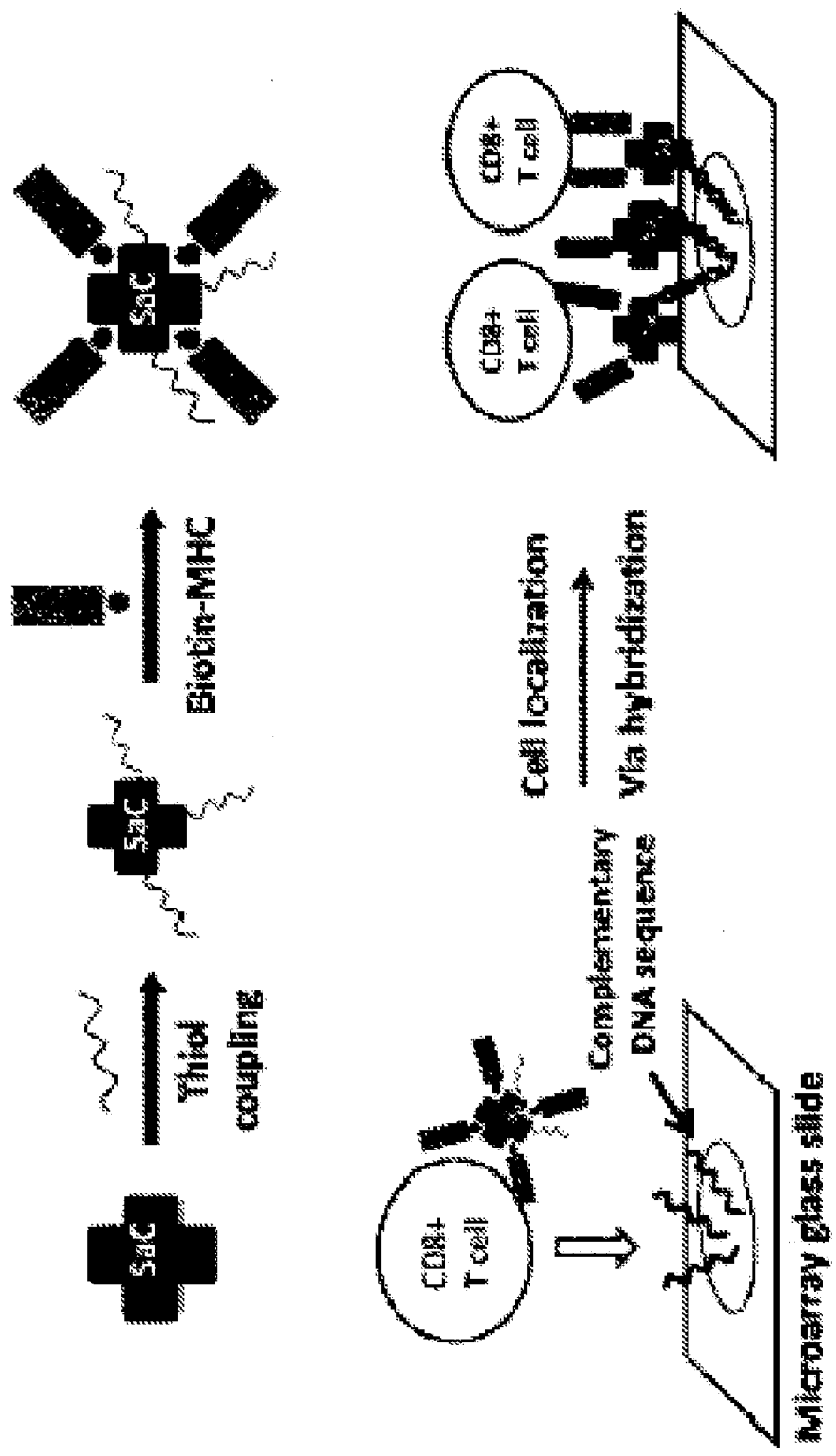
FIG. 3 shows a schematic illustration of modular polynucleotide encoded capture agents, methods and systems according to an embodiment herein disclosed.
Figure 4:
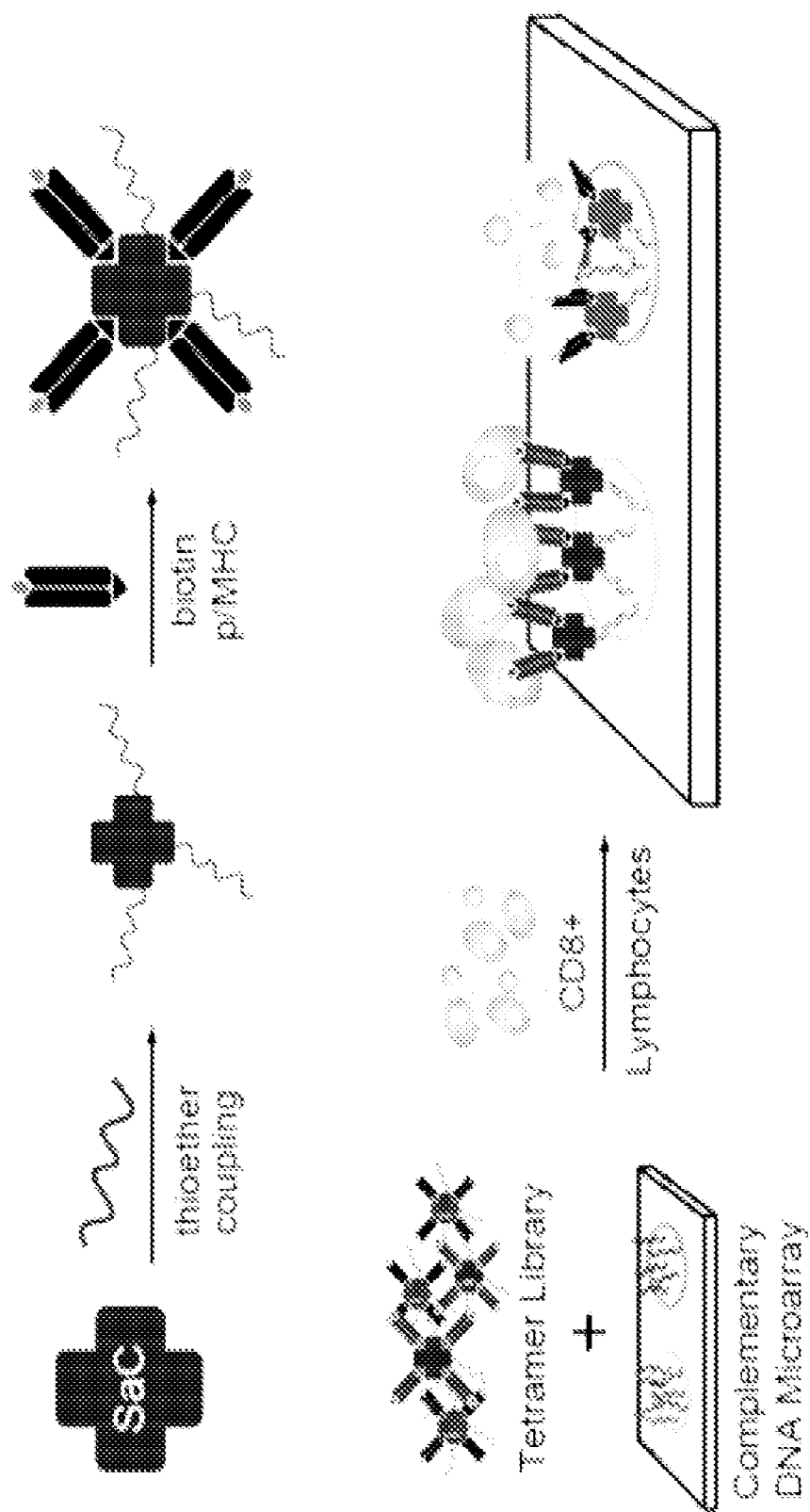
FIG. 4 shows a schematic illustration of modular polynucleotide encoded capture agents, methods and systems according to an embodiment herein disclosed.
Figure 21:
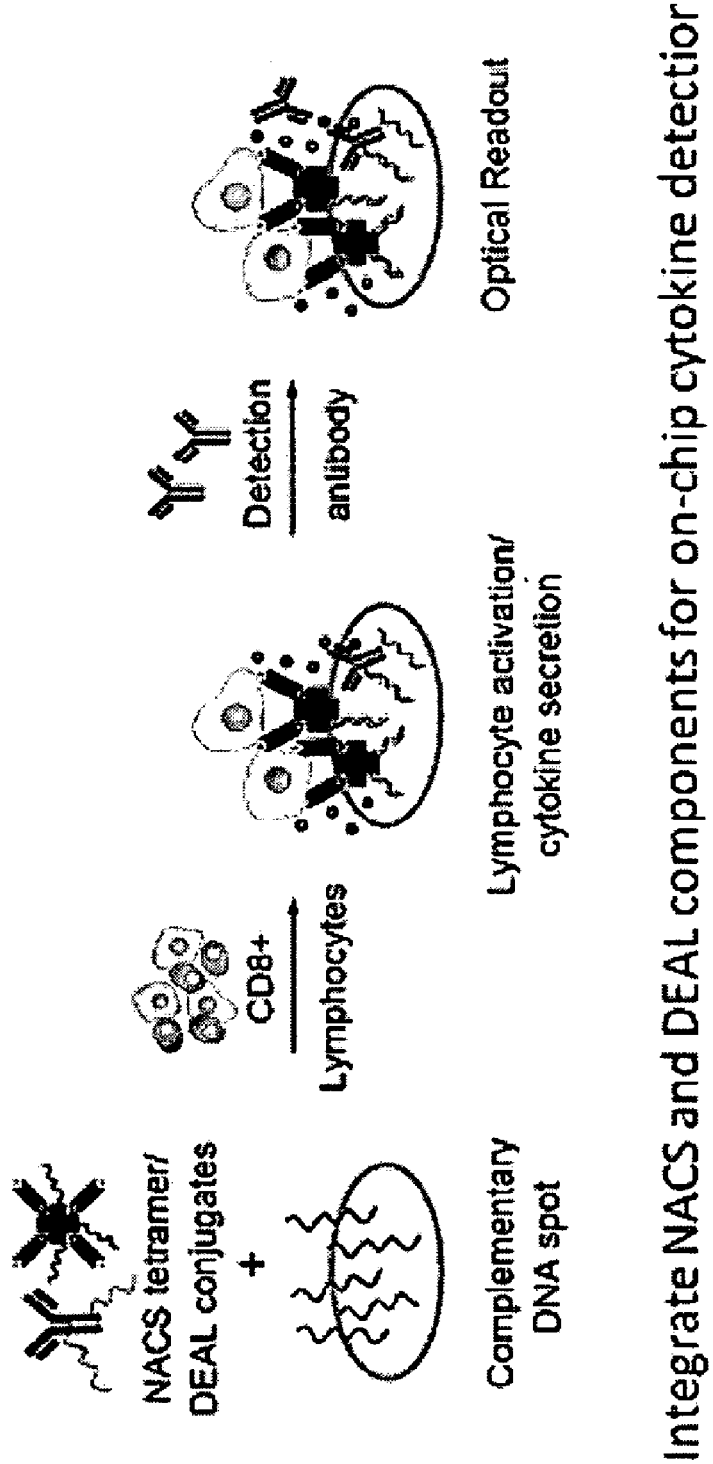
FIG. 21 shows a schematic illustration of the functional profiling of TCR triggered activation of capture antigen-specific cells using DNA-encoded p/MHC tetramers and DNA-encoded antibodies.

In some embodiments of the methods and systems herein disclosed, the polynucleotide-encoded capture agent and substrate polynucleotide are used in combination as schematically illustrated in FIGS. 3, 4, 21.

In the embodiment shown in FIGS. 3, 4, 21 the polynucleotide-encoded capture agent herein disclosed form a protein array that can be contacted with a sample to detect a target in the sample. The embodiment of FIGS. 3, 4, 21 is particularly advantageous for detecting and/or sorting protein-targets.

In additional embodiments, particularly suitable for detecting and/or sorting cells targets, some or all of the modular polynucleotide-encoded capture agents are contacted with the sample before contacting the modular polynucleotide-encoded-antibodies with the complementary substrate polynucleotide. In those additional embodiments, the antibodies and the one or more corresponding targets can bind in absence of the substrate, e.g., in a solution phase, where both molecules have a complete orientational freedom and the access of the target to the binding site of the affinity agent is not impaired by the substrate. Additionally, sensitivity and specificity of the performed assay is improved as well as the detectability of the modular-polynucleotide-encoded target complex bound to the substrate, when compared to corresponding methods and system of the art. Exemplary embodiments showing some of the above advantages are illustrated in Example 12. and in FIG. 17.

In some embodiments, multiple cell types can be sorted on an array by employing a library of protein binders in which the scaffold they are coupled to are encoded with distinct polynucleotides, such that each different protein binder specificity is encoded with a distinct DNA sequence. Examples of this approach in practice are illustrated in Examples 8-11 and FIGS. 5b, 12b, 15b, 16.

In some embodiments of methods and systems herein disclosed the modular polynucleotide-encoded target complex bound to the substrate is eventually detected from the substrate.

In some embodiments, detection of the complex is performed by providing a labeled molecule, which includes any molecule that can specifically bind a modular polynucleotide-encoded-protein target complex to be detected (e.g. an antibody, aptamers, peptides etc) and a label that provides a labeling signal, the label compound attached to the molecule. The labeled molecule is contacted with the polynucleotide-encoded capture agent-target complex and the labeling signal from the label compound bound to the polynucleotide-encoded capture agent-target complex on the substrate can then be detected, according to procedure identifiable by a skilled upon reading of the present disclosure and, in particular, of the Examples section.

In embodiments wherein one or more targets and/or a plurality of targets is detected described below in more details, the labeled molecule can be formed of a plurality of labeled molecules. Each labeled molecules comprises a molecule that specifically binds one target of the one or more targets/plurality of targets and a label compound attached to the molecule, the label compound providing a labeling signal, each labeled molecule detectably distinguishable from another.

The wording "detectably distinguishable" as used herein with reference to labeled molecule indicates molecules that are distinguishable on the basis of the labeling signal provided by the label compound attached to the molecule. Exemplary label compounds that can be use to provide detectably distinguishable labeled molecules, include but are not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and additional compounds identifiable by a skilled person upon reading of the present disclosure.

In some embodiments, the plurality of labeled molecules is contacted with the plurality of modular polynucleotide-encoded capture agent-target complexes for a time and under condition to allow binding of the plurality of polynucleotide-encoded capture agent-target complexes with the plurality of labeled molecules. The labeling signal is then detected from the plurality of labeled molecules bound to the plurality of modular polynucleotide-encoded capture agent-target complexes on the substrate.

In some embodiments, the detection method can be carried either via fluorescent based readouts, in which the labeled antibody is labeled with flurophore which includes but not exhaustively small molecular dyes, protein chromophores, quantum dots, and gold nanoparticles In particular, in some embodiments, in any of the methods and systems herein disclosed, detection can be carried out on gold nanoparticle-labeled secondary detection systems in which a common photographic development solution can amplify the gold nanoparticles as further described below. Also, if the readout comes from dark field scattering of gold particles, single molecule digital proteomics is enabled. Additional techniques are identifiable by a skilled person upon reading of the present disclosure and will not be further discussed in details.

The terms "label" and "labeled molecule" as used herein as a component of a complex or molecule refer to a molecule capable of detection, including but not limited to radioactive isotopes, fluorophores, chemiluminescent dyes, chromophores, enzymes, enzyme substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" as used herein indicates the signal emitted from the label that allows detection of the label, including but not limited to radioactivity, fluorescence, chemolumiescence, production of a compound in outcome of an enzymatic reaction and the likes. In particular gold nanoparticles can be used in a sandwich style detection assay, in which the detection complex is linked to a gold nanoparticle. This is most relevant in detecting small molecules like proteins, peptides, etc, as detecting cells can be simply carried out using traditional microscopy techniques.

In some embodiments, one specific target is detected. In those embodiments contacting the modular polynucleotide-encoded capture agent with the target can be performed before or after contacting the polynucleotide-encoded capture agent with the substrate. In particular, the units forming the modular capture agents can be contacted in a single reaction mixture. Such an approach, however, will require specificity of the binding between scaffold and binding molecule as well as of scaffold and encoding polynucleotide (which is usually already specific).

The embodiments wherein contacting the modular polynucleotide encoded capture agent with the target is performed before contacting the modular polynucleotide-encoded protein with the substrate are particularly suitable to sort or detect cells. This approach is exemplified in Example 12 and in FIG. 17.

The embodiments wherein contacting the modular polynucleotide-encoded capture agents with the target is performed after contacting the modular polynucleotide-encoded capture agents with the substrate are particularly suitable to sort or detect proteins with high sensitivity.

Exemplary embodiments of methods and systems herein disclosed wherein contacting the polynucleotide-encoded capture agent with the target is performed after contacting the polynucleotide-encoded capture agent with the substrate are exemplified in Examples 3, 7, 8, 9, 10, 11 and illustrated in FIGS. 5-6, 9-13, 15-16, 19.22. In those embodiments, competition for the same specific substrate polynucleotide between a polynucleotide-encoded-proteins bound to the target and polynucleotide-encoded-proteins not bound to the target can be eliminated and the sensitivity of the assay consequently increased. Further, in those embodiments the concentration of polynucleotides on the substrate can be optimized so that higher concentration of polynucleotide-encoded capture agents can be bound to the substrate, which will in turn result in higher concentrations of correctly assembled complex, which in turn increase the overall detection sensitivity, by virtue of equilibrium thermodynamics law that govern each binding.

Monoparameter assays that can be performed with the methods and systems exemplified in FIGS. 5a, 6, 9-11, 12Ac, 13b, 15ad, 17b, 19, 22 and in Examples 1, 7-10, include but are not limited to, any assays for the detection of single markers in serum, single protein detection in biological samples, cell sorting according to one surface marker and further assays identifiable by a skilled person upon reading of the present disclosure.

In particular, monoparameter assays can be performed to detect in a sample CD8 cell, CD4 cells or antigen-specific T-cells (i.e. cells that are distinguished from one another by their T-cell receptors (TCRs), which give them their antigen specificity)

In some embodiments, detection of a plurality of targets is performed, according to a strategy schematically illustrated in Examples 3, 8, 10 and 11 and in FIGS. 3-6, 12b, 15b, 16, 22.

In some embodiments, a protein array composed of a plurality of bindingly distinguishable and positionally distinguishable modular polynucleotide-encoded capture agents can be produced. Those embodiments are particularly advantageous for sorting and/or detecting different protein-targets with a high sensitivity.

In additional embodiments, the plurality of modular polynucleotide-encoded capture agent is contacted with a sample for detection of the related target before contacting the substrate polynucleotides. In those embodiments, the methods and systems herein disclosed can be used to perform multiplexed multiparameter assays wherein due to the improved sensitivity and selectivity associated with binding of a binding protein and target in absence of a substrate and in view of the reduced biofouling and protein denaturation, a large number of biomarkers can be efficiently detected in a quantitative and/or qualitative fashion.

Multiparameter assays that can be performed with the methods and systems exemplified in Examples 3, 8-11 and illustrated in FIGS. 3-6, 12b, 15b, 16, 22 include but are not limited to any proteomic analysis, tissue analysis, serum diagnostics, biomarker, serum profiling, multiparameter cell sorting, single cell studies, and additional assays identifiable by a person skilled in the art upon reading of the present disclosure.

In some of those embodiments, multiparameter assays can be performed to detect in a sample CD8 cell, CD4 cells and antigen-specific T-cells in a multiplexed detection approach.

Embodiments of the methods and systems wherein the plurality of targets is composed of different types of cells are particularly advantageous over corresponding methods and systems of the art such as panning in which cells interact with surface marker-specific antibodies printed onto an underlying substrate [Ref. 48]. In particular, the efficiency of cell capture on the substrate is improved with respect to prior art methods and systems, due to the fact that with panning the tertiary structure of capture antibodies are detrimentally and irreversibly damaged by absorption/covalent attachment to common derivatized substrates. This results in surfaces which are less reactive when compared with NACS as exemplified in Example 7 and illustrated in FIGS. 10 and 11.

In several embodiments the modular polynucleotide-encoded capture agents herein described are used in a cell sorting approach.

Assays to sort targets performable with the methods and systems exemplified in Examples 1-11 and illustrated in FIGS. 3-13, 15-17, 19, 21, 22, include any assay that requires detection of a particular target (including but not limited to cell targets, protein-target or gene targets) in a mixture, which will be identifiable by a skilled person upon reading of the present disclosure.

In particular, methods and systems herein described allow multiplexed sorting of specific cell types from at least a 1:1000 dilution within a complex mixture of cell types. Such sorting of rare cells is demonstrated even for the case when the cell-specific affinity agents exhibit a relatively weak binding affinity.

In some embodiments, the polynucleotides (e.g. DNA oligos) employed for encoding the capture agent are designed to include distinct restriction enzyme sites which complementary restriction endonucleases can cleave (herein also releasable polynucleotide-capture agent).

In particular, the restriction sites are included so that different restriction enzymes recognize different DNA sequences on bindingly distinguishable capture agents. Thus by using a plurality of distinct restriction enzymes, the adhesion of distinct populations of capture agents and, as a consequence, of distinct population of target, and in particular cells can be independently controlled by the addition of the complementary restriction enzyme specific for the sequence employed to sort that cell type. The released cells can be expanded further in vivo by cell culturing for enrichment, or can be genomically or proteomically analyzed (e.g. PCR, western blots, etc.) with monoparameter or multiparameter assays as described in the present disclosure.

The controlled release of any captured target with the polynucleotide encoded-capture agent will allow further analysis of the target by other conventional bioanalytical techniques, like PCR, mass spec, western blots, etc, and other techniques that will be identifiable by the skilled reader.

Accordingly in some embodiments releasable polynucleotide encoded capture agents here described can be used in connection with a method wherein a target and in particular a plurality of targets is provided, the polynucleotide encoded capture agents are contacted with the target and a substrate attaching substrate polynucleotides for a time and under condition to allow formation of polynucleotide-encoded capture agent-target complexes on the substrate. A restriction enzyme for a restriction site of a releasable polynucleotide encoded capture agent is then contacted with the releasable polynucleotide-encoded capture agent-target complexes to allow cleavage of the complementary restriction site, thus allowing selective release of the releasable polynucleotide-encoded capture agent-target complexes comprising the restriction site complementary to the restriction enzyme. In some embodiments, the release performed with the method herein described can be selectively controlled to release different releasable polynucleotide-encoded capture agent-target complexes in a controlled fashion (e.g., at different times).

In some embodiments, the releasable polynucleotide-encoded capture agent-are modular polynucleotide-encoded capture agent herein described. In particular, in some embodiments, the releasable modular polynucleotide-encoded capture agent according to this method further comprise the linker molecule to allow controlled release of the modular polynucleotide encoded capture agent herein described thus allowing additional analysis of the target in absence of the capture agent.

In several embodiments, also target captured in an array, and in particular cells captured on an array will be amenable to further analysis. Specifically, immuno-PCR can be employed to profile the cell surface receptors. In addition or in the alternative, it is possible to use a set of polynucleotide-encoded capture agent such as the ones described in WO2008/016680 herein incorporated by reference in its entirety, to perform such analysis, which can be carried out according to procedures exemplified in Example 16 and FIGS. 20-22. In particular, in the example of FIGS. 20-22 antibodies against target surface biomarkers are labeled with unique DNA sequences. These polynucleotide-encoded antibodies are then used to stain the cells captured on the array. The DNA tags on the encoded antibodies can then be analyzed, and the presence or absence of the target cell biomarkers will be correlated to the presence or absence of the DNA tags associated with the cell biomarker. The DNA tags can be detected with conventional techniques like PCR, sequencing, microarrays, and additional techniques identifiable by a skilled reader.

Accordingly, in some embodiments, polynucleotide-encoded capture agents and the modular polynucleotide-encoded capture agents here described can be used in combination in a method to detect and in particular analyze a target wherein at least one of the modular polynucleotide-encoded capture agents and polynucleotide-encoded capture agents is contacted with a target and/or with a substrate polynucleotide attached on a substrate to allow formation of modular polynucleotide-encoded capture agent-target complexes and/or polynucleotide-encoded capture agent-target complexes. Additional polynucleotide-encoded capture agents and/or modular polynucleotide-encoded capture agents can further be contacted with those complexes to allow binding with the target and/or with additional targets presented on the targets to form additional polynucleotide-encoded capture agents-complexes. Complexes of the additional polynucleotide-encoded capture agents and/or modular polynucleotide-encoded capture agents with the additional targets can therefore be detected. Additional variants, based on the use of releasable polynucleotide capture agents and/or of polynucleotide-encoded capture agents comprising a linker, and in particular a conditional linker, will be apparent to a skilled person, In additional embodiments, the substrate of any of the methods and systems herein disclosed can be associated with a microfluidic component so to allow performance of microfluidic based assays. Microfluidic-based assays offer advantages such as reduced sample and reagent volumes, and shortened assay times [Ref. 49]. For example, under certain operational conditions, the surface binding assay kinetics are primarily determined by the analyte (protein) concentration and the analyte/antigen binding affinity, rather than by diffusion [Ref. 50].

The term "microfluidic" as used herein refers to a component or system that has microfluidic features e g channels and/or chambers that are generally fabricated on the micron or sub-micron scale. For example, the typical channels or chambers have at least one cross-sectional dimension in the range of about 0.1 microns to about 1500 microns, more typically in the range of about 0.2 microns to about 1000 microns, still more typically in the range of about 0.4 microns to about 500 microns. Individual microfluidic features typically hold very small quantities of fluid, e.g. from about 10 nanoliters to about 5 milliliters, more typically from about 100 nanoliters to about 2 milliliters, still more typically from about 200 nanoliters to about 500 microliters, or yet more typically from about 500 nanoliters to about 200 microliters.

The microfluidic components can be included in an integrated device. As used herein, "integrated device" refers to a device having two (or more) components physically and operably joined together. The components may be (fully or partially) fabricated separate from each other and joined after their (full or partial) fabrication, or the integrated device may be fabricated including the distinct components in the integrated device. An integrated microfluidic array device includes an array component joined to a microfluidic component, wherein the microfluidic component and the array component are in operable association with each other such that an array substrate of the array component is in fluid communication with a microfluidic feature of the microfluidic component. A microfluidic component is a component that includes a microfluidic feature and is adapted to being in operable association with an array component. An array component is a component that includes a substrate and is adapted to being in operable association with a microfluidic component.

The microfluidic systems can also be provided in a modular form. "Modular" describes a system or device having multiple standardized components for use together, wherein one of multiple different examples of a type of component may be substituted for another of the same type of component to alter the function or capabilities of the system or device; in such a system or device, each of the standardized components being a "module".

In microfluidic embodiments of the methods and systems herein disclosed, measurements of large panels of protein biomarkers within extremely small sample volumes and a very reduced background/biofouling are possible.

In the microfluidic embodiments of the methods and systems herein disclosed, the sensitivity of the assay can also be increased.

Additionally, the microfluidic methods and systems herein disclosed allow performance of both (i) mono step assays (wherein the polynucleotide-encoded capture agent the target(s) and labeled antibodies are contacted in a single step) and (ii) multi-steps assays (wherein the substrate is sequentially exposed to modular polynucleotide-encoded capture agent, target(s), and then secondary antibody) in a reduced amount of time, with samples reduced in size and with a higher sensitivity when compared with corresponding microfluidic methods and system of the art and with other non-microfluidic methods and systems for molecule detection An additional advantage associated with microfluidic methods and systems herein disclosed includes the possibility of performing in a microfluidic environment any assay that involves substrate-supported antibodies, which would not have survived microfluidic chip assembly with the use of previous techniques.

Further advantages associated with the methods and systems herein disclosed are: the possibility of performing sensitive measurements using low cost reagents, such as glass, and plastic; and of using the substrate in combination with additional components for sample pretreatment and purification.

The methods and systems herein disclosed allow the multiplexed multiparameter detection, sorting and of biomarkers of interest and related diagnostic analysis. Exemplary illustration of applications of the methods and systems herein disclosed for diagnostic analysis are described in Examples 9-10 and shown in FIGS. 13-15, 21-22, and any additional assay identifiable by a skilled person upon reading of the present disclosure.

Figure 13:
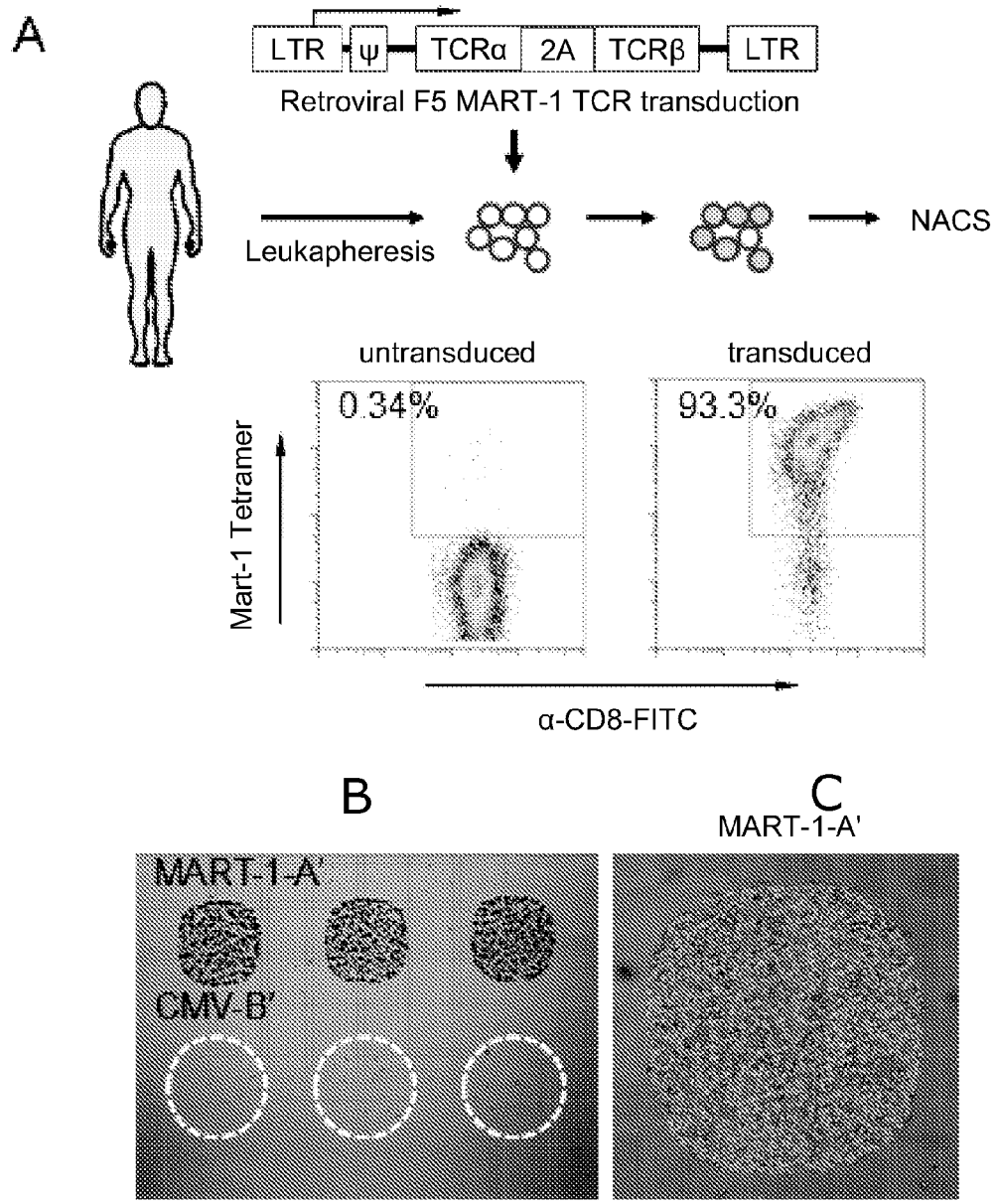
FIG. 13 shows detection of engineered cells performed using modular polynucleotide encoded capture agents according to an embodiment herein described. Panel A shows a schematic illustration of the experimental approach for transduced PMBC cells with F5 MART-1 TCR and related diagrams showing transduction efficiency as determined by flow cytometry. Panel B shows a gray scaled brightfield image of transduced PBMCs sorted on a microarray containing the cognate capture protein (MART-1$_{26\text{-}35}$/HLA-A2.1) and the control capture protein (CMV pp65$_{495\text{-}503}$/IILA-A2.1) encoded to A and B respectively. Panel C shows an overlay of confocal and brightfield images, verifying that cell capture illustrate in Panel B was specific (MART-1 cells shown in light gray).

In particular, in the exemplary diagnostic assays of FIGS. 13-15, antigen-specific T cell populations were directed detected with NACS from human PBMCs. Detection of these T cells is important for diagnostic purpose because they are involved in the immune response against cancer and viral pathogens. Examples of therapeutic assays are instead provided in FIG. 13. Here human PBMCs are transduced with a TCR specific for a cancer associated antigen. These T cells are detected on a NACS array prior to subsequent infusion into a patient.

The systems herein disclosed can be provided in the form of arrays or kits of parts. An array sometimes referred to as a "microarray" includes any one, two or three dimensional arrangement of addressable regions bearing a particular molecule associated to that region. Usually the characteristic feature size is micrometers. Examples 3-11, and FIGS. 3-6, 9-13, 15-17, 19, 21-22 provide exemplary microarrays.

In a kit of parts, the modular polynucleotide-encoded capture agents and/or any of the relevant components are independently comprised in the kit together with a substrate. In particular, the modular polynucleotide-encoded capture agent can be included in one or more compositions, and each modular polynucleotide-encoded capture agent can be comprised in a composition together with a suitable vehicle carrier or auxiliary agent.

The substrate provided in the system can have substrate polynucleotide attached thereto. In some embodiments, the substrate polynucleotides can be further provided as an additional component of the kit. Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

Example 1

Production of Polynucleotide Encoded SAC Scaffold Protein

Expression of SaC was expression was performed according to previously published protocols [Ref. 36]. Briefly the streptavidin-cysteine (SaC) gene cloned into the pET-3a plasmid was a generous gift from Dr. Takeshi Sano (Harvard Medical School). Following colony selection and overnight start culture, BI21(DE3)-pLysE containing the plasmid was grown at 37° C. with shaking in LB medium and selection antibiotics ampicilin (50 ltg/ml) for pET-3a-SaC and chlorophenicol (25 ltg/ml) for pLysE. Induction of the cells occurred when A600 reached 0.6 at which b-D-thiogalacto-pyranoside (IPTG) was added to a final concentration of 0.4 mM. Following induction the cells were kept spinning at 37° C. for 4 hours. The culture was then centrifuged at 1600 g for 10 min and washed with 100 mM NaCl, 1 mM EDTA, 10 mM Tris-HCl, pH 8.0. The cells were then lysed with lysis buffer (2 mM EDTA, 30 mM Tris-HCl, 0.1% Triton X-100, pH 8.0).

To reduce the viscosity of the solution, the lysate was then treated with DNase and RNase (10 ltg/ml each, with J2 mM MgS04) for 20 min at room temperature. The insoluble inclusion bodies were then separated from the lysate by centrifugation at 39,000 g for 15 min after which the precipitate was washed again with lysis buffer. The precipitate was dissolved in 6 M guanidine-HCl, pH 1.5 to the original culture volume. To remove cellular biotin, 100 mL of dissolved precipitate solution was dialyzed in 1 L of 6M guanidine-HCl, pH 1.5. The dialysate was then transferred to 0.2 M NaAcetate, pH 6.0 to remove guanidine and in the process refold SaC. It is critical here to perform the dialysis slowly, by removing the stir bar. The dialysate was then spun at 3000 g for 10 min to remove precipitated material and filtered through a 0.2 !-Lm tllter (amicron). Refolded SaC was lastly dialyzed against 50 mM Bicarbonate, 500 mM NaCl, pH 11.

SaC were purified as follows. Refolded volumes of SaC were mixed 1:1 with binding buffer (50 mM Sodium Bicarbonate, 500 mM NaCl, 10mM b-Me, pH 11). A gravity column packed with 1.5 ml of iminobiotin agarose resin (Pierce) was washed with 10 ml of binding buffer. The refolded mixture was then applied to the column and the eluted fractions were collected and reapplied to the column again, to maximize SaC recovery. After washing the column with 20 ml binding buffer, SaC was eluted with pH 4 elution buffer (50 mM Sodium Acetate, 10 mM—-me). Fractions containing SaC, as monitored by OD280, were collected, buffer exchanged to PBS containing 10 mM—-me, and concentrated to 1 mg/ml final concentration using 10K mwco filters (Millipore)

SaC Oligonucleotide Conjugation was performed as follows. Prior to use, stock SaC was buffer exchanged to Tris buffered Saline (TBS) containing 5 mM TCEP using desalting columns (Pierce). TCEP is a nonthiol containing reductant that maintains the reduced form of SaC during conjugation. MHPH (3-N-Maleimido-6-hydraziniumpyridine hydrochloride, Solulink) in DMF was added to SaC at a molar excess of 300:1. In parallel, SFB in DMF (succinimidyl 4-formylbenzoate, Solulink) was added in a 40:1 molar excess to 5' aminated oligos (IDT).

The mixtures were allowed to react at room temperature for 3-4 hours. Excess MHPH and SFB were removed and samples were buffer exchanged to citrate buffer (50 mM sodium citrate, 150 mM NaCl, pH 6.0) using desalting spin columns (Pierce). The SFB-labeled oligos were then combined in a 20:1 molar excess with the derivatized SaC and allowed to react for 2-3 hours at room temperature before transferring to overnight incubation at 4° C. Unreacted oligos were removed using a Pharmacia Superdex 200 gel filtration column at 0.5 mllmin isocratic flow of PBS. Fractions containing the SaC-oligo conjugates were concentrated using 10K mwco concentration filters (Millipore). The synthesis of SaC-oligo constructs were verified by non-reducing 8% Tris-HCI SDS-PAGE.

Example 2

Microarray Fabrication

DNA microarrays were printed via standard methods by the microarray facility at the Institute for Systems Biology (ISB—Seattle, Wash.) onto amine-coated glass slides. Typical spot size was 600 f·lm (SMPXB15 pin, Arrayit). All DNA strands were purchased Integrated DNA technologies, and all complements were 5' aminated. Sequences for all six 3D-mers and their respective designations are given in Table 1 and Table 2 below.

TABLE 1

Seauence Designation

| Name | Sequence | SEQ ID NO |
|---|---|---|
| A | 5'-AAA AAA AAA AAT CCT GGA GCT AAG TCC GTA | 3 |
| B | 5'-AAA AAA AAA AGC CTC ATT GAA TCA TGC CTA | 4 |
| C | 5'-AAA AAA AAA AGC ACT CGT CTA CTA TCG CTA | 5 |

TABLE 2

Complement

| Name | Sequence | SEQ ID NO |
|---|---|---|
| A' | 5'-NHz-AAA AAA AAA ATA CGG ACT TAG CTC CAG GAT | 6 |
| B' | 5'-NHz-AAA AAA AAA ATA GGC ATG ATTCAA TGA GGC' | 7 |
| C' | 5'-NHz-AAA AAA AAA ATA GCG ATA GTA GAC GAG TGC | 8 |

Example 3

Detection and Sorting Methods and Systems Using NACS

Cell sorting of antigen-specific CD8+ T-cells using antigen presenting MHC molecules organized on a ssDNA-oligomer-labeled SaC scaffold was performed as schematically illustrated in FIG. 3 and FIG. 4. In particular, the assays schematically illustrated in FIGS. 3 and 4 are directed to cell sorting, by which different cell types can be sorted on a glass substrate and detected by conventional microscopy techniques. The modular DNA-SAC-MHC construct is first hybridized to the array, after which a complex cell sample containing the target T cell of interest is applied and sorted on the array.

According to a first series of experiments, the protein SaC was expressed, and ssDNA oligomers are coupled to the cysteine residues using thiol coupling according to procedure exemplified in Example 1 (see FIG. 3).

A biotinylated antigen-presenting MHC was coupled to the SaC at the biotin/SaC binding sites, by combining molar excess of p/MHC monomers to SaC-oligo and incubating at 37° C. for 20 minutes. (see FIG. 3).

The SaC/MHC/ssDNA scaffold was then combined with a solution containing the CD8+ cells of interest, and then the entire SaC/MHC/ssDNA/CD8+ assembly is localized to a particular spot on a surface that has been prespotted with complementary ssDNA' oligomers according to procedure exemplified in Example 2 (see FIG. 3).

According to a second series of experiments, self-assembled ssDNA-p/MHC tetramer arrays for multiplexed sorting of antigen-specific cells were prepared. (FIG. 4). ssDNA-tagged p/MHC tetramers were produced by coupling ssDNA site-specifically to SAC prior to exposure to molar excess of biotinylated p/MHC monomers (FIG. 4). p/MHC tetramer arrays are formed by pooling ssDNA-p/MHC tetramers of select specificity and hybridization to a complementary printed ssDNA microarray (FIG. 4). T cells expressing the cognate TCR were detected by binding to the surface confined tetramer.

To perform both series of experiments, two T cell lines Tyrosinase-TCR transgenic Jurkats and Mart-I-TCR transgenic Jurkats, genetically engineered to express TCRs specific for melanoma antigens, were used together with corresponding HLA-A2 restricted class I major histocompatibility complexes (MHC) monomers with tyrosinase 369-377 (YMDGTMSQV—SEQ ID NO: 9) and MartI 26-35 (ELAGIGILTV—SEQ ID NO:10) peptides.

Prior to sorting experiments, the microarray slides were blocked to prevent non-specific cell absorption with 1 mg/ml PEG-NHS ester (Sunbio) dissolved in PBS for 2 hours at room temperature. The slides were then dipped 5 times in 0.5×PBS to remove excess PEG, immediately followed by another 5 dips in dH20 to remove salts. The slides were blown dry with a nitrogen gun. The slides can be stored in a dessicator for up to 2 weeks with no degradation in efficacy.

Solid state sorting was carried out by first combining molar excess of p/MHC monomers to SaC-oligo and incubating at 37° C. for 20 minutes. After tetramerization, 200 ul of DMEM supplemented with 10% FBS was added and the solution pipetted on top of the DNA microarray.

The tetramers were allowed to localize to the complementary spots for 1 hour at 37° C. The slide was then rinsed with 3% FBS in PBS. After rinsing, 106 T cells in 100 III of fresh DMEM were added to the slide on top of the array. The slide was then transferred to a 37° C. incubator for 20-30 min to allow the cells to interact with the p1MHC array. After incubation, the slide was slide gently with 3% FBS in PBS to dislodge unbound cells and visualized via brightfield and fluorescence microscopy. Similarly solution phase capture was carried out by combining $10^6$ cells with 0.5 μg of assembled NACS tetramer, allowing the capture agent to bind to the cells in solution phase. After 20 min incubation at 37° C., the cells were spun at 500 g for 5 min and the excess tetramers removed by aspiration. The cells were resuspended in 100/μL DMEM, 10% FBS, and directly applied to a pre-blocked microarray. The slide was further incubated for 20 min at 37° C. Subsequent washing and imaging steps are identical to the solid state sorting.

Figure 5:
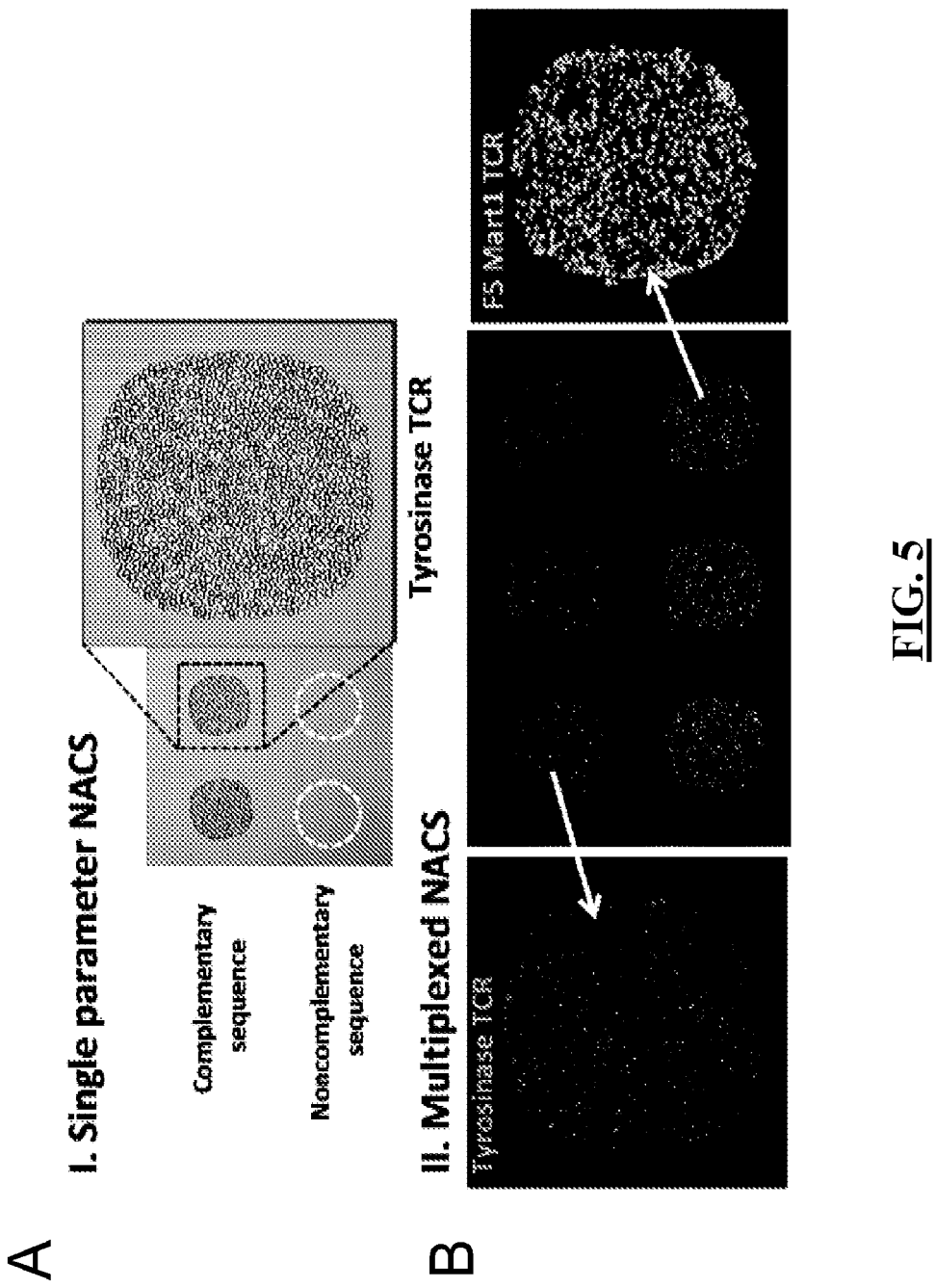
FIG. 5 shows results of cell sorting experiments performed using modular polynucleotide-encoded capture agents according to an embodiment herein described. Panel A shows a grayscale fluorescence image of an array of ssDNA-p/MHC tetramer specific for Tyrosinase TCR contacted with T cells. The image shows detection and cell sorting of the T cells on a substrate where substrate DNA complementary to the encoding polynucleotide of the ssDNA-p/MHC tetramers are attached. Panel B illustrates cell sorting using two sets of ssDNA-p/MHC tetramers each encoded with a ssDNA bindingly distinguishable from the other. The arrows indicate binding of each set after contact with target T cells.

The results of the above procedure performed to obtain a single parameter and multiplexed cell sorting are illustrated in FIG. 5. In particular, the results of FIG. 5 show the usefulness of NACS for single parameter (FIG. 5A) and multiplexed (FIG. 5B) sorting of antigen-specific CD8+ T-cells. A skilled person would appreciate from the details of FIG. 5 the specificity of DNA hybridization as well as functionality of spatially-localized p/MHC proteins that allow target sorting and in particular cell sorting, with minimal inter-spot noise.

To evaluate the sensitivity of detection/sorting performed through the above procedure, a further series of the experiments was carried out where the above procedure was performed to selectively detect and sort antigen-specific CD8+ T-cells diluted in a mixture of other cells at levels of 10%, 1%, and 0.1% with ssDNA-SA-p/MHC tetramer arrays.

The results illustrated in FIG. 6 show the usefulness of NACS approach to selectively detect and/or sort antigen-specific cells in a mixture of other cells. In particular, the micrograph of FIG. 6A illustrates cell sorting efficiency, in which the target T cell populations are spiked in at the percentages indicated at the top left of each subpanel while the histogram of FIG. 6B is a quantitative representation of the such experiments. The shorter bars represent a CD8+ T-cell of different antigen-specificity than the object of the sorting experiment, and so represent the level of background signal.

Example 4

Optimized Scaffolds

Figure 7A:
FIG. 7 shows a representation of the structure of a scaffold (Panel A) and a corresponding optimized scaffold (Panel B) according to an embodiment herein described.
Figure 7B:

The structure of streptavidin is shown FIG. 7A, the structure of optimized streptavidin SAC is shown in FIG. 7B.

Here is the crystal structure of the optimized streptavidin-cysteine protein construct. Streptavidin is made of four identical subunits (in various shades of gray). The biotin binding domain for the protein is illustrated in the figure where the biotin ligand is bound (white). The cysteine residues are illustrated as red "balls" at the carboxy termini. This is the site of attachment of derivatized DNA. Notice that the two regions are separated by a distance of about 20-30 Angstroms. There is a third element in the crystal structure, illustrated by lys121 (gray). This can also serve as the site of attachment of derivatized DNA (via amine-NHS coupling) instead of attachment to the cysteine residues. The problem with this site for attachment is that it is too close in proximity to the biotin pocket (i.e. the domains overlap, 7 Angstroms), so this illustrates an unoptimized scaffold. The diameter of ssDNA is about 10 Angstroms and dsDNA is about 20 Angstroms. Thus if the DNA were attached to the lysine residue, it would physical overlap the biotin binding region (10 A>7 A) preventing specific interaction with biotinylated binder proteins (e.g. biotinylated p/MHC).

A synthetic approach in scaffold design allows precise control over the various parameters of an optimized scaffold. For example, in the case where peptides are used as the scaffold, several parameters involved in scaffold optimization can be controlled, including the linker length separating the binding protein and encoding-polynucleotide attachment regions, polarity, and valency.

Example 5

Optimized and Non-Optimized ssDNA-Encoded p/MHC Tetramers

Applicants expressed SAC, coupled the protein with 5'-maleimide ssDNA, and verified the formation of conjugates with mobility shift assays.

In particular, production of ssDNA-SAC conjugates was performed as follows. The expression of SAC was performed according to previously published protocols from a pET 3a plasmid [Ref. 36]. Prior to conjugation, stock SAC was buffer exchanged to PBS containing 5 mM Tris(2-Carboxyethyl) phosphine Hydrochloride (TCEP) using zeba desalting columns (Pierce). MHPH (3-N-Maleimido-6-hydraziniumpyridine hydrochloride, Solulink) in DMF was added to SAC at a molar excess of 300:1. In parallel, SFB in DMF (succinimidyl 4-formylbenzoate, Solulink) was added in a 40:1 molar excess to 5'aminated oligos. The mixtures were reacted at room temperature (RT) for 3-4 hours before buffer exchanged to citrate (50 mM sodium citrate, 150 mM NaCl, pH 6.0) using zeba columns The SFB-labeled oligos were combined in a 20:1 molar excess with the derivatized SAC and incubated overnight at RT. Unreacted oligos were removed using a Pharmacia Superdex 200 gel filtration column at 0.5 ml/min isocratic flow of PBS. Fractions containing the SAC-oligo conjugates were concentrated using 10K mwco concentration filters (Millipore). In parallel, ssDNA was coupled to native SA for direct comparison.

Figure 8:
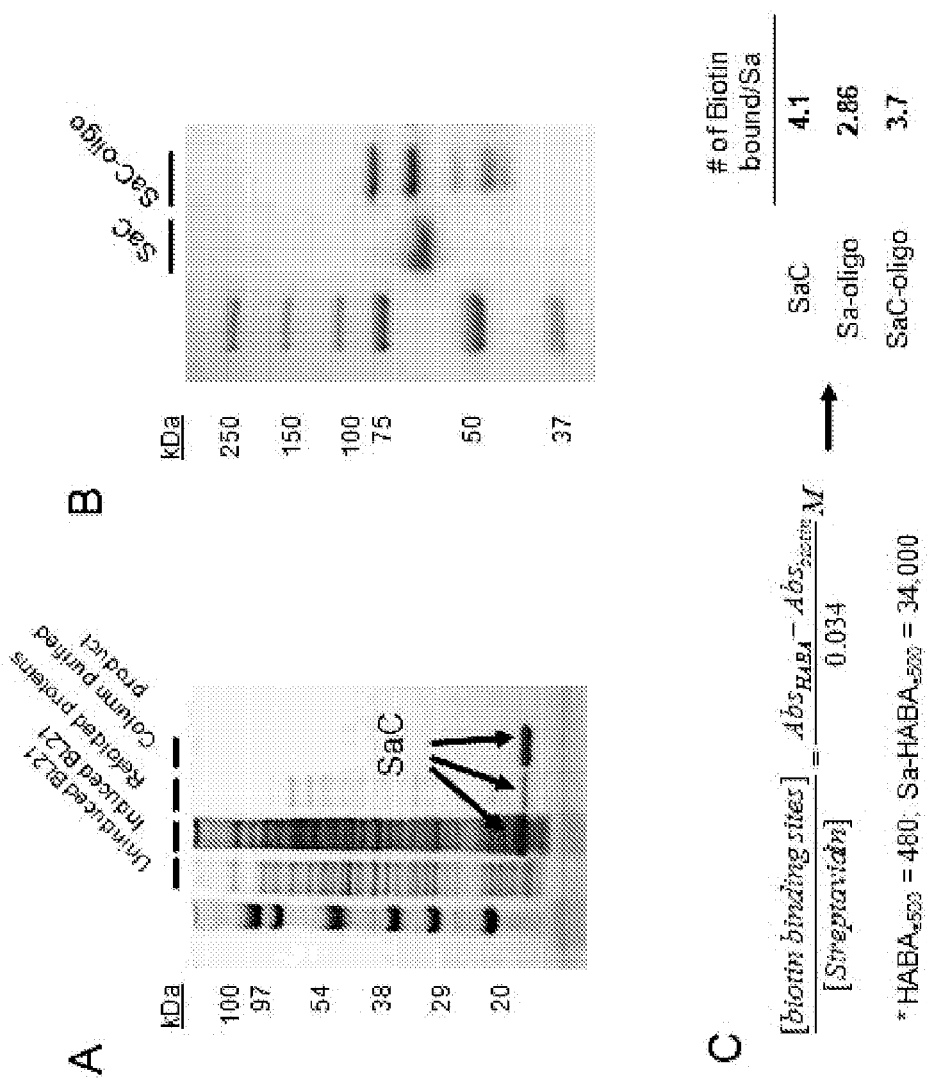
FIG. 8 shows results of experiments exemplifying the binding capacity of an optimized polynucleotide encoded capture agent according to an embodiment herein described. In particular, Panel A shows a denaturing PAGE gel for a SAC protein detected at various stages of expression, refolding, and purification. The molecular weight of a SAC monomer is ~12 kDa. Panel B shows a gel mobility shift assay performed to verify the formation of ssDNA-SAC conjugates. Panel C shows a formula for determining a molar ratio of association of biotin to SA using the molecule 2-(4'-Hydroxyazobenzene)benzoic acid (HABA).

The results illustrated in FIG. 8, indicate that an engineered variant of streptavidin expressing C-terminal cysteine residues has superior biotin binding capacity compared to native streptavidin post conjugation with ssDNA. In particular, the results of FIG. 8 shows that the molecular weight of a SAC monomer is ~12 kDa (FIG. 8A), individual bands representing SAC-oligo conjugates differing by one DNA strand can be resolved and that lower order SAC-oligo conjugates (1-2 oligos per protein) run "lighter" when compared to unmodified SAC because of the difference in charge/mass density of nucleic acids (FIG. 8B). Higher order SAC-oligo conjugates corresponding to 3-4 DNA strands per SA were favored (FIG. 8B).

To test biotin binding capacity, SAC-oligo conjugates were probed with 2-(4'-Hydroxyazobenzene)benzoic acid (HABA) [Ref. 28], a molecular mimic of biotin with distinct optical density coefficients dependent on whether biotin is bound to SA or not. A biotin:SA molar ratio of association significantly below 4 in the assay would indicate a reduction in biotin binding capacity. Conjugates derived from native SA were greater than one full unit below the expected value (2.86 versus 4.0), while conjugates formed with SAC maintained near optimal (3.7) binding capacity (FIG. 8C).

In particular, as shown by FIG. 8 native SA-oligo conjugates bound ~2.9 moles of biotin per mole of SA, a significant decline when compared to the 4:1 ratio of unmodified SAC. SAC-oligo conjugates maintained near optimum binding capacity (3.7:1).

These conjugates were then tested across 4 different monoclonal T cell populations (2 human TCR-transduced cell lines and 2 murine TCR-transgenic splenocyte cell suspensions). ssDNA-tagged SAC constructs had markedly higher cell capture efficiencies compared with p/MHC tetramers prepared with native SA (FIG. 9). In particular, FIG. 9A show the results of cell capture experiments performed using native streptavidin where each sub-panel within FIG. 9A shows the results of a separate experiment using a different cell type. In FIG. 9B, we are testing cell capture efficiency using the same cells, but with the optimized SAC scaffold. A skilled person would appreciate that while the cell capture efficiency of the experiments of FIG. 9A is highly varied, cell capture efficiency of the experiments of FIG. 9B is uniform amongst all the cell types. All subsequent NACS tetramers SA constructs were prepared with the SAC variant.

Here the DNA encoding domain, when attached to the un-optimized scaffold (SA) reduces biotin binding capacity (binding protein domain) resulting in marked reduced T cell capture efficiencies. The optimized scaffold (SAC) minimizes the interaction between the two distinct modalities, resulting in higher efficiency T cell sorting.

The results illustrated in this example further show an increased affinity of the binding molecule by increasing the number of binding molecules comprised in a single capture agent. p/MHC proteins as each individual monomer is characterized by a poor affinity (disassociation constant=$Kd^{-}10^{-5}$, [Ref 2]). However when four p/MHC proteins are bundled together to form a p/MHC tetramer the avidity of the complex is greatly increased ($Kd^{-}10^{-9}$, reference 1). This increase in avidity due to multi-valency should likewise extend to any family of protein binders, aptamers, peptides, small molecules. The effect of valency on the avidity of the capture agent complex is clearly seen in FIGS. 8-9. Here capture agents formed with ~3 p/MHC proteins were of sufficient avidity to capture a subset of T cell populations while fully formed tetramers (4 p/MHC) were able to capture and bind to all 4 T cell populations.

A skilled person will understand that the principle illustrated in of this series of experiments can be adapted to construe other optimized scaffolds, since a valency a capture agent can be calculated along the same line of reasoning. In particular, a skilled person will understand that independently on the specific binding molecule used a poly valent scaffold will always be more avid when compared to a monomer.

Example 6

Microarray Fabrication with Polynucleotides Including Restriction Sites

All DNA strands were purchased from IDT. DNA microarrays were printed by the microarray facility at the Institute for Systems Biology (ISB—Seattle, Wash.) on amine-coated glass slides (GAPS II, Coming) in identical triplicate 12×12 arrays containing alternative rows of A, B and C spots, or $A_{EcoRI}$ and $B_{BamHI}$ with a SMPXB15 pin (Arrayit). Sequences for all strands are reported in the following Table 3.

TABLE 3

Orthogonal DNA sequences for spatial encoding of p/MHC tetramers

| Name | Sequence | SEQ ID NO |
|---|---|---|
| A | 5'-AAA AAA AAA AAA AAT CCT GGA GCT AAG TCC GTA AAA AAA AAT CCT GGA GCT AAG TCC GTAAAAAAAAAAAAAA | 11 |
| A' | 5'-NH$_2$-AAA AAA AAA ATA CGG ACT TAG CTC CAG GAT | 12 |
| B | 5'-AAA AAA AAA AAA AGC CTC ATT GAA TCA TGC CTA AAA AAA AAA AGC CTC ATT GAA TCA TGC CTAAAAAAAAAAAAAA | 13 |
| B' | 5'-NH$_2$-AAA AAA AAA ATA GGC ATG ATT CAA TGA GGC | 14 |
| C | 5'-AAA AAA AAA AAA AGC ACT CGT CTA CTA TCG CTA AAA AAA AAA AGC ACT CGTCTA CTA TCG CTA AAAAAAAAAAAAA | 15 |
| C' | 5'-NH$_2$-AAA AAA AAA ATA GCG ATA GTA GAC GAG TGC | 16 |
| $A_{EcoRI}$ | 5'-AAA AAA AAA AAA GAG CTA AGT CCG TAG M T TCA AAA AAA AAA GAG CTA AGTCCG TAG MTTCAAAAAAAAAAAAA | 17 |
| $A_{EcoRI}$' | 5'-NH$_2$-AAA AAA AAA AGA ATT CTA CGG ACT TAG CTC CAG GAT | 18 |
| $B_{BamHI}$ | 5'-AAA A M AAA AAA TTG M T CAT GCC TAG GAT CCA AAA AAA AAA TTG M T CATGCC TAG GAT CCAAAAAAAAAAAAA | 19 |
| $B_{BamHI}$' | 5'-NH$_2$-AAA AAA AAA AGG ATC CTA GGC ATG ATT C M TGA GGC | 20 |

All sequences of Table 3 to be conjugated to SAC (A', B', $A_{EcoRI}$', and $B_{BamHI}$') were designed with a polyA linker followed by a 20mer hybridization region. The 5' amine is required for the attachment of the hetero-bifunctional maleimide derivative MHPH. Sequences printed on glass substrates (A, B, C, $A_{EcoRI}$, and $B_{BamHI}$) were designed with two hybridization regions separated by polyAs. This was designed to facilitate electrostatic adsorption to amine glass substrates.

Sequences $A_{EcoRI}$ and $B_{BamH}$ were designed to include the restriction site indicated to allow release, and in particular selective release of the target according to procedures such as the ones exemplified in Example 11 below.

Example 7

Performance of p/MHC Arrays Produced via DNA Immobilization and Direct Spotting in Comparison with Conventional Protein Arrays Applicants directly compared the performance of NACS on the arrays provided in Example 6, with conventional direct spotting strategies on various model substrates. The substrates were selected to represent the spectrum of surface chemistries typically used to immobilize proteins (covalent, electrostatic, hydrophobic, and hydrophilic adsorption). Serial dilutions of fluorescent MART-1 SA-PE tetramers (melanoma peptide epitope MART-$1_{26-35}$ loaded onto HLA-A2.1 MHC molecules) were spotted on the substrates according to manufacturer's instructions.

T cells were prepared according to the following procedure. cDNA from the alpha and beta chains of a TCR specific for tyrosinase$_{368-376}$ was used. The TCR$^{Tyro}$ alpha and beta chains were cloned into a lentiviral vector where both transgenes were linked by a 2 A self-cleaving sequence as described [Ref. 37]. Concentrated supernatant from this lentiviral vector was used to infect Jurkat cells to generate Jurkat$^{\alpha-Tyro}$ cells. A MSGV1-F5AfT2AB retroviral vector expressing the F5 MART-1 TCR was used. In particular, the MSGV1-F5AfT2AB retroviral supernatant was used to infect Jurkat cells to generate the Jurkat$^{\alpha-MART-1}$ cell line. To generate primary human T lymphocytes cultures expressing the F5 MART-1 TCR, PBMCs obtained from leukapheresis were activated for 48 hours with 50 ng/ml of OKT3 (muromonab anti-human CD3 antibody, Ortho-Biotech, Bridgewater, N.J.) and 300 U/ml of IL-2 (adesleukin, Novartis, Emeryville, Calif.). MSGV1-F5AfT2AB retrovirus supernatant was applied to retronectin-coated wells (Takara Bio Inc., Japan).

Then activated PBMC in RPMI plus 5% human AB serum supplemented by 300 IU of IL-2 were added to these wells and incubated at 37° C. overnight at 5% $CO_2$. On the following day, PBMC were transferred to a second set of pre-coated retronectin retroviral vector tissue culture plates and incubated at 37° C. overnight at 5% $CO_2$. Cells were subsequently washed and re-suspended in culture media described above. Frozen leukapheresis fractions from patients NRA11 and NRA 13 (UCLA IRB#03-12-023) were thawed and incubated overnight in RPMI supplemented with 10% human AB serum and 1% penicillin, streptomycin, and amphotericin (Omega Scientific) prior to CD8+ enrichment (anti-CD8 microbeads, Miltenyi Biotech) using an AutoMACS machine according to the manufacturer's instructions. Following separation, the cells were kept at in RPMI-humanAB media containing 30 U IL2/mL.

Jurkat$^{\alpha-MART-1}$ T cells (the human T leukemia cell line Jurkat transduced with the F5 MART-1 TCR [Ref. 29] specific for peptide epitope MART-$1_{26-35}$) were then applied to the array of Example 6 and the other protein arrays using procedures such as the one exemplified in Example 3. The representative images of the arrays collected and quantified are illustrated in FIG. 10.

Figure 10:
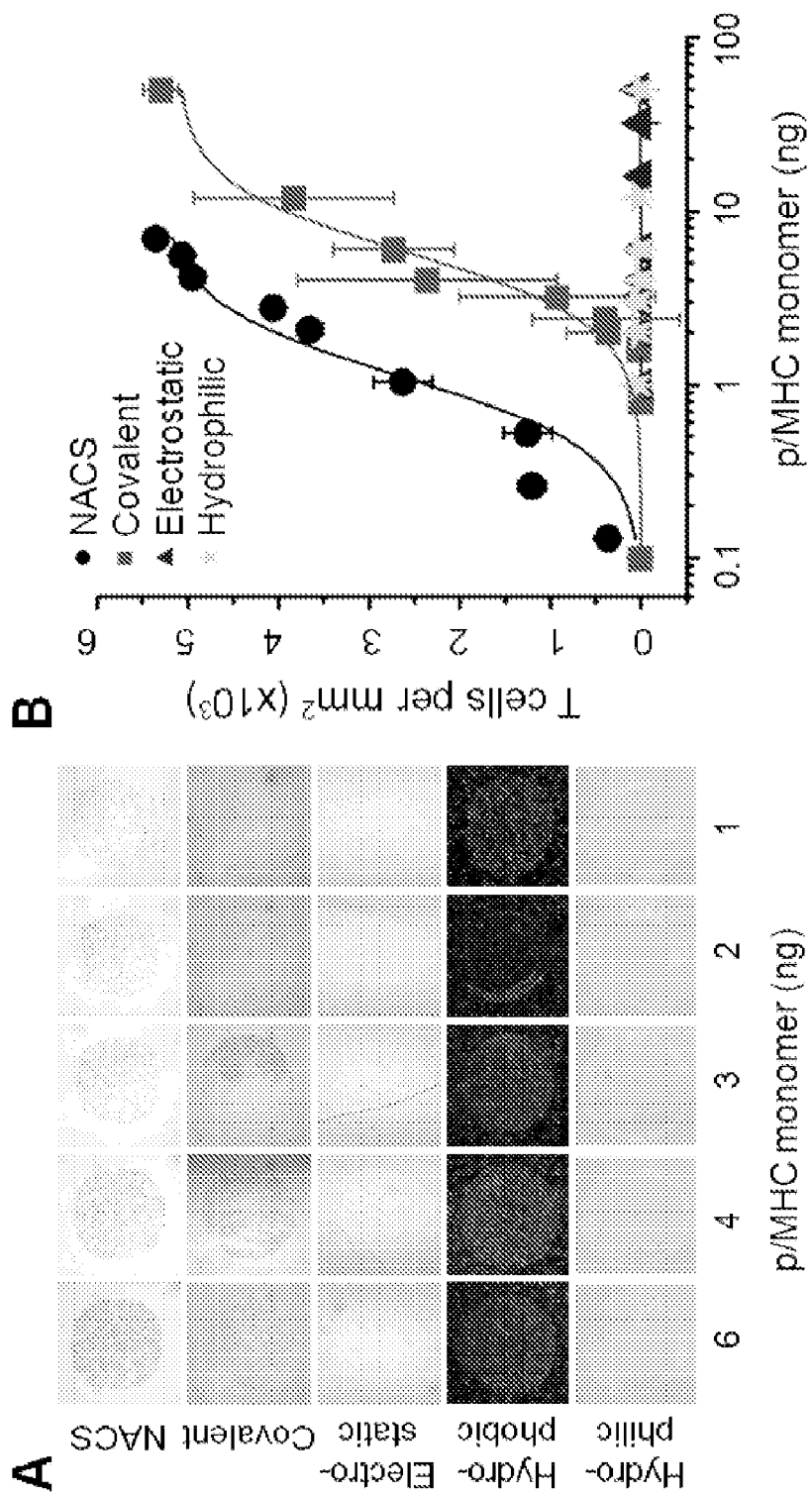
FIG. 10 shows a comparison of target capture performed with conventional protein arrays and with modular polynucleotide encoded capture agents according to an embodiment herein described. Panel A shows grayscale fluorescence images of arrays of p/MHC comprised in polynucleotide-encoded proteins further including an optimized SA scaffold compared with conventional direct p/MHC protein spotting strategies on various model substrates as indicated. Panel B shows a diagram illustrating a quantification of the data showed in Panel A. Each data point was derived from three representative spots.

In particular. the results illustrated in FIG. 10A (images collected) and FIG. 10B (images quantified) show little to no T cell capture (electrostatic, hydrophilic) or significant noise (hydrophobic) on the majority of the surfaces investigated compared to NACS arrays immobilized with identical concentrations of p/MHC tetramers. In particular, the illustration of FIG. 10A shows that while cell binding was consistent and uniform for the optimized scaffold using SAC, cell binding was observed only on one surface (covalent) but cell capture was highly variable. The illustration of FIG. 10B shows a quantification of the results of FIG. 10A. A skilled person will appreciate from the detail of FIG. 10 that to achieve equivalent cell capture densities, conventional arrays required >5 times more protein material than the SAC scaffold (see in particular quantification of FIG. 10B)

In a further series of experiments, the robustness of T cell binding performed with NACS was tested in comparison with T cell binding performed with direct spotting. In particular, p/MHC tetramers were spotted unto a derivatized surfaced (epoxy functional group) that was found to capture T cells (compared to the other surfaces in 00164 that did not bind cells). p/MHC tetramers were spotted according to manufacturer's instructions and directly compared with a NACS array assembled with the same amount of localized p/MHC protein.

Figure 11:
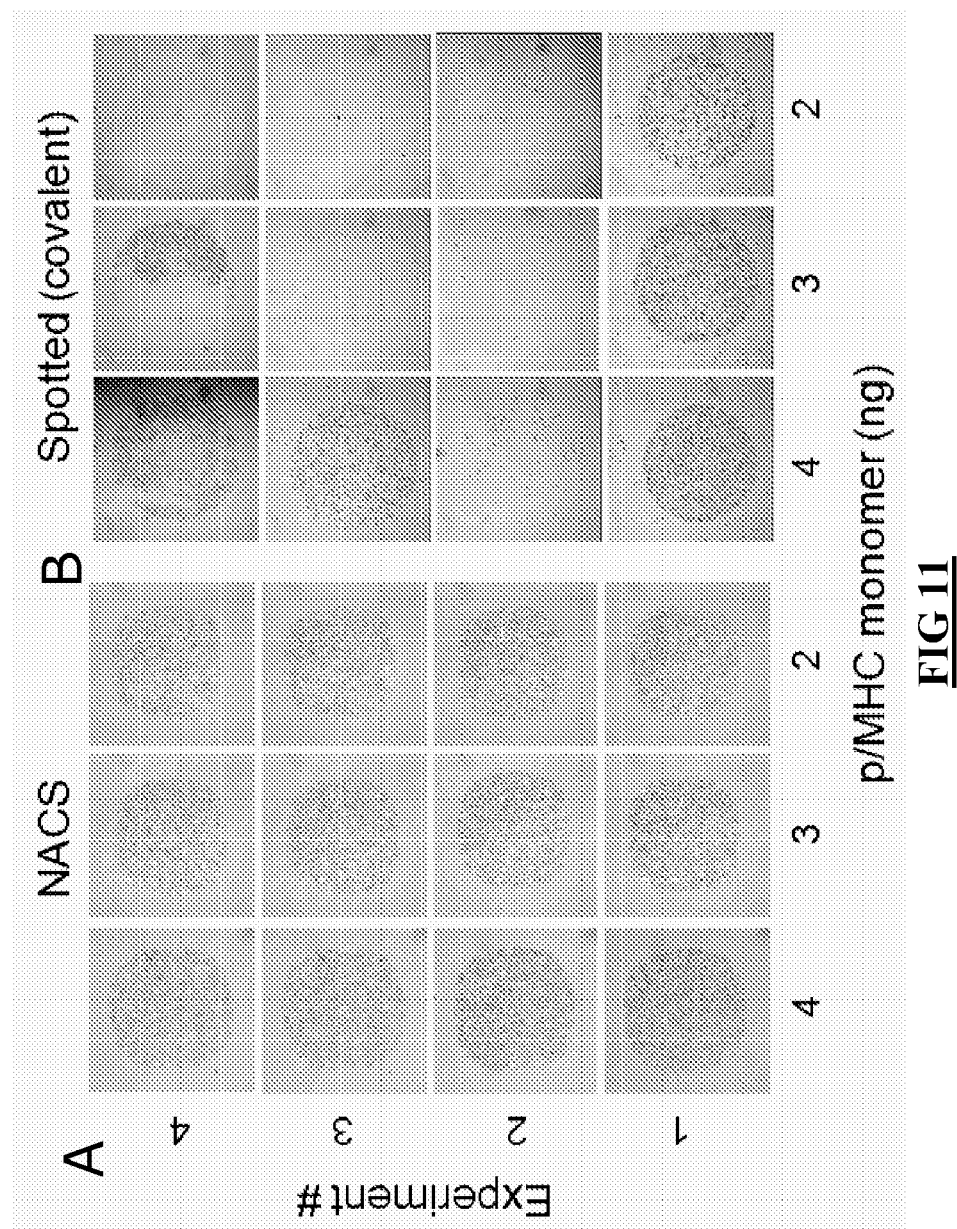
FIG. 11 shows a comparison of target capture performed with conventional protein arrays and with modular polynucleotide encoded capture agent according to an embodiment herein described. Panel A shows a grayscale version of fluorescence images of arrays of p/MHC protein comprised in an ssDNA-encoded protein further including a SAC scaffold. Each row represents a separate experiment performed on a different slide. Panel B shows a grayscale version of fluorescence images of derivatized surfaces spotted with p/MHC protein alone. Each row represents a separate experiment performed on a different slide.

The results, illustrated in FIG. 11 consistency and robustness of the SAC cell capture platform (FIG. 11A), and corresponding inconsistency of conventional approaches as evidence by the large inter-spot cell capture heterogeneity (FIG. 11B)

In particular, T cell binding on a surface (covalent) directly spotted was observed but cell capture was highly variable as evidenced by both intra-spot and inter-spot heterogeneity and the cross experimental variation illustrated (see FIG. 11B).

On the contrary, the consistency and robustness of T cell immobilization with NACS is evident from the image of FIG. 11A when compared directly with spotted arrays, which suffers from significant levels of inter-spot, intra-spot, and interexperimental heterogeneity (see FIG. 11B).

Moreover, to achieve equivalent T cell capture densities, NACS p/MHC arrays required >5 times less material than covalent immobilization. (p/MHC monomer at half max$\equiv K_{1/2}$=1.1 ng for NACS and 5.7 ng for covalent immobilization).

The performance and reproducibility of NACS p/MHC arrays is markedly improved and represents an integral step towards expanding array-based T cell detection schemes for broader applications. This likely has a few causes. First, surface-tethered ssDNA-p/MHC tetramers may enjoy greater orientational freedom at the surface/solution interface compared with adsorbed proteins which are required to conform to the surface. This effect may increase the density of functional protein and consequently reduce the amount of material required for array production. Second, the hydration state of the environment during the production and subsequent storage of protein arrays is an important factor for array reproducibility [Ref. 9, 12, 17]. This effect is minimized with NACS because DNA chips can be printed and stored dry for extended periods of time and ssDNA-tagged p/MHC tetramer arrays are self-assembled in solution immediately prior to an experiment.

Example 8

NACS Detection Specificity and Detection Sensitivity

To evaluate the specificity of p/MHC array assembly and T cell sorting, a DNA microarray was printed with the complementary strand (A) along with two additional distinct sequences (designated B and C) according to the procedure exemplified in Example 6.

NACS ssDNA-p/MHC tetramers (human HLA-A*0201 MHC molecules loaded with melanoma antigen peptide epitope tyrosinase$_{368-376}$ with pendant DNA sequence A') were hybridized to the DNA microarray so prepared.

A homogeneous population of Jurkat$^{α-Tyr}$ cells (Jurkat cells transduced with a TCR specific for tyrosinase$_{368-376}$) [Ref. 30] was then hybridized to the array according to procedure exemplified in Example 3.

Figure 12:
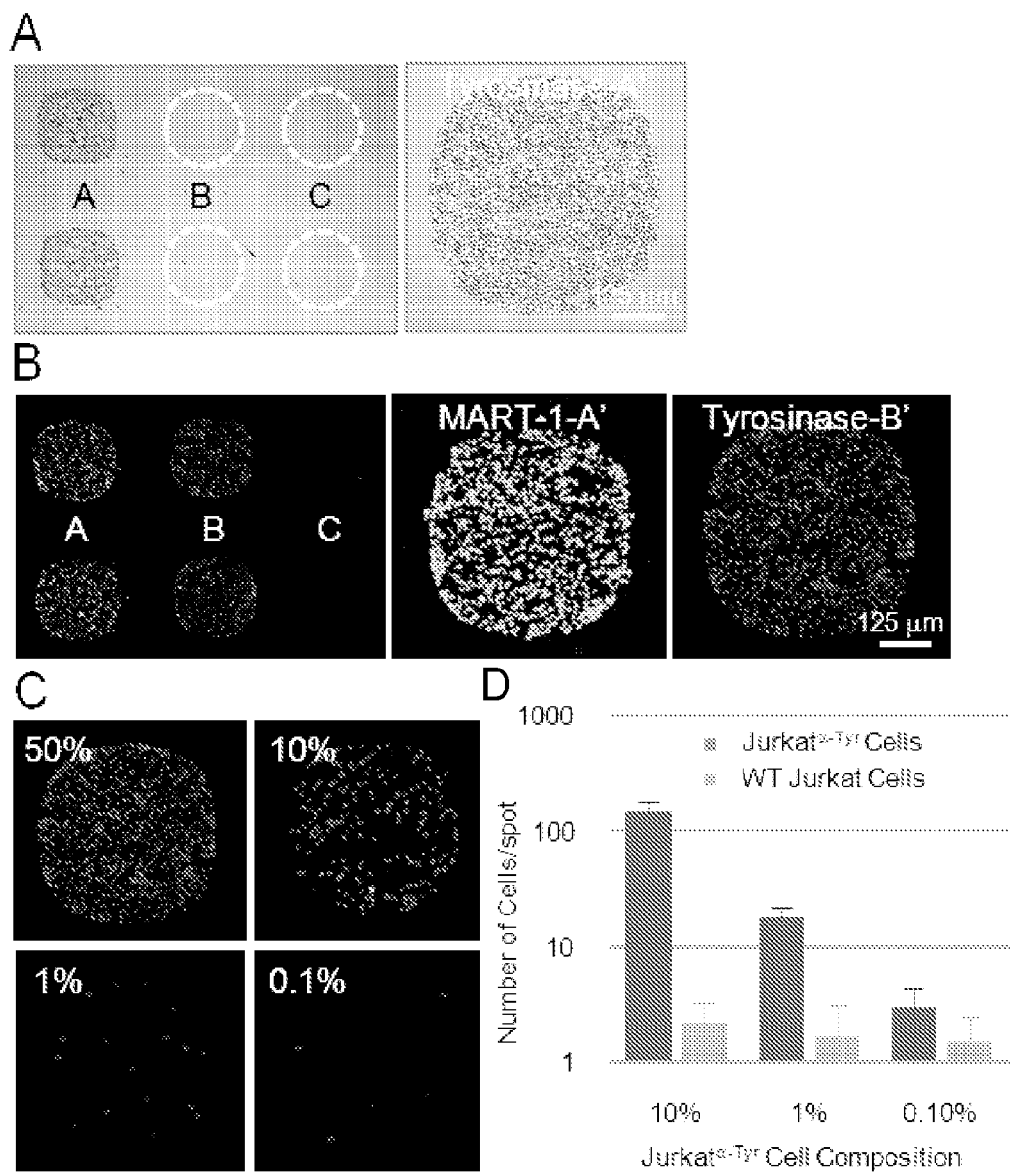
FIG. 12 shows the results of cell sorting experiments performed using modular polynucleotide-encoded capture agents according to an embodiment herein described. Panel A shows grayscale fluorescence images of an array of three different substrate polynucleotides (indicated as A, B and C) following contact with p/MHC tetramers encoded with an ss-DNA complementary to polynucleotide A and with the target provided by Jurkat$^{\alpha\text{-}Tyr}$ cells. Panel B shows grayscale fluorescence images of arrays of different substrate polynucleotides (indicated as A, B and C) following contact with p/MHC tetramers specific for Mart-1-specific TCR encoded with ss-DNA complementary to polynucleotide A, with p/MHC tetramers specific for Tyrosinase-specific TCR encoded with ss-DNA complementary to polynucleotide B and with the targets provided by mixed population of Jurkat$^{\alpha\text{-}MART\text{-}1}$ and Jurkat$^{\alpha\text{-}Tyr}$ cells prestained with lipophilic dyes (green and red respectively, illustrated in the grayscale version as light gray and dark gray). Panel C shows grayscale fluorescence images of arrays of polynucleotide encoded protein specific for Tyrosinase-specific TCR after contact with Jurkat$^{\alpha\text{-}Tyr}$ at different serial dilutions (50%, 10%, 1%, 0.1%) as indicated. Panel D shows a diagram illustrating a quantification of the data shown in Panel C.

The results, illustrated in FIG. 12 show that Jurkat$^{α-Try}$ T cells localized to the complementary spots (A) containing the hybridized cognate p/MHC but not to spots printed with the non-complementary sequences B and C (FIG. 12A The mean binding capacity calculated from three spots (~600 μm) was ~1486±62 Jurkat$^{α-Tyr}$ T cells.

To illustrate the multiplexing capability of NACS, MART-1 and tyrosinase ssDNA-p/MHC tetramers encoded to DNA sequences A and B respectively were combined and assembled simultaneously to a three element DNA microarray (strands A, B, and C). A 1:1 mixed population of Jurkat$^{α-MART-1}$ and Jurkat$^{α-Tyr}$ cells prestained with lipophilic dyes (green and red respectively illustrated in the grayscale version as light gray and dark gray) was applied to the array and localized into alternating columns (FIG. 12B). Minimal cross-reactivity was observed. The average density of spots A and B was a factor of two less than homogeneous sorting (661±19 T cells/spot) (FIG. 12B). To determine the limit of detection, target populations of Jurkat$^{α-Tyr}$ cells were spiked in at 10%, 1% and 0.1% into wild type (w.t.) Jurkat cells and sorted (FIG. 12C). The T cell capture density per spot per species for each mixture was enumerated and averaged (FIG. 12D).

The number of non-specific w.t. Jurkat cells that adhered to the array was constant throughout all dilutions while the number of Jurkat$^{α-Tyr}$ T cells captured per spot decreased linearly in relation to the fractional composition of Jurkat$^{α-Tyr}$ cells with a detection limit that was ⁻1 in 1000 cells—a limit that corresponds well to the total number of cells that can be captured per spot. Thus, the sensitivity of this approach is strictly a geometric constraint since antigen-specific T cells that settle on inert areas cannot sample and bind to their cognate p/MHC tetramer. The sensitivity can be improved by increasing the size of the capture region (i.e. increase spot diameter and/or incorporate spot redundancy) or by reducing inert regions (i.e. increase printing density).

In addition, gentle agitation or microfluidics integration could potentially allow the entire T-cell population to sample the entire protein array during cell sorting. The geometric layout of the array determines the number of antigen-specificities that can be interrogated simultaneously. In the current instance, 600 μm spots are printed in 12 by 12 grids (~1 in²), enabling the potential identification of 144 distinct antigen-specificities from 10⁶ T cells (typical number of cells required to cover 1 in² region).

Example 9

NACS Sorting and Detection of TCR Engineered Primary Human T Cells

TCR engineering of peripheral blood mononuclear cells (PBMCs) is an emerging clinical approach to rapidly generate large numbers of tumor antigen-specific T cells for adoptive transfer cell therapy in patients with melanoma and other cancers [Ref. 31, 32]. In this approach T cells are collected from a patient and transduced with a TCR specific against a target cancer antigen followed by autologous infusion. Demonstrating the feasibility of detecting TCR engineered primary human lymphocytes has importance for the clinical application of NACS.

Accordingly, in a first series of experiments, human PBMCs containing CD8+ cells were obtained from a patient via leukapheresis, expanded and transduced with a retrovirus vector containing the F5 MART-1 TCR.

The results, illustrated in FIG. 13A show a transduction efficiency greater than 90% as determined by flow cytometry.

These cells were subsequently sorted on a NACS array with MART-1 (positive control) and Cytomegalovirus (CMV pp65$_{495-503}$/HLA-A2.1, negative control) p/MHC tetramers.

In particular, the HLA-A*0201 restricted MHC class I monomers loaded with tyrosinase$_{369-377}$ (YMDGTMSQV) (SEQ ID NO:10) and MART-1$_{26-35}$ (ELAGIGILTV) (SEQ ID NO:11) were produced in house according to previous published protocols (38). A2.1-restricted EBV BMLF1$_{259-267}$ (GLCTLVAML) (SEQ ID NO:21), CMV pp65$_{495-503}$ (NLVPMVATV) (SEQ ID NO:22), murine H-2 Kb/-OVA$_{257-264}$ (SIINFEKL) (SEQ ID NO:23), and murine H-2Db/-gp100$_{25-33}$ (KVPRNQDWL) (SEQ ID NO:24) as well as all fluorescent HLA-A*0201 tetramers were purchased from Beckman Coulter. Lipophilic cell membrane staining dyes DiO, DiD, and DiL were purchased from Invitrogen.

Prior to experiments, microarray slides were blocked to prevent non-specific cell binding with 1 mg/ml PEG-NHS ester (Sunbio) in PBS for 2 hours at RT. Four-fold molar excess of p/MHC monomers were combined with ssDNA-SAC at 37° C. for 20 min ssDNA-p/MHC tetramers were hybridized to DNA arrays for 1 hour at 37° C. in 200 μl media and rinsed with 3% FBS in PBS. T cells (10⁶/100 μl media) were incubated on the array at 37° C. for 30 min The arrays were rinsed with 3% FBS in PBS and cell capture visualized via brightfield (Nikon Eclipse TE2000) and/or confocal microscopy (Nikon E800). Post T cell capture p/MHC tetramer staining was done by incubating the array with 200 μl of media containing fluorescent p/MHC tetramer along with fluorescent cDNA (Cy5-A' and/or Cy3-B'). The arrays were rinsed with 3% FBS in PBS prior to imaging. For selective T cell release experiments, three identical arrays were used to immobilize cells. Treatment with EcoRI, BamHI, or DNase was in RPMI media for 1-2 hours at 37° C. DNase was purchased from Sigma, all other enzymes from NEbiolabs.

For p/MHC comparative studies, SuperEpoxy and SuperProtein (representing covalent and hydrophobic surfaces respectively) were purchased from Arrayit (Sunnyvale, Calif.). Amine GAPS II slides (electrostatic) were purchased from Corning. Polycarboxylate hydrogel (hydrophilic) slides were purchased from XanTec (Germany). Fluorescent MART-1 tetramers were printed according to manufacturer's instructions for each slide. Cell sorting images were quantified with ImageJ (NIH) and fitted to the Hill Function (NACS n=2, R2=0.95, Covalent n=2.1, R2=0.97) with Origin (OriginLab, MA).

The transduced T cells were immobilized to the MART-1 regions only. The antigen-specificity of the captured cells was doubly validated by staining with fluorescent MART-1 and CMV p/MHC tetramers (red and blue respectively) after the cells were immobilized on the arrays.

The results illustrated in FIG. 13B and FIG. 13C show that no cells were stained specific for CMV (see dotted circles in FIG. 13B) and that the cell capture was specific (see overly of confocal and brightfield images of FIG. 13C)

Example 10

NACS Sorting and Detection of Endogenous Primary Human T Cells

NACS detection of primary human T cells isolated from peripheral blood was performed. This is because, in general detection of primary human T cells isolated from peripheral blood is generally more demanding than cultured cell lines because a single population of antigen-specific T cells is present within a large background of differing blood cells and of T cells expressing monoclonal and polyclonal TCRs of diverse specificities. In addition, these T cells would be expressing endogenous levels of TCR. Applicants explored whether the same attributes of NACS that were found in the above examples would apply equally to endogenous primary human T cells.

Frozen leukapheresis samples from patients NRA11 and NRA13 were CD8+ enriched and prior to NACS sorting.

Quantity and specificity of EBV specific and CMV specific T cells in patient NRA11 and NRA13 were stained with fluorescent EBV and CMV p/MHC tetramers and analyzed by flow cytometry The results, illustrated in FIG. 14, show that lymphocytes isolated from NRA13 contained significant levels of EBV specific T cells (4.9%) with minimal CMV specific T cells. (see FIG. 14A) while Lymphocytes isolated from NRA11 contained high levels of CMV specific T cells (9%) with a low population of EBV-specific cells (0.12%) (see FIG. 14B).

Following this determination, the leukaphersis from patient NRA11 and NRA 13 were analyzed with NACS technology in one-target detection and a multiplexed detection experiments.

For the one target detection experiments, frozen leukapheresis samples from patient NRA13 were CD8+ enriched and applied to a CMV and Epstein-barr virus (EBV BMLF1$_{259-267}$/HLA-A2.1) p/MHC array provided by the procedure of Example 6.

For multiplexed detection, a 1:1 mixture of EBV-specific and CMV-specific CD8+ T cells was produced by combining NRA13 lymphocytes with CMV-specific T cells from patient NRA11 and the mixture applied to a CMV and Epstein-barr virus (EBV BMLF1$_{259-267}$/HLA-A2.1) p/MHC array provided by the procedure of Example 6.

The results illustrated in FIG. 15 show that in both experiments T cells were selectively and quantitatively detected. In particular, in the detection performed with leukepheresis of patient NRA13 only T cells were captured within the EBV regions only (see FIG. 15A). T cells detected from a 1:1 mixture of NRA11 and NRA 13 (left panel) were verified to be specific for EBV and CMV. In particular, following NACS cell sorting and fluorescent p/MHC tetramer staining, the populations were complementary stained for the appropriate antigen-specificity (FIG. 15B).

T cells from patient NRA 13 were serially diluted to create mixtures of cells that contained EBV-specific T cells (~0.4%, 0.2%, and 0.1% by FACS (FIG. 14C). The three mixtures of EBV specific T cells were detected on a array encoded with EBV/HLA-A2.1 tetramers, represented in FIG. 15D The results, illustrated in FIGS. 15C and 15D show that isolated hits were resolved in frequencies as low as ~0.1% (FIG. 15D, dark grey arrows). The number of unstained cells within the capture regions (black arrow) was constant throughout all dilutions (~1-2 cells/spot) and likely represents the level of background from non-specific interactions.

It should be noted that while we incorporated fluorescent p/MHC tetramer staining after T cell immobilization for illustrative purposes, the specificity of the captured cells could be determined solely from the registry of the array.

Example 11

Controlled and Selective Release Through Restriction Endonucleases of T Cells Immobilized Using NACS Approach Antigen-specific T cells immobilized onto glass are immediately available for secondary assays, since many such as immunohistochemistry (IHC), fluorescent in situ hybridization (FISH) and cytokine secretion assays [Ref. 5, 7] are traditionally performed or are compatible with cells localized to a substrate. However, several other relevant assays, such as those designed to assess T cell phenotype or functional status like genomic/mRNA analysis or simply, further culture for phenotypic enrichment would require a method for releasing the captured cells. Any release scheme should ideally be selective for given cell types. For NACS, Applicants explored whether the DNA tethers could be selectively cleaved by exploiting the sequence specificity of restriction endonucleases.

Applicants integrated unique restriction sites to each DNA sequence employed for cell sorting (see Example 6 above), and found that the adhesion of different populations of antigen-specific T cells could, in fact, be independently controlled (FIG. 16b).

In particular oligonucleotides A and B of Example 6 were modified by incorporating 6 bp restriction sites specific for endonucleases EcoRI and BamHI respectively thus obtaining oligonucleotides $A_{EcoRI}$ and $B_{BamHI}$ following the approach schematically illustrated in FIG. 16A.

DNA microarrays were therefore printed with orthogonal sequences containing EcoRI and BamHI restriction sites. Jurkat$^{a\text{-}MART\text{-}1}$ and Jurkat$^{\alpha\text{-}Tyr}$ cells prepared as exemplified in Example 7 and prestained with lipophilic dyes (red and green respectively) were then sorted on an array printed with DNA sequences $A_{EcoRI}$ and $B_{BamHI}$ according to a procedure exemplified in Example 6.

The results illustrated in FIG. 16B show sorting of $A_{EcoRI}$ and $B_{BamHI}$ as well as correct release of a selected target following treatment with the corresponding restriction enzyme.

In particular, the cell were first immobilized on the array as illustrated in FIG. 16Bi where the red dye is shown as dark gray and the green dye is shown as light gray.

After T cell immobilization, the array was treated with BamHI which cleaved the $B_{BamHI}$ spots and selectively released the bound Jurkat$^{\alpha\text{-}Tyr}$ cells (FIG. 16Bii). Conversely, on a separate but identical array, Jurkat$^{a\text{-}MART\text{-}1}$ cells were released after treatment with EcoRI (FIG. 16Biii). A second round of enzymatic treatment with the complementary endonuclease (EcoRI to state (ii) or BamHI to state (iii)) removed the remaining adherent cells (FIG. 16Biv). Alternatively all captured cells (i) could be released non-selectively in a single step with the addition of DNase (data not shown).

Example 12

Procedure for Performing NACS Detection of Targets Captured in Solution

Target population of cells can be captured according to a procedure where the encoded capture agent is contacted with a target before binding the substrate.

An exemplary series of experiments performed according to this approach is illustrated in FIG. 17. The biomarkers of interest in a biological sample can bind to polynucleotide-encoded capture agents in solution. After binding, the entire sample can be applied to a substrate printed with the cDNA. The biological sample, upon application to the substrate, with localize to spatially distinct locations mediated by DNA hybridization. The cargo bound to the polynucleotide-encoded capture agents can then be identified using convention fluorescent and other visualization techniques identifiable by the skilled reader.

In the experiments of FIG. 17, encoded-polynucleotide capture agents can be used to bind to biological targets on cell surfaces in solution. This is demonstrated in panel A, in which fluorescent polynucleotide-encoded tyrosinase/HLA-A2.1 p/MHC tetramers were used to stain Jurkat$^{\alpha\text{-}Tyr}$ cells and analyzed with flow cytometry. This was directly compared with fluorescent tyrosinase/HLA-A2.1 p/MHC tetramers. Both reagents stained Jurkat$^{\alpha\text{-}Tyro}$ with equal intensities. Jurkat$^{\alpha\text{-}Tyro}$ cells prestained with polynucleotide-encoded tyrosinase/HLA-A2.1 p/MHC tetramers were captured and detected on an array mediated by DNA hybridization (panel B). Please provide description of the results with reference to the figure.

Example 13

Additional Optimized Scaffolds Capture Agents Comprising a Protein Binding Molecule Additional optimized scaffolds can be provided by Protein A, Protein G, and Protein A/G which is a family of bacterial recombinants that bind to the Fc domain of all subclasses IgG, and in limited extent to IgA, IgE, IgM and IgD. In particular, these proteins can serve as an un-optimized scaffold in the embodiment where DNA is attached randomly to free lysine residues on the surface of the protein via NHS-amide coupling chemistry. The binding proteins are IgG antibodies against a desired biomarker (e.g. CD3 found on T cells). Molar excess of IgG antibodies can be incubated with ssDNA-Protein A/G and employed to sort and capture biological targets of interest (e.g. anti-CD3—proteinA/G-ssDNA conjugates can be used to sort out T cells from a complex mixture of cells).

Figure 18:
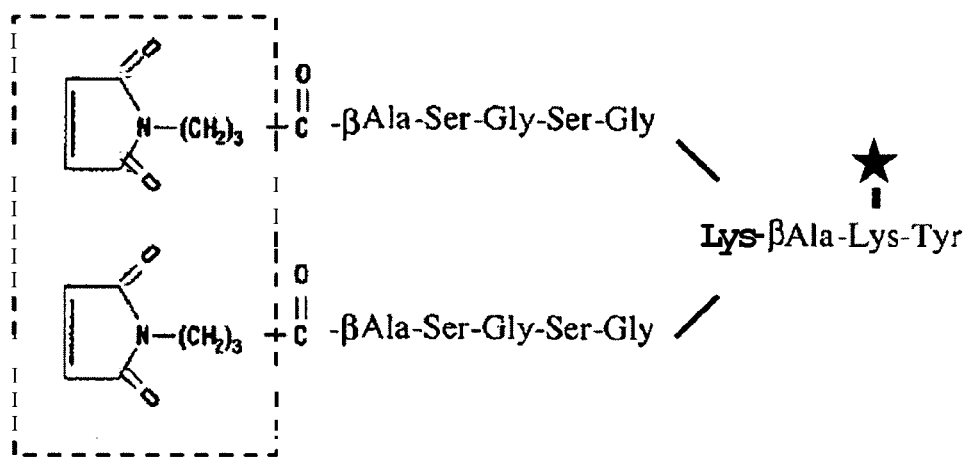
FIG. 18 shows a schematic of a branched peptide. The reactive primary amine is highlighted by a "star" and the thiol reactive maleimide groups are highlighted by a dashed box.

Illustrated in FIG. 18 is a hypothetical figure of a branched peptide. Here the length of the peptide is 9 amino acids, stretching from the N-terminal alanine to C-terminal tyrosine residues. There is a branch point at the lysine residue in position 4 from the C-terminus to provide a two-fold valency to this scaffold. The reactive maleimide groups at the N-terminus is the chemical handle to attach two binder proteins with free thiols, and the encoding-polynucleotide can be attached to the lysine residue next to the c-terminal tyrosine residue via NHS-amide coupling. Because the attachment sites for the binder proteins and the encoding-polynucleotide are separated with this branched-peptide approach, the resulting capture agent is fully polar and optimized Exemplary binder molecules can be RGD peptides containing cysteine residues (Anaspec, #29897). The targets to detect include cells which express integrin receptors (ATCC, #CCL-92).

Another optimized protein scaffold is the protein SAC3 which is represented by the primary amino acid sequence:

```
                                           (SEQ ID NO: 25)
HMGITGTWYNQLGSTFIVTAGADGALTGTYESAVGNAESRYVLTGRYDS

APATDGSGTALGWTVAWKNNYRNAHSATTWSGQYVGGAEAMNTQWLLTS

GTTEANAWKSTLVGHDTFTKVGGSGCGGSGCGGSGCP
```

Figure 19:
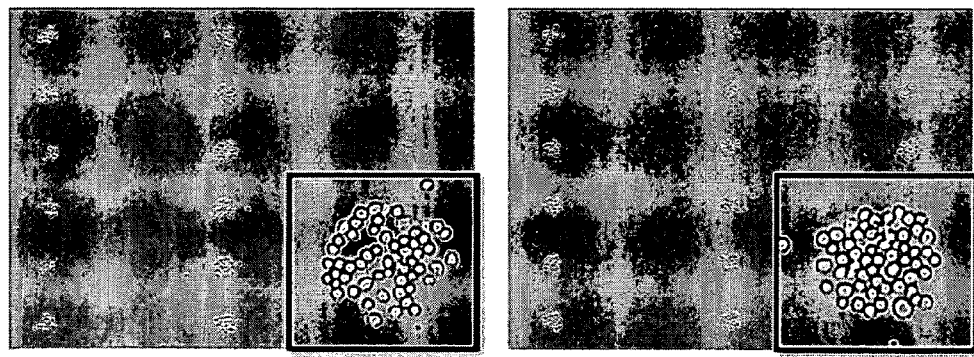
FIG. 19 shows the detection of Jurkat$^{\alpha\text{-}Tyr}$ T cells using tyrosinase368-376/HLA-A2.1 tetramers encoded to strand A' made from the optimized protein scaffolds SAC (left panel) and SACS (right panel).

This alternate optimized streptavidin scaffold contains 3 cysteine residues at the c-terminus for site specific attachment of the encoding-polynucleotide. By combining with molar excess of biotinylated p/MHC (tyrosinase/HLA-A2.1) with ssDNA-SAC3, the resulting capture agent can be used to target T cells from a complex mixture. In FIG. 19, the efficiency of T cell capture (Jurkat$^{\alpha\text{-}Tyro}$) of the optimized scaffold SAC3 (right panel) is directly compared with the optimize scaffold SAC. The cell capture efficiency is identical.

Any form of optimization scheme of SA will preserve the 4:1 ratio binding with biotin. Applicants have provided more than one SA optimized and different optimized SA work differently for certain target. The scaffold is eventually selected in view of the ability to bind the target. Branched peptides, such as the one exemplified in FIG. 18 can be used as a multimeric scaffold alternative to SA bind, we can have monomeric or dimeric or n meric as well depends on the experimental design.

Example 14

Capture Agents Comprising a Protein Binding Molecule

Alternative binder proteins and scaffolds can be employed. Integrins are heterodimeric cell surface receptors that bind to extracellular matrix proteins generally consisting of the peptide motif arginine-glycine-aspartate. Biotinylated peptides containing the RGD motif can be purchased from Anaspec (#62347). These peptide binding molecules can be assembled with an optimized scaffold like SAC-A and used to sort cell populations contain target cells expressing integrins, including 3T3 fibroblasts (ATCC, #CCL-92).

Example 15

Capture Agents Comprising a Linker

The linker serves to connect the binding protein to the scaffold. This can be composed of a peptide sequence. For example, the linker GGGLNDIFEAQKIEWHE (SEQ ID NO: 26) can be appended to the C-terminus of a HLA-A2.1 MHC molecule. A biotin molecule can be attached to the resulting linker with the enzyme BirA ligase. This biotinylated p/MHC construct can be used in conjunction with an optimized A-SAC scaffold to sort antigen specific cells on a cDNA printed substrate.

Another linker can be composed of the peptide LCTPSRGSLFTGR (SEQ ID NO: 27) which can also be appended to the c-terminus of binding proteins like MHC molecules. The glycine residue can be modified to an aldehyde group with the enzyme formylglycine generating enzyme (FGE). Scaffolds containing hydrazide (R—NH—NH2) (e.g. reacting SANH (Succinimidyl 6-hydrazinonicotinate acetone hydrazone, Solulink) with the scaffold SA) can be used to attach the aldehyde-MHC binder protein.

An example of a linker can be the poly-uracil RNA sequence UUUUUUUUUU (SEQ ID NO: 28). This linker can be cleaved in the presence of RNase A, an endoribonuclease that cleaves the 3' end of unpaired (i.e. single stranded) C and U residues.

Example 16

ImmunoPCR to Profile Surface Markers of Cells Capture with NACS

Figure 20:
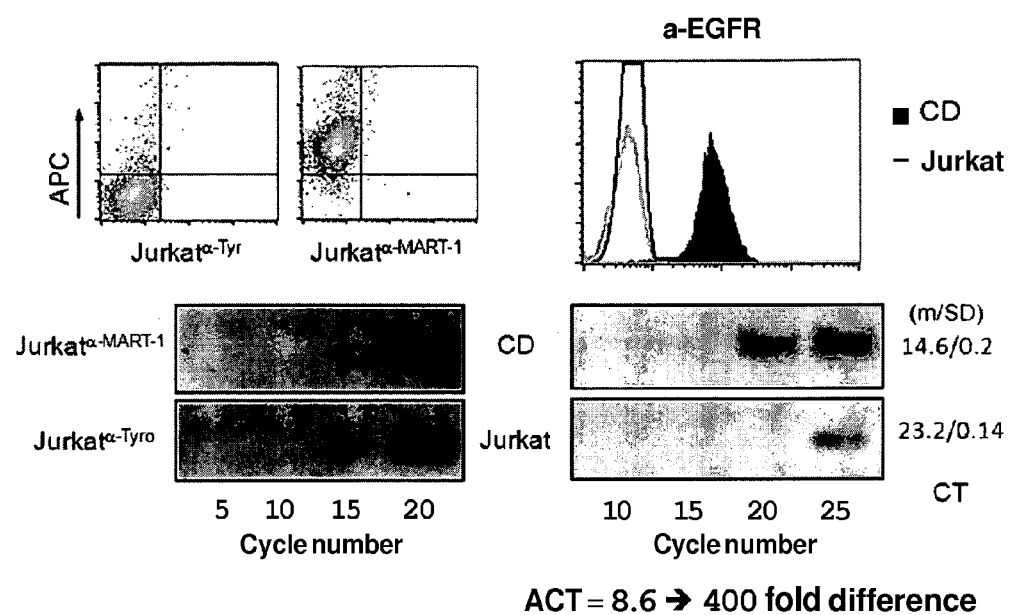
FIG. 20 shows the detection of cell surface receptors using immuno-PCR. Panel A shows the flow cytometry analysis of Jurkat$^{\alpha\text{-}MART\text{-}1}$ and Jurkat$^{\alpha\text{-}Tyr}$ T cells stained with fluorescent MART-1 p/MHC tetramers encoded with ssDNA. Panel B shows flow cytometry analysis of CD glioma cells and Jurkat T cells stained with fluorescent anti-EGFR antibodies labeled encoded with ssDNA. The bottom panels illustrate the detection of the cognate cell receptor (a-MART-1 TCR, panel C; EGFR, panel D) by amplifying the encoded ssDNA with PCR.

T cells that are captured on an array can be analyzed further. One analytical assay is immunoPCR [Ref. 51]. Here antibodies labeled with distinct DNA tags (DEAL conjugates) are used to bind to a target of interest, which in this example, is a biomarker expressed on the cell surface. After binding, the DNA tag on the antibody can be amplified and detected using PCR. While this has been shown to work with protein from solutions, Applicants show that this concept is feasible when the biomarker is confined to a cell surface. A cell line expressing EGFR (CD cells) and a cell line with null expression of EGFR (Jurkat cells) as shown by FIG. 20 (top right panel, validated by flow cytometry) are both stained with α-EGFR-ssDNA DEAL conjugate. After staining the tag on the EGFR antibodies were amplified with PCR and Q-PCR (lower panels). The presence of the tags was detected within 14.6 cycles (CD cells) and 23.2 cycles (Jurkat cells). This corresponds to a signal to noise of ~400:1.

In parallel, p/MHC tetramers encoded with DNA were used to detect the presence of a TCR on T cells. Two cell lines, one expressing a TCR specific for the MART-1 antigen (Jurkat$^{\alpha\text{-}MART1}$) and another cell line expressing a TCR specific for Tyrosinase antigen (Jurkat$^{\alpha\text{-}Tyr}$, both cell lines were verified by staining with fluorescent p/MHC tetramers and analyzed by flow cytometry, FIG. 20, top left panel) were stained with MART-1/HLA-A2.1 p/MHC tetramers encoded with DNA. The DNA tag was amplified by PCR and detected with gel electrophoresis. Jurkat$^{\alpha\text{-}Mart\text{-}1}$ cells were detected within 15 cycles, while the Jurkat$^{\alpha\text{-}Tyr}$ cells that did not express the cognate TCR appeared within the gel at around 10 cycles. Thus the presence of the MART-1 specific TCR was detected specifically.

Example 17

Dynamic Functional Profiling of T Cells Using NACS and DEAL Conjugates

Figure 22:
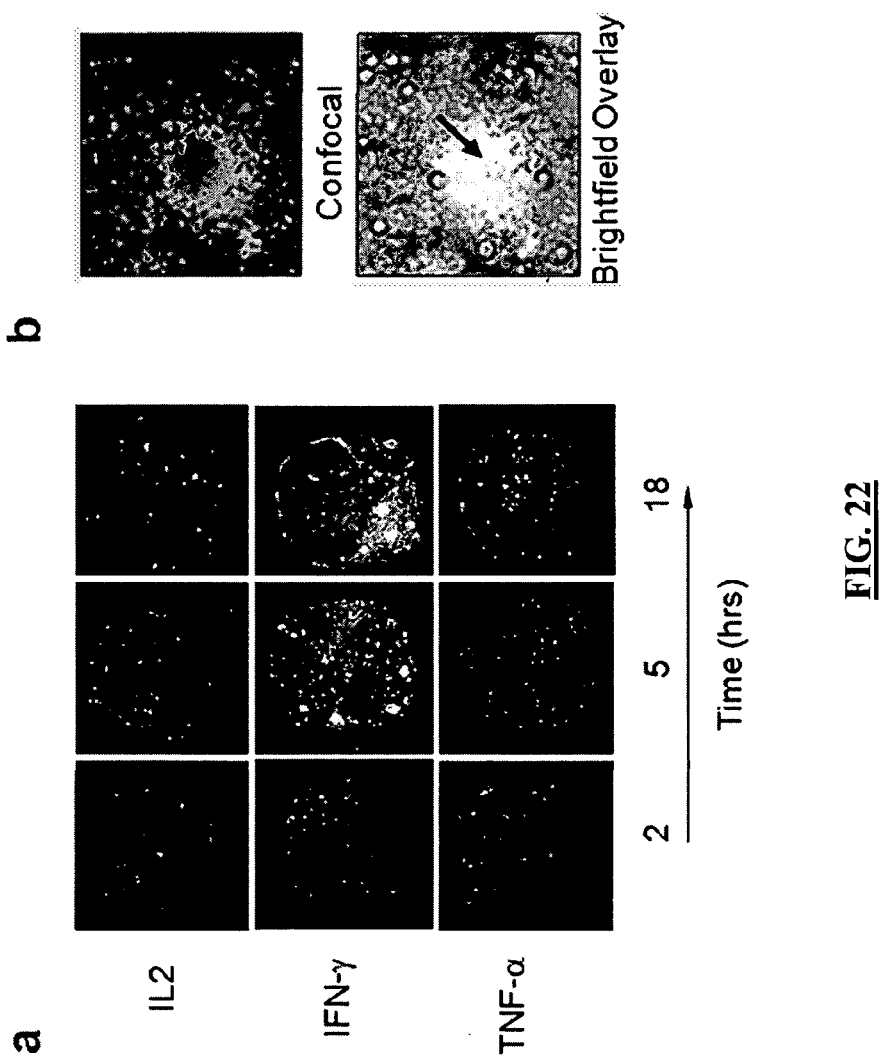
FIG. 22 shows functional profiling of antigen specific T cells captured and activated on a glass substrate. Panel A contain the fluorescent images of individual spots encoded with three different cytokines at three different time points. Panel B shows fluorescent magnifications of one individual IFN-y cluster.

Applicants proceeded by integrating an ELISPOT-type sandwich assay with p/MHC NACS to detect cytokines produced by captured murine TCR transgenic splenocytes "on-the-spot" (FIGS. 21, 22). Three murine anti-cytokine antibodies (IL-2, IFN-y and TNF-a) were encoded with DNA strands A', B', and C' respectively. H-2Kb-OVA257-264 ssDNA-p/MHC tetramers were encoded to all three strands. The ssDNA-p/MHC tetramers and antibody conjugates were pooled and assembled to a microarray printed with the complementary strands A, B and C. Murine OT1 lymphocytes (derived from TCR transgenic mice in which most splenocytes are specific for the model antigen OVA257-264), were then seeded on the array. Following incubation periods of 2, 5, or 18 hours, pooled cytokine detection antibodies were added and the slide imaged by confocal microscopy (FIG. 22A). The inflammatory cytokine IFN-y was detected at time points 5 and 18, manifest as discrete diffusive clusters (~50-100 μm in diameter at 5 hrs) that increased in average diameter temporally, attributable to molecular diffusion and sustained secretion. Examination of the local vicinity of each burst showed that underlying each fluorescent cluster was a single cell while neighboring cells appeared to be non-responders (FIG. 22B), suggestive that each IFN-y burst was derived from a single cell. The number of IFN-y clusters remained constant at ~3 between hours 5 and 18, indicating no increase in the number of activated T cells between those hours. No significant levels of murine IL-2 and TNF-a were detected at these time points.

In the preceding examples, the Applicants have described a method for generating robust and modular p/MHC arrays for high efficiency target detection and sorting, exemplified with particular reference to T cells. The inclusion of a larger set of orthogonal DNA sequences [Ref. 19, 24] will enable the modular assembly of higher order p/MHC arrays for T cell screening experiments (e.g. one working set of DNA sequences can be used interchangeably to generate any combination of p/MHC arrays). This would find immediate utility in the field of TCR peptide epitope discovery where recently, novel antigen peptides were discovered via high-throughput CD8+ screening experiments utilizing multi-color flow cytometry in mice and humans [Ref. 33, 34] (as many as 2,000 distinct p/MHC tetramers were prepared and tested).

NACS arrays are expected to streamline such experiments. Although certain traditional methods of producing single p/MHC monomers are time and labor intensive, recent reports using conditional peptide exchange technology enables the relatively straightforward construction of 1000 element p/MHC libraries rapidly [Ref. 34-36]. The integration of NACS with these peptide exchange technologies is a realistic option. NACS arrays outperform conventional spotted arrays assessed in key criteria such as repeatability and homogeneity. The versatility of employing DNA sequences for cell sorting is exploited to enable the programmed, selective release of target populations of immobilized T cells with restriction endonucleases for downstream analysis. Because of the performance, facile and modular assembly of p/MHC tetramer arrays, NACS holds promise as a versatile platform for multiplexed T cell detection.

Applicants have also demonstrated a number of advantages of the NACS platform. It significantly outperforms certain literature approaches that utilize surface-bound p/MHC tetramers to capture cells. It is a simple and inexpensive to implement since cell sorting is performed on glass substrates prepared via traditional DNA printing technologies. In addition, sorted cells may be selectively released, which should permit for the deployment of a host of bioanalytical methods on NACS sorted cells.

Applicants expect that NACS will find uses beyond multiplexed sorting of T cells based on TCR specificity. The principal components of the platform used in the preceding examples—streptavidin-cysteine core and orthogonal single stranded DNA sequences—were rationally developed to enable oriented coupling and spatial addressing. Thus this platform is amenable to any family of binding proteins or small molecule binders labeled with biotin. The increase in avidity of p/MHC tetramers over monomers as a consequence of the valency of SA should likewise extend to other capture agents, making it feasible to generate cellular arrays with probes ranging from high to moderate affinities like antibodies, aptamers or peptides.

In particular, the NACS approach can be used in therapeutic and/or diagnostic applications involving MHC complexes. The MHC complex consists of a fragment of an antigen (a peptide) lying within the groove of a major histocompatibility complex (MHC) molecule. A portion of the TCR has affinity for the MHC, and a variable portion has an affinity for the peptide antigen. This peptide may be a very short fragment (<<10 amino acids long), and so the affinity between the TCR and the MHC/antigen may be weak. Nevertheless, for many fundamental and clinical purposes, sorting T-cells by their antigen specificity is critically important. Such sorting can be used to determine how the immune system is responding to some disease, such as an infection or a cancer. It is also a key part of various immunotherapies that find applications in the treatment of certain cancers, such as melanoma. In that case, T-cells from a patient are collected, they are genetically modified so that they become antigen-specific T-cells that are encoded to identify and kill certain cancer cells.

Once modified, those T-cells are put back into the patient. All of the steps in this therapy involve sorting T-cells, but the last step—identifying which T-cells have evolved into antigen specific T-cells, involves sorting of the T-cells by their antigen specificity. High affinity reagents that can sort the various antigen specific T-cells from a complex mixture are central to such therapies.

Other examples exist in which it is desirable to sort cells by various membrane proteins, but those membrane proteins do not provide a good 'handle' for antibody-based sorting methods.

An example is cancer cells that express a genetic mutant of the EGFR protein called EGFR-VIII. EGFR-VIII is an oncoprotein—meaning that it is an important genetic mutation that can lead to cancer. However, it is also a membrane protein in which most of the extracellular portion of that protein has been cleaved. The remaining portion represents a small 'handle', and so antibodies to EGFR-VIII exhibit only a weak affinity for that protein. The multiplexed sorting of cells within a tumor by various cancer-related proteins such as EGFR, EGFR-VIII, etc., can provide key diagnostic information about the cancer, which in turn can be utilized to direct therapies or combination therapies.

In summary, in several embodiments provided herein are polynucleotide-encoded capture agents for target detection and in particular modular polynucleotide-capture agents comprising a target binding component, a scaffold component and an encoding component formed by standardized molecular units that can be coupled and decoupled in a controlled fashion, and related compositions methods and systems.

The examples set forth above are provided to give those of ordinary skill in the art a complete disclosure and description of how to make and use the embodiments of the, capture agents, devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Detailed Description, and Examples is hereby incorporated herein by reference. Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although specific methods and materials are described in the present disclosure, any methods and materials similar or equivalent to those described herein can be used in the practice for testing of the specific examples described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1) Altman, J. D.; Moss, P. A. H.; Goulder, P. J. R.; Barouch, D. H.; McHeyzer-Williams, M. G.; Bell, J. I.; McMichael, A. J.; Davis, M. M. *Science* 1996, 274, 94-96.
2) Matsui, K.; Boniface, J. J.; Steffner, P.; Reay, P. A.; Davis, M. M. *Proc. Natl. Acad. Sci. USA* 1994, 91, 12862-12866.
3) McLaughlin, B. E.; Baumgarth, N.; Bigos, M.; Roederer, M.; DeRosa, S. C., Altman, J. D.; Nixon, D. F.; Ottinger, J.; Oxford, C.; Evans, T. G.; Asmuth, D. M. *Cytometry A* 2008, 73, 400-4010.
4) Chattopadhyay, P. K.; Price, D. A.; Harper, T. F.; Betts, M. R.; Yu, J.; Gostick, E.; Perfetto, S. P.; Goepfert, P.; Koup, R. A.; De Rosa, S. C.; Bruchez, M. P.; Roederer, M. *Nat. Med.* 2006, 12, 972-977.
5) Chen, D. S.; Soen, Y.; Stuge, T. B.; Lee, P. P.; Weber, J. S.; Brown, P. O.; Davis, M. M. *PLoS Med.* 2005, 2, 1018-1030.
6) Soen, Y.; Chen, D. S.; Kraft, D. L.; Davis, M. M.; Brown, P. O. *PLoS Biol.* 2003, 1, 429-438.
7) Stone, J. D.; Dernkowicz, W. E.; Stem, L. J. *Proc. Natl. Acad. Sci. USA* 2005, 102, 3744-3749.
8) Deviren, G.; Gupta, K.; Paulaitis, M. E.; Schneck, J. P. *J. Mol. Recognit.* 2007, 20, 32-38.
9) Haab, B. B.; Dunham, M. J.; Brown, P. O. *Genome Biology* 2001, 2, 1-13.
10) Butler, J. E.; Ni, L.; Brown, W. R.; Joshi, K. S.; Chang, J.; Rosenberg, B.; Voss Jr, E. W. *Mol. Immunol.* 1993, 30, 1165-1175.
11) Butler, J. E.; Ni, L.; Nessler, R.; Joshi, K. S.; Suter, M.; Rosenberg, B.; Chang, J.; Brown, W. R.; CantareroButler, L. A. *J Immunol. Methods,* 1992, 150, 77-90.
12) MacBeath, G.; Schreiber, S. L. *Science* 2000, 289, 1760-1763.
13) Lesaicherre, M. L.; Lue, Y. P. R.; Chen, G. Y. J.; Zhu, Q.; Yao, Q. J. *Am. Chem. Soc.* 2002, 124, 8786.
14) Peluso, P.; Wilson, D.; Do, D.; Tran, H.; Venkatasubbaiah, M.; Quincy, D.; Heidecker, B.; Poindexter, K.; Tolani, N.; Phelan, M.; Witte, K.; Jung, L.; Wagner, P.; Nock, S. *Anal. Biochem.* 2003, 312, 113-124.
15) Kwon, Y.; Han, Z.; Karatan, E.; Mrksich, M.; Kay, B. K. *Anal. Chem.* 2004, 76, 5713-5720.
16) Arenkov, P.; Kukhtin, A.; Gemmel, A.; Voloshchuk, S.; Chupeeva, V.; Mirzabekov, A. *Anal. Biochem.* 2000, 278, 123-131.

17) Kiyonaka, S.; Sada, K.; Yoshimura, I.; Shinkai, S.; Kato, N.; Hamachi, I. *Nat. Mater.* 2004, 3, 58-64.
19) Bailey, R. C.; Kwong, G. A.; Radu, C. G.; Witte, O. N.; Heath, J. R. *J Am. Chem. Soc.* 2007, 129: 1959-1967.
20) Boozer, C.; Ladd, J.; Chen, S. F.; Jiang, S. T. *Anal. Chem.* 2006, 78, 1515-1519
21) Niemeyer, C. M. *Nano Today* 2007, 2, 42-52.
22) Chandra, R. A.; Douglas, E. S.; Mathies, R. A.; Bertozzi, C. R.; Francis, M. B. Angew. *Chem. Int. Ed. Engl.* 2006 45, 896-901.
23) Hsiao, S. C.; Crow, A. K.; Lam, W. A.; Bertozzi, C. R.; Fletcher, D. A.; Francis, M. B. *Angew. Chem. Int. Ed. Engl.* 2008, 47, 8473-7.
24) Fan, R.; Verrnesh, O.; Srivastava, A.; Yen, B. K. H.; Qin, L.; Ahmad, H.; Kwong, G. A.; Liu, C. C.; Gould, J.; Hood, L.; Heath, J. R. *Nat. Biotechnol.* 2008, 26, 1373-1378
25) Ramachandiran, V.; Grigoriev, V.; Lan, L.; Ravkov, E.; Mertens, S. A.; Altman, J. D. *J. Immunol. Methods* 2007, 319, 13-20.
26) Cameron, T. O.; Cochran, J. R.; Yassine-Diab, B.; Sekaly, R. P.; Stem, L. J. *J. Immunol.* 2001, 166, 741-745.
27) Reznik, G. O.; Vajda, S.; Cantor, C. R.; Sano, T. *Bioconj. Chem.* 2001, 12, 1000-1004.
28) Green, N. M. *Methods Enzymol.* 1970, 18, 418-424.
29) Johnson, L. A.; Heemskerk, B.; Powell, D. J.; Cohen, C. J.; Morgan, R. A.; Dudley, M. E.; Robbins, P. F.; Rosenberg, S. A. *J. Immunol.* 2006, 177, 6548-6559.
30) Nishimura, M. I.; Avichezer, D.; Custer, M. C.; Lee, C. S.; Chen, C.; Parkhurst, M. R.; Diamond, R. A.; Robbins, P. F.; Schwartzentruber, D. J.; Rosenberg, S. A. *Cancer Res.* 1999, 59, 6230-6238.
31) Schumacher, T. N. *Nat. Rev. Immunol.* 2002, 2, 512-519.
32) Morgan, R. A.; Dudley, M. E.; Wunderlich, J. R.; Hughes, M. S.; Yang, J. C.; Sherry, R. M.; Royal, R. E.; Topalian, S. L.; Kammula, U. S.; Restifo, N. P.; et al. *Science* 2006, 314, 126-129.
33) Toebes, M.; Coccoris, M.; Bins, A.; Rodenko, B.; Gomez, R.; Nieuwkoop, N. J.; van de Kasteele, W.; Rimmelzwaan, G. F.; Haanen, J.; Ovaa, H.; Schumacher, T. N. *Nat. Med.* 2006, 12, 246-251.
34) Grotenbreg, G. M.; Roan, N. R.; Guillen, E.; Meijers, R.; Wang, J.; Bell, G. W.; Starnbach, M. N.; Ploegh, H. L. *Proc. Natl. Acad. Sci. USA* 2008, 105, 3831-3836.
35) Bakker, A. H.; Hoppes, R.; Linnemann, C.; Toebes, M.; Rodenko, B.; Berkers, C. R.; Hadrup, S. R.; van Esch, W. J.; Heemskerk, M. H.; Ovaa, H.; Schumacher, T. N. *Proc. Natl. Acad. Sci. USA* 2008, 105, 3825-3830.
36) Sano, T.; Cantor, C. R. *Proc. Natl. Acad. Sci. USA* 1990, 87, 142-146.
37) Szymczak, A. L.; Workman, C. J.; Wang, Y.; Vignali, K. M.; Dilioglou, S.; Vanin, E. F.; Vignali, D. A. A. *Nat. Biotechnol.* 2004, 22, 589-594.
38) Garboczi, D. N.; Hung, D. T.; Wiley, D. C. *Proc. Natl. Acad. Sci. USA* 1992, 89, 3429-3433
39) W A Hendrickson, et al. PNAS Apr. 1, 1989 vol. 86 no. 7 2190-2194
40) Christopher Baugh, et al., J Mol Biol. 2000 Aug. 4; 301(1):117-28
41) Jennifer L. Meagher, et al., Glycobiology 2005 15(10): 1033-1042
42) C. Bustamante, et al., Science 265 (1994) 1599-600
43) John B. Hays, et al., Biopolymers, 8(4): 531-536
44) Isaac S Carrico et al *Nature Chemical Biology* 3, 321-322 (2007)
45) http://www.neb.com/nebecomm/products/cateol.asp?#2 Apr. 9, 2009
46) Schena M, Shalon D, Davis R W, Brown P O. *Science.* 1995 Oct. 20; 270(5235): 467-70
47) Dirks, R. M.; Lin, M.; Winfree, E.; Pierce, N. A. *Nucleic Acids Research* 2004, 32, (4), 1392-1403
48) Cardoso, A. A.; Watt, S. M.; Batard, P.; Li, M. L.; Hatzfeld, A.; Genevier, H.; Hatzfeld, J. *Exp. Hematol.* 1995, 23, 407-412
49) Breslauer, D. N.; Lee, P. J.; Lee, L. P. *Mol. BioSyst.* 2006, 2, 97-112
50) Zimmermann, M.; Delamarche, E.; Wolf, M.; Hunziker, P. *Biomedical Microdevices* 2005, 7, (2), 99-110
51) Cano et al., Science 2 Oct. 1992:Vol. 258. no. 5079, pp. 120-122

What is claimed is:

1. A method for sorting cells comprising:
combining a sample having a plurality of target cells with a plurality of capture agent sets, each capture agent set comprising a plurality of capture agents comprising a tetramer of an antigen-presenting MHC attached to an optimized streptavidin scaffold molecule and an encoding polynucleotide attached to the scaffold molecule, wherein the MHC specifically binds to a predetermined target cell and the encoding polynucleotide specifically binds to a complementary substrate polynucleotide and wherein each capture agent within a capture agent set binds the same target cells and binds the same complementary substrate polynucleotides;
forming target cell complexes of capture agents bound to the target cells;
combining the target cell complexes with a plurality of complementary substrate polynucleotide sets attached to a substrate; and
hybridizing the encoding polynucleotides to complementary substrate polynucleotides to sort target cell complexes.

2. The method of claim 1, wherein each capture agent has three encoding polynucleotides attached to the scaffold molecule.

3. The method of claim 1 further comprising a plurality of sets of capture agents, wherein each set of capture agents has encoding polynucleotides orthogonal to the encoding polynucleotides of each other set of capture agents and an MHC tetramer that binds to a target cell surface antigen different from the target cell surface antigen to which the other sets of MHC tetramers bind.

4. The method of claim 3, wherein the encoding polynucleotides of each set of capture agents encodes a restriction site different from the restriction enzyme site of the encoding polynucleotides of the other sets of capture agents.

5. The method of claim 4, wherein substrate bound target cells complexes are combined with restriction enzymes.

6. The method of claim 1, wherein the encoding polynucleotides are ssDNA oligomers.

7. The method of claim 1, wherein the capture agent further comprises a labeled molecule.

8. The method of claim 7, wherein the labeled molecule is selected from the group consisting of radioactive isotopes, fluorophores, chemiluminescent dyes, chromophores, enzymes, enzyme substrates, enzyme cofactors, enzyme inhibitors, dyes, metal ions, nanoparticles, metal sols, and ligands.

9. The method of claim 8 further comprising detecting a labeling signal.

10. The method of claim 1, wherein the MHC is an MHC class I, II or III protein.

11. The method of claim 10, wherein the MHC binds a T cell receptor.

12. The method of claim 1, wherein the target cells are selected from the group consisting of CD8, CD4, CD3 and antigen specific T cells.

13. The method of claim 12, wherein the T cell antigen is selected from the group consisting of MART-1, OVA, CMV, and tyrosinase.

14. The method of claim 1, wherein the optimized streptavidin scaffold molecule further comprises the amino acid sequence as set forth in SEQ ID NO:2.

* * * * *

SEQUENCE LISTING

<160> NUMBER OF SEQ ID NOS: 28

<210> SEQ ID NO 1
<211> LENGTH: 126
<212> TYPE: PRT
<213> ORGANISM: Streptomyces avidinii

<400> SEQUENCE: 1

```
His Met Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95
```

```
Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
            115                 120                 125

<210> SEQ ID NO 2
<211> LENGTH: 126
<212> TYPE: PRT
<213> ORGANISM: artificial sequence
<220> FEATURE:
<223> OTHER INFORMATION: Synthetic polypeptide

<400> SEQUENCE: 2

His Met Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
            35                  40                  45

Ser Ala Pro Ala Thr Asp Gly Ser Gly Thr Ala Leu Gly Trp Thr Val
        50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Gly Gly Ser Gly Cys Pro
            115                 120                 125

<210> SEQ ID NO 3
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 3
aaaaaaaaaa atcctggagc taagtccgta                                      30

<210> SEQ ID NO 4
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 4
aaaaaaaaaa gcctcattga atcatgccta                                      30

<210> SEQ ID NO 5
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 5
aaaaaaaaaa gcactcgtct actatcgcta                                      30

<210> SEQ ID NO 6
<211> LENGTH: 30
<212> TYPE: DNA
```

```
<213> ORGANISM: artificial sequence
<220> FEATURE:
<223> OTHER INFORMATION: Synthetic polynucleotide

<400> SEQUENCE: 6
aaaaaaaaaa tacggactta gctccaggat                                        30

<210> SEQ ID NO 7
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 7
aaaaaaaaaa taggcatgat tcaatgaggc                                        30

<210> SEQ ID NO 8
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 8
aaaaaaaaaa tagcgatagt agacgagtgc                                        30

<210> SEQ ID NO 9
<211> LENGTH: 9
<212> TYPE: PRT
<213> ORGANISM: artificial sequence
<220> FEATURE:
<223> OTHER INFORMATION: Synthetic polypeptide

<400> SEQUENCE: 9

Tyr Met Asp Gly Thr Met Ser Gln Val
1               5

<210> SEQ ID NO 10
<211> LENGTH: 10
<212> TYPE: PRT
<213> ORGANISM: artificial sequence
<220> FEATURE:
<223> OTHER INFORMATION: Synthetic polypeptide

<400> SEQUENCE: 10

Glu Leu Ala Gly Ile Gly Ile Leu Thr Val
1               5                   10

<210> SEQ ID NO 11
<211> LENGTH: 76
<212> TYPE: DNA
<213> ORGANISM: artificial sequence
<220> FEATURE:
<223> OTHER INFORMATION: Synthetic polynucleotide

<400> SEQUENCE: 11
aaaaaaaaaa aaaatcctgg agctaagtcc gtaaaaaaaa aaaatcctgg agctaagtcc       60
gtaaaaaaaa aaaaaa                                                       76

<210> SEQ ID NO 12
<211> LENGTH: 30
<212> TYPE: DNA
<213> ORGANISM: artificial sequence
<220> FEATURE:
<223> OTHER INFORMATION: Synthetic polynucleotide
```

```
<400> SEQUENCE: 12
aaaaaaaaaa tacggactta gctccaggat                                              30

<210> SEQ ID NO 13
<211> LENGTH: 76
<212> TYPE: DNA
<213> ORGANISM: artificial sequence
<220> FEATURE:
<223> OTHER INFORMATION: Synthetic polynucleotide

<400> SEQUENCE: 13
aaaaaaaaaa aaagcctcat tgaatcatgc ctaaaaaaaa aaagcctcat tgaatcatgc        60
ctaaaaaaaa aaaaaa                                                        76

<210> SEQ ID NO 14
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 14
aaaaaaaaaa taggcatgat tcaatgaggc                                              30

<210> SEQ ID NO 15
<211> LENGTH: 76
<212> TYPE: DNA
<213> ORGANISM: artificial sequence
<220> FEATURE:
<223> OTHER INFORMATION: Synthetic polynucleotide

<400> SEQUENCE: 15
aaaaaaaaaa aaagcactcg tctactatcg ctaaaaaaaa aaagcactcg tctactatcg        60
ctaaaaaaaa aaaaaa                                                        76

<210> SEQ ID NO 16
<211> LENGTH: 30
<212> TYPE: DNA
<213> ORGANISM: artificial sequence
<220> FEATURE:
<223> OTHER INFORMATION: Synthetic polynucleotide

<400> SEQUENCE: 16
aaaaaaaaaa tagcgatagt agacgagtgc                                              30

<210> SEQ ID NO 17
<211> LENGTH: 75
<212> TYPE: DNA
<213> ORGANISM: artificial sequence
<220> FEATURE:
<223> OTHER INFORMATION: Synthetic polynucleotide

<400> SEQUENCE: 17
aaaaaaaaaa aagagctaag tccgtagaat tcaaaaaaaa aagagctaag tccgtagaat        60
tcaaaaaaaa aaaaa                                                         75

<210> SEQ ID NO 18
<211> LENGTH: 36
<212> TYPE: DNA
<213> ORGANISM: artificial sequence
<220> FEATURE:
<223> OTHER INFORMATION: Synthetic polynucleotide

<400> SEQUENCE: 18
```
aaaaaaaaaa gaattctacg gacttagctc caggat                                    36

<210> SEQ ID NO 19
<211> LENGTH: 75
<212> TYPE: DNA
<213> ORGANISM: artificial sequence
<220> FEATURE:
<223> OTHER INFORMATION: Synthetic polynucleotide

<400> SEQUENCE: 19
aaaaaaaaaa aattgaatca tgcctaggat ccaaaaaaaa aattgaatca tgcctaggat    60
ccaaaaaaaa aaaaa                                                    75

<210> SEQ ID NO 20
<211> LENGTH: 36
<212> TYPE: DNA
<213> ORGANISM: artificial sequence
<220> FEATURE:
<223> OTHER INFORMATION: Synthetic polynucleotide

<400> SEQUENCE: 20
aaaaaaaaaa ggatcctagg catgattcaa tgaggc                                    36

<210> SEQ ID NO 21
<211> LENGTH: 9
<212> TYPE: PRT
<213> ORGANISM: artificial sequence
<220> FEATURE:
<223> OTHER INFORMATION: Synthetic polypeptide

<400> SEQUENCE: 21

Gly Leu Cys Thr Leu Val Ala Met Leu
1               5

<210> SEQ ID NO 22
<211> LENGTH: 9
<212> TYPE: PRT
<213> ORGANISM: artificial sequence
<220> FEATURE:
<223> OTHER INFORMATION: Synthetic polypeptide

<400> SEQUENCE: 22

Asn Leu Val Pro Met Val Ala Thr Val
1               5

<210> SEQ ID NO 23
<211> LENGTH: 8
<212> TYPE: PRT
<213> ORGANISM: artificial sequence
<220> FEATURE:
<223> OTHER INFORMATION: Synthetic polypeptide

<400> SEQUENCE: 23

Ser Ile Ile Asn Phe Glu Lys Leu
1               5

<210> SEQ ID NO 24
<211> LENGTH: 9
<212> TYPE: PRT
<213> ORGANISM: artificial sequence
<220> FEATURE:
<223> OTHER INFORMATION: Synthetic polypeptide

<400> SEQUENCE: 24

Lys Val Pro Arg Asn Gln Asp Trp Leu
1               5

```
<210> SEQ ID NO 25
<211> LENGTH: 136
<212> TYPE: PRT
<213> ORGANISM: artificial sequence
<220> FEATURE:
<223> OTHER INFORMATION: Synthetic polypeptide

<400> SEQUENCE: 25
```

His Met Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Gly Gly Ser Gly Cys Gly Gly Ser
        115                 120                 125

Gly Cys Gly Gly Ser Gly Cys Pro
    130                 135

```
<210> SEQ ID NO 26
<211> LENGTH: 17
<212> TYPE: PRT
<213> ORGANISM: artificial sequence
<220> FEATURE:
<223> OTHER INFORMATION: Synthetic polypeptide

<400> SEQUENCE: 26
```

Gly Gly Gly Leu Asn Asp Ile Phe Glu Ala Gln Lys Ile Glu Trp His
1               5                   10                  15

Glu

```
<210> SEQ ID NO 27
<211> LENGTH: 13
<212> TYPE: PRT
<213> ORGANISM: artificial sequence
<220> FEATURE:
<223> OTHER INFORMATION: Synthetic polypeptide

<400> SEQUENCE: 27
```

Leu Cys Thr Pro Ser Arg Gly Ser Leu Phe Thr Gly Arg
1               5                   10

```
<210> SEQ ID NO 28
<211> LENGTH: 10
<212> TYPE: RNA
<213> ORGANISM: artificial sequence
<220> FEATURE:
<223> OTHER INFORMATION: Synthetic polynucleotide

<400> SEQUENCE: 28
```
uuuuuuuuuu                                                          10